US006858775B1

(12) United States Patent
Xu et al.

(10) Patent No.: US 6,858,775 B1
(45) Date of Patent: Feb. 22, 2005

(54) METHOD FOR GENERATING SPLIT, NON-TRANSFERABLE GENES THAT ARE ABLE TO EXPRESS AN ACTIVE PROTEIN PRODUCT

(75) Inventors: Ming-Qun Xu, Hamilton, MA (US); Thomas C. Evans, Somerville, MA (US); Sriharsa Pradhan, Beverly, MA (US); Donald G. Comb, Manchester, MA (US); Henry Paulus, Boston, MA (US); Luo Sun, Hamilton, MA (US); Lixin Chen, Beverly, MA (US); Inca Ghosh, Somerville, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/936,588

(22) PCT Filed: May 23, 2000

(86) PCT No.: PCT/US00/14122

§ 371 (c)(1),
(2), (4) Date: Mar. 29, 2002

(87) PCT Pub. No.: WO00/71701

PCT Pub. Date: Nov. 30, 2000

Related U.S. Application Data

(60) Provisional application No. 60/135,677, filed on May 24, 1999.

(51) Int. Cl.$^7$ .............................................. A01H 1/00
(52) U.S. Cl. ....................................................... 800/278
(58) Field of Search ................................ 435/468, 471, 435/69.1, 91.4, 455, 91.41, 91.42; 800/278

(56) References Cited

U.S. PATENT DOCUMENTS 5,496,714 A    3/1996    Combs et al.
5,834,247 A   11/1998    Combs et al.
6,270,964 B1 * 8/2001    Michnick et al.

OTHER PUBLICATIONS

Ferber, D., Science 286: 1662 (1999).
Losey, et al., Nature 399: 214 (1999).
Bergelson, et al., Nature 395: 25 (1998).
Gressel, Trends Biotechnol., 17: 361–366 (1999).
Bertolla and Simonet, Res. Microbiol., 150: 375–384 (1999).
Chong, et al., J. Biol. Chem., 271: 22159–22168 (1996).
Camarero and Muir, J. Amer. Chem. Soc., 121: 5597–5598 (1999).
Chong, et al., Gene, 192: 271–281 (1997).
Chong, et al., Nucleic Acids Res., 26: 5109–5115 (1998).
Chong, et al., J. Biol. Chem., 273: 10567–10577 (1998).
Cotton, et al., J. Am. Chem. Soc., 121: 1100–1101 (1999).
Evans, et al., J. Biol. Chem., 274: 18359–18363 (1999).
Evans, et al., J. Biol. Chem., 274: 3923–3926 (1999).
Evans, et al., Protein Sci., 7: 2256–2264 (1998).
Evans, et al., J. Biol. Chem., 275: 9091–9094 (2000).
Iwal and Pluckthun, FEBS Lett., 459: 166–172 (1999).
Mathys, et al., Gene, 231:1–13 (1999).
Mills, et al., Proc. Natl. Acad. Sci. USA 95: 3543–3548 (1998).
Muir, et al., Proc. Natl. Acad. Sci. USA 95: 6705–6710 (1998).
Otomo, et al., Biochemistry 38: 16040–16044 (1999).
Otomo, et al., J. Biolmol. NMR 14: 105–114 (1999).
Scott, et al., Proc. Natl. Acad. Sci. USA 96: 13638–13643 (1999).
Severinov and Muir, J. Biol. Chem., 273: 16205–16209 (1998).
Shingledecker, et al., Gene, 207: 187–195 (1998).
Southworth, et al., EMBO J., 17: 918–926 (1998).
Southworth, et al., Biotechniques, 27: 110–120 (1999).
Wood, et al., Nat. Biotechnol., 17: 889–892 (1999).
Wu, et al., Proc. Natl. Acad. Sci. USA 95: 9226–9231 (1998a).
Wu, et al., Biochim Biophys Acta 1387: 422–432 (1998b).
Xu, et al., Proc. Natl. Acad. Sci. USA 96: 388–393 (1999).
Yamazaki, et al., J. Am. Chem. Soc., 120: 5591–5592 (1998).
Lew, et al., J. Biol. Chem., 273: 15887–15890 (1998).
Wu, et al., Biochim. Biophys. Acta 35732: 1 (1998b).
LaRossa and Schloss, J. Biol. Chem., 259: 8753–8757 (1984).
Chaleff and Ray, Science, 223: 1148–1151 (1984).
Falco and Dumass, Genetics, 109: 21–35 (1985).
Stalker, et al., J. Biol. Chem., 260: 4724–4728 (1985).
Short and Colburn, Toxicol. Ind. Health, 15: 240–275 (1999).
Hill, et al., Biochem. J., 335: 653–661 (1998).
Lee, et al., EMBO J., 7: 1241–1248 (1988).
Bernasconi, et al., J. Biol. Chem., 270: 17381–17385 (1995).
DeFelice, et al., Ann. Microbiol. (Paris) 133A: 251–256 (1982).
Biery, et al., Nucleic Acids Res., 28: 1067–1077 (2000).
Kelley, Proc. Natl. Acad. Sci. USA 85(11): 3980–3984 (1988).
Alexander, Neuron 3(1):133–139 (1989).
Sambrook, et al., Molecular Cloning: A Laboratory Manual, 2nd Edition, Cold Spring Harbor Laboratory, NY: Cold Spring Harbor Laboratory Press (1989).
InBase at http://www.neb.com/neb/frame_tech.html.
Perler, et al., Nucleic Acids Res., 28: 344–345 (2000).

(List continued on next page.)

Primary Examiner—Terry McKelvey
(74) Attorney, Agent, or Firm—Harriet M. Strimpel; Gregory D. Williams

(57) ABSTRACT

A new type of transgene system is disclosed which allows efficient protein expression in a target host such as a plant, but avoids the undesirable result of the migration of the transgene into related host system and/or to the environment via the pollen. The methods described herein may also be applied to the expression of virtually any protein of interest (e.g. a toxic protein) in eukaryotic (yeast, insect, mammalian cells, etc.) and prokaryotic (*E. coli*, etc.) organisms.

18 Claims, 33 Drawing Sheets

OTHER PUBLICATIONS

Pietrokovski, Protein Sci. 7: 64–71 (1998).
Perler, et al., Nucleic Acids Res. 25: 1087–1093 (1997).
Xu, et al., EMBO J. 15: 5146–5153 (1996).
Chong, et al., Biochem. Biophys. Res. Commun., 259:136–140 (1999).
Chong and Xu, J. Biol. Chem., 272: 15587–15590 (1997).
Paulus, Chem. Soc. Rev., 27: 375–386 (1998).
Pietrokovski, et al., Protein Sci., 3: 2340–2350 (1994).
Shingledecker, et al., Arch. Biochem. Biophys., 375: 138–144 (2000).
Telenti, et al., J. Bacteriol., 179: 6378–6382 (1997).
Rossi, et al., Trends Cell Biol., 10: 119–122 (2000).
Yadav, et al., Proc. Natl. Acad. Sci. USA 83: 4418–4422 (1986).
Maxwell, et al., Cancer Res. 51(16): 4299–4304 (1991).
Madshus, J. Biol. Chem., 269(26): 17723–17729 (1994).
Murphy and vanderSpeck, Semin Cancer Biol. 6(5): 259–267 (1995).
Rozemuller and Rombouts, Leukemia, 12(5): 710–717 (1998).
Veggeberg, Mol. Med. Today, 4(3): 93 (1998).
Kreitman, Current Opin. Immunol., 11(5): 570–578 (1999).
Vallera, et al., Protein Eng., 12(9): 779–785 (1999).
Groner, et al., J. Physiol., 84(1): 53–77 (1990).
Patil, et al., Neuron 4(3): 437–447 (1990).
Aloe, et al., Growth Factors 9(2): 149–155 (1993).
Aguzzi, et al., Brain Pathol. 4(1): 3–20 (1994).
Groner, et al., Biomed. Pharmacother. 48(5–6): 231–240 (1994).
Schorderet, Experientia 51(2): 99–105 (1995).
Gustin, et al., Methods Mol. Biol., 130: 85–90 (2000).
Hobson, et al., Methods Mol. Biol., 57: 279–285 (1996).
Ibdah, et al., Biochemistry, 35: 16282–16291 (1996).
Murray and Thompson, Nucleic Acids Res., 8: 4321–4325 (1980).
Horsch, et al., Science 227: 1229–1231 (1985).
Jefferson, et al., EMBO J., 6: 3901–3907 (1987).
Xu, M–Q., The NEB Transcript, Jan. 1997, vol. 8, No. 2, pp. 1–5.
"Genetically Engineered Crops May Threaten Beneficial Insects," Aug. 31, 1998, Pesticide Action Network North America Updates Service.
"Mycobacterial DNA Gyrase Precursor Protein and Polypeptides Corresponding to Mycobacterial DNA Gyrase Intein Sequences," Institut Pas.
"Monarch Butterfly Larvae Harmed By Transgenic Pollen," Friday, Apr. 7, 2000.
"Codex Alimentarius Decided to Support rBGH Moratorium," PR Newswire Press Release, Aug. 18, 1999.
Carman, Judy, MPH, PhD, Flinders University, "The Problem With the Safety of Roundup Ready Soybeans".
Regal, Philip J., Metaphysics in Genetic Engineering: Cryptic Philosophy and Ideology in the 'Science.
Ferrara, Jennifer, "Revolving Doors: Monsanto and the Regulators" The Ecologist, Sep. / Oct. 1998.
"Substainability and Ag Biotech," Environment and Health Weekly, #686, Feb. 10, 2000.
"Panel Sees Use for Genetically Altered Crops," Free Press News Service, Oct. 14, 1997.
"Poison Plants? Genetically Modified Crops, Grown Over Much of the U.S., Remain Controversial," Scientific American, Jul. 5, 1999.
Carpenter, Janet and Leonard Gianessi, "Herbicide Use on Roundup Ready Crops" Science Magazine.
"International Panel for GM food?" Nature, Mar. 9, 2000, vol. 404 Issue No. 6774.
Masood, Ehsan "Europe and US in Confrontation Over GM Food Labelling Criteria" Nature, vol. 398, p. 641, Apr. 22, 1999.
Dickson, David "UK Debates Public's Role in Science Advice" Nature, vol. 399, p. 188, May 20, 1999.
Masood, Ehsan "Africa Seeks Laws on GM Food Exports . . . " Nature, vol. 400, p. 495, Aug. 5, 199.
Enserink, Martin "Industry Response: Ag Biotech Moves to Mollify Its Critics" Science Magazine, 286: 1666–1668, 1999.
Ferber, Dan "Biotech Critics Watch the Watchdogs" Science Magazine, 286: 1664, 1999.
Wallimann, Theo "Bt Toxin: Assessing GM Strategies" Science Magazine.
Ferber, Dan "Monarch Press Release Raises Eyebrows" Science Magazine, 286: 1663, 1999.
Jacobson, Michael "The Genetically Modified Food Fight" West J. Med. 172: 220–221, 2000.
Ferber, Dan "Risks and Benefits: GM Crops in the Cross Hairs" Science Magazine 286: 1662–1.

* cited by examiner

FIG. 6

```
327 Y A V D K A D L L A L   G V R F D D R V T G K I E A F A S R   Maize ALS
356 Y A V D S S D L L L A F G V R F D D R V T G K L E A F A S R   Tobacco ALSI
353 Y A V D S S D L L L A F G V R F D D R V T G K L E A F A S R   Tobacco ALSII
268 M T M H N A D V I F A V G V R F D D R T T N N L A K Y C P N   E. Coli ALSIII
258 F A V Q E C D L L I A V G A R F D D R V T G K L N T S A P H   E. Coli ALSII 357 A K I V H V D I D P A E I G K N K Q P H V S I C A D V K L A   Maize ALS
386 A K I V H I D I D S A E I G K N K Q P H V S I C A D I K L A   Tobacco ALSI
383 A K I V H I D I D S A E I G K N K Q P H V S I C A D I K L A   Tobacco ALSII
298 A T V L H I D I D P T S I S K T V T A D I P I V G D A R Q V   E. Coli ALSIII
288 A S V I H M D I D P A E M N K L R Q A H V A L Q C D L N A L   E. Coli ALSII

*
387 L Q G M N A L L E G S T S K K S F D - F G S W N D E L D Q Q   Maize ALS
416 L Q G L N S I L E S K E G K L K L D - F S A W R Q E L T E Q   tobacco ALSI
413 L Q G L N S I L E S K E G K L K L D - F S A W R Q E L T V Q   tobacco ALSII
328 L E Q M L E L L S Q E S A H Q P L D E I R D W W Q Q I E Q W   E. Coli ALSIII
318 L P A L Q Q P L N Q C D - - - - - - - - - W Q Q H C A Q L   E. Coli ALSII
                    ▲

416 K R E F P L C Y K T S N E E I Q P Q Y A I Q V L D E L T K G   Maize ALS
445 K V K H P L N F K T F G D A I P P Q Y A I Q V L D E L T N G   tobacco ALSI
442 K V K Y P L N F K T F G D A I P P Q Y A I Q V L D E L T N G   tobacco ALSII
358 R A R Q C L K Y D T H S E K I K P Q A V I E T L W R L T K G   E. Coli ALSIII
338 R D E H S W R Y D H P G D A I Y A P L L L K Q L S D R K P A   E. Coli ALSII 446 E A I I G T G V G Q H Q M W A A Q Y Y T Y K R P R Q W L S S   Maize ALS
475 N A I I S T G V G Q H Q M W A A Q Y Y K Y R K P R Q W L T S   tobacco ALSI
472 S A I I S T G V G Q H Q M W A A Q Y Y K Y R K P R Q W L T S   tobacco ALSII
388 D A Y V T S D V G Q H Q M F A A L Y Y P F D K P R W I N S   E. Coli ALSIII
368 D C V V T I D V G Q H Q M W A A Q H I A H T R P E N F I T S   E. Coli ALSII 476 A G L G A M G F G L P A A A G A S V A N P G V T V V D I D G   Maize ALS
505 C G L G A M G F G L P A A I G A A V G R P D E V V V D I D G   tobacco ALSI
502 G G L G A M G F G L P A A I G A A V G R P D E V V V D I D G   tobacco ALSII
418 G G L G T M G F G L P A A L G V K M A L P E R T V V C V T G   E. Coli ALSIII
398 S G L G T M G F G L P A A V G A Q V A R P N D T V V C I S G   E. Coli ALSII
```

FIG. 15-1

| EPSPS Insertion Site | Amino acid sequence inserted | Clone |
|---|---|---|
| Q7/P8 | CLNIQ | pCE-5aa 129 |
| A10/R11 | VFKHA | pCE-5aa 47 |
| P35/C36 | LFKQP | pCE-5aa 7 |
| D48/D49 | CLNSD | pCE-5aa 50 |
| S67/A68 | CLNIS | pCE-5aa 8 |
| D69/R70 | CLNTD | pCE-5aa 44 |
| R70/T71 | CLNNR | pCE-5aa 10 |
| C73/D74 | CLNSC | pCE-5aa 32 |
| D74/I75 | CLNSD | pCE-5aa 5 |
| L82/R83 | CLNTL | pCE-5aa 3 |
| P85/G86 | VFKQP | pCE-5aa 12 |
| M121/K122 | CLNSM | pCE-5aa 42 |
| Y148/P149 | CLNNY | pCE-5aa 37 |
| L182/A183 | CLNTL | pCE-5aa 22 |
| A183/P184 | CLNMA | pCE-5aa 11 |
| K185/D186 | VFKHK | pCE-5aa 112 |
| K185/D186 | CLNTK | pCE-5aa 212 |
| D186/T187 | CLNKD | pCE-5aa 33 |
| I188/I189 | MFKQI | pCE-5aa 151 |
| I189/R190 | CLNII | pCE-5aa 114 |
| E194/L195 | LFKHE | pCE-5aa 227 |
| F211/G212 | VFKHF | pCE-5aa 162 |
| V213/E214 | CLNSV | pCE-5aa 1 |
| I215/A216 | VFKQI | pCE-5aa 2 |
| A216/N217 | MFKQA | pCE-5aa 208 |
| H218/H219 | LFKHH | pCE-5aa 28 |
| Q221/Q222 | LFKHQ | pCE-5aa 4 |
| V225/K226 | MFKHV | pCE-5aa 203 |
| K226/G227 | VFKQK | pCE-5aa 25 |
| Q230/Y231 | LFKQQ | pCE-5aa 102 |
| S233/P234 | LFKHS | pCE-5aa 40 |
| G235/R236 | CLNTG | pCE-5aa 35 |
| R267/K268 | CLNSR | pCE-5aa 23 |
| L238/V239 | VFKHL | pCE-5aa 154 |

FIG. 15-2

| EPSPS Insertion Site | Amino acid sequence inserted | Clone |
|---|---|---|
| I311/P312 | CLNNI | pCE-5aa 29 |
| Q375/H376 | LFKHQ | pCE-5aa 15 |
| Q375/H376 | CLNIQ | pCE-5aa 223 |
| H376/A377 | CLNKH | pCE-5aa 38 |
| Y382/N383 | MFKQY | pCE-5aa 31 |
| E418/Q419 | LFKHE | pCE-5aa 36 |
| Q419/L420 | CLNKQ | pCE-5aa 46 |
| S424/T425 | CLNMS | pCE-5aa 9 |

FIG. 16

| EPSPS Insertion Site | Amino acid sequence inserted | Clone |
|---|---|---|
| L31/A32 | LCLNILA | pCE-5aa 21d |
| N55/A56 | NCLNINA | pCE-5aa 4d |
| L57/S58 | LMFKHLS | pCE-5aa 217 |
| I71/R72 | TLFKHTR | pCE-5aa 24d |
| K122/E123 | KVFKQKE | pCE-5aa 126 |
| H128/L129 | HLVFKHL | pCE-5aa 142 |
| L176/L177 | LCLNTLL | pCE-5aa 122 |
| L238/V239 | LCLNNLV | pCE-5aa 205 |
| E240/G241 | EVFKHEG | pCE-5aa 171 |
| K256/G257 | KVFKQKG | pCE-5aa 140 |
| T286/I287 | TCLNTTI | pCE-5aa 180 |
| M328/N329 | MCLNNMN | pCE-5aa 115 |
| L331/R332 | LLFKQLR | pCE-5aa 124 |
| R344/L345 | RCLNNRL | pCE-5aa 107 |
| M348/A349 | MVFKQMA | pCE-5aa 3d |
| A349/T350 | AMFKQAT | pCE-5aa 110 |
| L404/D405 | LVFKHLD | pCE-5aa 199 |
| K411/T412 | KMFKQKT | pCE-5aa 5d |
| Y416/F417 | YCLNNYF | pCE-5aa 163 |

FIG. 18

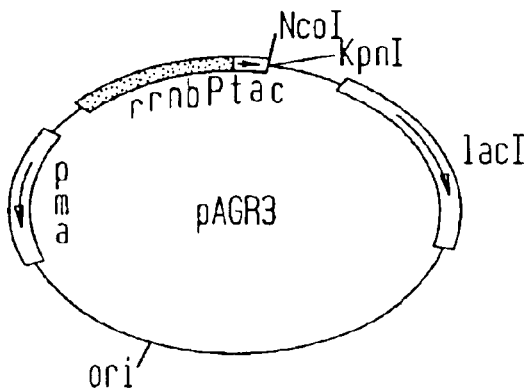

EXPRESSION PLASMID pAGR3: 5910 bp.
PROMOTER AND CLONING SITE MAP:

```
       lac operator
  1 GAATTGTGAG CGCTCACAAT TCTAGGATGT TAATTGCGCC GACATCATAA -35 region
 51 CGGTTCTGGC AAATATTCTG AAATGAGCTG TTGACAATTA ATCATCGGCT -10 region      lac operator                 rbs
101 CGTATAATGT GTGGAATTGT GAGCGGATAA CAATTTCACA CAGGAAACAG start
151 ACCATGGTGA ATTCTAGAGC TCGAGGATCC GCGGTACCCG GGCATGCATT
       NcoI     EcoRI XbaI SacI XhoI BamHI SacII KpnI SmaI        BstBI 201 CGAAGCTTCC TTAAGCGGCC GTCGACCGAT GCCCTTGAGA GCCTTCAACC
       HindIII AflII    EagI   SalI
```

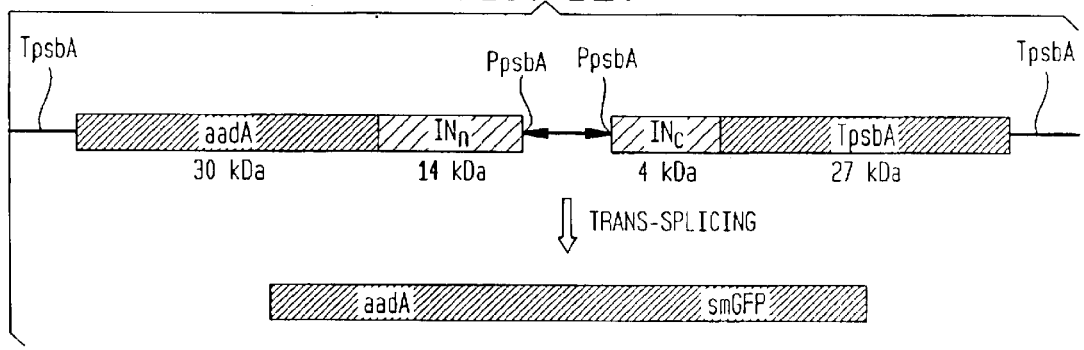
FIG. 21A
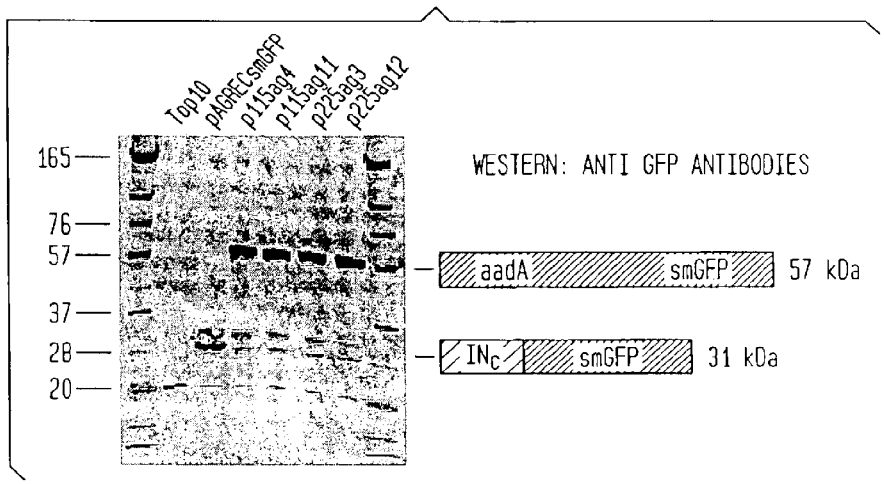
FIG. 21B
FIG. 21C

FIG. 24

GAATAGATCTACATACACCTTGGTTGACACGAGTATATAAGTCATGTT
ATACTGTTGAATAACAAGCCTTCCATTTTCTATTTTGATTTGTAGAAA
ACTAGTGTGCTTGGGAGTCCCTGATGATTAAATAAACCAAGATTTTAC
CTTAATTAAG

FIG. 25

GATCCTGGCCTAGTCTATAGGAGGTTTTGAAAAGAAAGGAGCAATAAT
CATTTCTTGTTCTATCAAGAGGGTGCTATTGCTCCTTTCTTTTTTTC
TTTTTATTTATTTACTAGTATTTTACTTACATAGACTTTTTTGTTTAC
GTATTCT

FIG. 26 catATGGCgTCcATGATcTCCTCgTCcGCgGTGACcACgGTCAGCCGcG
CgTCcACGGTGCAgTCGGCCGCGGTGGCcCCgTTCGGCGGCCTCAAgTC
CATGACcGGcTTCCCgGTcAAGAAGGTCAACACgGACATcACgTCCATc
ACgAGCAAcGGcGGcAGgGTgAAGTGCATGcgaagagc

FIG. 27-1

```
GTTAACTACGTCAGGTGGCACTTTTCGGGGAAATGTGCGCGGAACCC
CTATTTGTTTATTTTTCTAAATACATTCAAATATGTATCCGCTCATG
AGACAATAACCCTGATAAATGCTTCAATAATATTGAAAAAGGAAGAG
TATGAGTATTCAACATTTCCGTGTCGCCCTTATTCCCTTTTTTGCGG
CATTTTGCCTTCCTGTTTTTGCTCACCCAGAAACGCTGGTGAAAGTA
AAAGATGCTGAAGATCAGTTGGGTGCACGAGTGGGTTACATCGAACT
GGATCTCAACAGCGGTAAGATCCTTGAGAGTTTTCGCCCCGAAGAAC
GTTCTCCAATGATGAGCACTTTTAAAGTTCTGCTATGTGGCGCGGTA
TTATCCCGTGTTGACGCCGGGCAAGAGCAACTCGGTCGCCGCATACA
CTATTCTCAGAATGACTTGGTTGAGTACTCACCAGTCACAGAAAAGC
ATCTTACGGATGGCATGACAGTAAGAGAATTATGCAGTGCTGCCATA
ACCATGAGTGATAACACTGCGGCCAACTTACTTCTGACAACGATCGG
AGGACCGAAGGAGCTAACCGCTTTTTTGCACAACATGGGGGATCATG
TAACTCGCCTTGATCGTTGGGAACCGGAGCTGAATGAAGCCATACCA
AACGACGAGCGTGACACCACGATGCCTGTAGCAATGGCAACAACGTT
GCGCAAACTATTAACTGGCGAACTACTTACTCTAGCTTCCCGGCAAC
AATTAATAGACTGGATGGAGGCGGATAAAGTTGCAGGACCACTTCTG
CGCTCGGCCCTTCCGGCTGGCTGGTTTATTGCTGATAAATCTGGAGC
CGGTGAGCGTGGGTCTCGCGGTATCATTGCAGCACTGGGGCCAGATG
GTAAGCCCTCCCGTATCGTAGTTATCTACACGACGGGGAGTCAGGCA
ACTATGGATGAACGAAATAGACAGATCGCTGAGATAGGTGCCTCACT
GATTAAGCATTGGTAACTGTCAGACCAAGTTTACTCATATATACTTT
AGATTGATTTACCCCGGTTGATAATCAGAAAAGCCCCAAAAACAGGA
AGATTGTATAAGCAAATATTTAAATTGTAAACGTTAATATTTTGTTA
AAATTCGCGTTAAATTTTTGTTAAATCAGCTCATTTTTTAACCAATA
GGCCGAAATCGGCAAAATCCCTTATAAATCAAAAGAATAGCCCGAGA
TAGGGTTGAGTGTTGTTCCAGTTTGGAACAAGAGTCCACTATTAAAG
AACGTGGACTCCAACGTCAAAGGGCGAAAAACCGTCTATCAGGGCGA
TGGCCCACTACGTGAACCATCACCCAAATCAAGTTTTTTGGGGTCGA
GGTGCCGTAAAGCACTAAATCGGAACCCTAAAGGGAGCCCCCGATTT
AGAGCTTGACGGGGAAAGCGAACGTGGCGAGAAAGGAAGGGAAGAAA
GCGAAAGGAGCGGGCGCTAGGGCGCTGGCAAGTGTAGCGGTCACGCT
GCGCGTAACCACCACACCCGCCGCGCTTAATGCGCCGCTACAGGGCG
CGTAAAAGGATCTAGGTGAAGATCCTTTTTGATAATCTCATGACCAA
AATCCCTTAACGTGAGTTTTCGTTCCACTGAGCGTCAGACCCCGTAG
AAAAGATCAAAGGATCTTCTTGAGATCCTTTTTTTCTGCGCGTAATC
TGCTGCTTGCAAACAAAAAAACCACCGCTACCAGCGGTGGTTTGTTT
GCCGGATCAAGAGCTACCAACTCTTTTTCCGAAGGTAACTGGCTTCA
GCAGAGCGCAGATACCAAATACTGTTCTTCTAGTGTAGCCGTAGTTA
GGCCACCACTTCAAGAACTCTGTAGCACCGCCTACATACCTCGCTCT
GCTAATCCTGTTAC
```

FIG. 27-2

```
CAGTGGCTGCTGCCAGTGGCGATAAGTCGTGTCTTACCGGGTTGGA
CTCAAGACGATAGTTACCGGATAAGGCGCAGCGGTCGGGCTGAACG
GGGGGTTCGTGCACACAGCCCAGCTTGGAGCGAACGACCTACACCG
AACTGAGATACCTACAGCGTGAGCTATGAGAAAGCGCCACGCTTCC
CGAAGGGAGAAAGGCGGACAGGTATCCGGTAAGCGGCAGGGTCGGA
ACAGGAGAGCGCACGAGGGAGCTTCCAGGGGGAAACGCCTGGTATC
TTTATAGTCCTGTCGGGTTTCGCCACCTCTGACTTGAGCGTCGATT
TTTGTGATGCTCGTCAGGGGGGCGGAGCCTATGGAAAAACGCCAGC
AACGCGGCCTTTTTACGGTTCCTGGCCTTTTGCTGGCCTTTTGCTC
ACATGTAATGTGAGTTAGCTCACTCATTAGGCACCCCAGGCTTTAC
ACTTTATGCTTCCGGCTCGTATGTTGTGTGGAATTGTGAGCGGATA
ACAATTTCACACAGGAAACAGCTATGACCATGATTACGCCAAGCTA
CGTAATACGACTCACTAGTGGGCAGATCTTCGAATGCATCGCGCGC
TTGACGATATAGCAATTTTGCTTGGATTTATCAGTCGAAGCAGGAG
ACAATATACCTTGATATTCTCGATCATTCTTTGATTCAAAGCATCG
TTCCATCTCAATTGAAAAAGCAAATAACGTTTCAAGAACAAATCTA
GTTCTGCTTCCGTGTTGCTTTTGTATTGTTTTTCTTTTTACCCTT
CTTTGTGTCTGATTCCGCGTAATCTTTTTTAAGAGCGTTTTGATGT
TTTGAGAGAACAGGGCCCAGATTTCCTTTGTTTTCTATATCTGATC
CACGCTCTTTTTCTCCTTGACTTGCGGGTTCTTTTGCTTCTTGAAT
TCGATTCTTTATTTTTTTATTTGATCGTAGAAAAAAGTTTTGTTTT
TGGTTTTTATTGATGTTTTTATTTTGACTAACATTTTCATTTGTAT
TCAAATTTAAAAGAAGTAATTTGCTTGGTATAATCCACGGTTTTAT
TTTATATACATTATAAAGTGGTACAAATTCTGGGAAGAACCAAAAT
TCCAGATTCAATATGGGACGATTTAATATTTTTTCATTCATTCCCA
TCCAATCAAAAAAGGCTTTTTTCGAATTTTTTTGATTGTTTTCTGG
ATTTTGATGAATCGTAAGATAAAAAAAGCCTTTTTTATCAATTTTA
TCAATTATTTGATAATTATTAATACCAATTTTAGTATTTGGATTAC
TGTTGGTATCGATCTTAACCCAGGCCTCAATATCTTCTTTTTGTCT
AAGAGAAAAATGGATAATTTTCCAATCAAAATATTTTCTATCGAGA
TTTCTTTCTATATATAGAATATTGCCTTTTCTTAGATAATTATTGA
TATGAAGATTGCCGAGCATATCAAAAAGGTTGTGTTTGGACGTGTT
GGAATTAGAAGAAATTTCGAGGTTCTTATTTACTTGAAAGGGTAAT
CTAGAAATAAAAGAGTCATTTTTTTTTCATAATTAATCGATTTAT
ATGCTAAAAGATCATATCTATAACATTTTTGAAAATTATCTTTTTG
GTTTGCTAATGAATAGAGCTCAGAATCATTTTCTTTTTTGTAATGA
ATTAATTGGTCTTTTTCATATGAATTCCATTTGTTTAAATTTCGAT
TTTGAGCCATACAACCTTGATTAACCCTATTTCGCCATTTTTGTGG
CATTAATCTAGACCATCTAATCTGAGATAAATCGTACGagaatact
caatCATGAATAAATGCAAGAAAATAACCTCTCCTTCTTTTTTCTAT
AATGTAAACAAAAAAGTCTATGTAAGTAAAATACTAGTAAATAAAT
AAAAAGAAAAAAAGAAAGGAGCAATAGCACCCTCTTGATAGAACAA
GAAAATGATTAT
```

FIG. 27-3

```
TGCTCCTTTCTTTTCAAAACCTCCTATAGACTAGGCCAGGATCCTCGA
GcttaattaaGGTAAAATCTTGGTTTATTTAATCATCAGGGACTCCCA
AGCACACTAGTTTTCTACAAATCAAAATAGAAAATAGAAAATGGAAGG
CTTTTTATTCAACAGTATAACATGACTTATATACTCGTGTCAACCAAG
GTGTATGTAGATCtattcCTGCAGGATATCTGGATCCACGAAGCTTCC
CATGGGAATAGATCTACATACACCTTGGTTGACACGAGTATATAAGTC
ATGTTATACTGTTGAATAAAAAGCCTTCCATTTTCTATTTTGATTTGT
AGAAAACTAGTGTGCTTGGGAGTCCCTGATGATTAAATAAACCAAGAT
TTTACCGTTTAAACACCGGTGATCCTGGCCTAGTCTATAGGAGGTTTT
GAAAAGAAAGGAGCAATAATCATTTTCTTGTTCTATCAAGAGGGTGCT
ATTGCTCCTTTCTTTTTTTCTTTTTATTTATTTACTAGTATTTTACTT
ACATAGACTTTTTTGTTTACATTATAGAAAAAGAAGGAGAGGTTATTT
TCTTGCATTTATTCATGATTGAGTATTCTcctaggCGTATTGATAATG
CCGTCTTAACCAGTTTTTCCATTGATTGATTCTATAACTCTGAAGTTT
CTTATGTTTTAATTCAGAATGAAATATTCCTAGTGTTCGAAAATAGTC
CTTTATTTTAGTCTTAAGGAAAAAAGACGTTCTGTTATATTGAAGAAC
AGATCTTAATTTAGACAAATTAATAACTTGGGGTTGTGATAATTTGTA
AAATACATATGCTTGTGATAAGTAGGATAAATCAAAAAAAATATGTGA
ATTTTTCTTACTAATATTATAAAGTGACTTTTTTATAGTCGAAATAAA
GTGAATTTTTTTTTGATTATTAATTTTTCTTGATTTATTTCATTATT
GGAAATGTATTTATCAATCAATTTGTTTGTTGATTCAAGAAAGAGTTG
TGTATTAATTCTGGGAATATTAATGATAGATAAAAATAGATCGATGTA
TAATCTTTGAATGAATAATTTTAGAAAATAATGGAATTTCCATATTAA
TCGAGTATTTCTTCTTTTTAATATTTGGAAAATCTTTTTTGGCGATTC
GAATTTTTTAATATTATTTGTTTTATTAGGACTAATGTCTATTTCTGG
AGTTACTTTCTTTTTCTCTTTTGTAATTCTTTCTATTTGATTTTTGAT
TGTACTTGTTCTATCAGTCAAATCCTTCATTTTGCTTTCTATCAGTGA
AGAATTTGGCCAATTTCCAGATTCAATTTGACTAAATGATTCGTTAAT
TATCTGATTACTCATTAGAGAATCTTTTTCTTTTTTCGTTTCATTCGA
TTCATCTATTTCTTTGAGTCTAAATAATACAATTGGATTTACTTTTGA
AAGTTCTTTTTTCATTTTTTTATAAATAGACTACTTTTGATAAGCCA
TTTTTTGGTTTCTTTTGAAATTCTTCGAAATAATTTTATTTTTCCTTT
GAAAACTTTTAGAGTTATAAAATATTTCTTTTTGAATTTTCCAATTTT
TTTTTCGAGTTCCTTAAAAATGGGCTCAAAAAAAGAAGGGCGTTTTCG
GGGAGAACCAAAGGGAAGTTCAGCTTCCATTCCCCAAACTGTTAAAAA
ACAAAAATCATCTTTTTGTTTTTTCTTTTTCATTAGCTCTCCACGGGA
GGAGTACAGTTTAGATATATGCCAAGGTTTCAGACAAAAAGGAAATAA
TATTTTGATCTGAATGCCATCTTTCAACCAATTTTTTGGAAATTCTGT
TTCTGATAATTGAACACCATTATAAGTACATTTAATATGCATTTCTCT
ATTCCATTCCTGCAAATCTTCAGACCATTCAGGAAGTTGCAAGACTAA
CATACGCCCGAGATTTTTGGCTATTATCAATGAAGGTAATACAATATA
TTTTCGAAGAATTG
```

FIG. 27-4

```
ATTGAGTTATTAACATGTAACCTCTTATTATTTGCGCAAAAGGAATGGT
ATCCCAGGCTTCTGCTATCTCTATCCGTGCTTTTTCCTTTCTTTTGTTC
TCCCCTTTTTTGTCCTTTTCCTTTTTCTCTTCTCTTTTTGTTTGTTCTT
CTCTAGACTCTAGAATCTTGAATTCGGTACCCTCTAGTCAAGGCCTTAA
GTGAGTCGTATTACGGACTGGCCGTCGTTTTACAACGTCGTGACTGGGA
AAACCCTGGCGTTACCCAACTTAATCGCCTTGCAGCACATCCCCCTTTC
GCCAGCTGGCGTAATAGCGAAGAGGCCCGCACCGATCGCCCTTCCCAAC
AGTTGCGCAGCCTGAATGGCGAATGGCGCTTCGCTTGGTAATAAAGCCC
GCTTCGGCGGGCTTTTTTTT
```

FIG. 28-1

```
GTTAACTACGTCAGGTGGCACTTTTCGGGGAAATGTGCGCGGAACC
CCTATTTGTTTATTTTTCTAAATACATTCAAATATGTATCCGCTCA
TGAGACAATAACCCTGATAAATGCTTCAATAATATTGAAAAAGGAA
GAGTATGAGTATTCAACATTTCCGTGTCGCCCTTATTCCCTTTTTT
GCGGCATTTTGCCTTCCTGTTTTTGCTCACCCAGAAACGCTGGTGA
AAGTAAAAGATGCTGAAGATCAGTTGGGTGCACGAGTGGGTTACAT
CGAACTGGATCTCAACAGCGGTAAGATCCTTGAGAGTTTTCGCCCC
GAAGAACGTTCTCCAATGATGAGCACTTTTAAAGTTCTGCTATGTG
GCGCGGTATTATCCCGTGTTGACGCCGGGCAAGAGCAACTCGGTCG
CCGCATACACTATTCTCAGAATGACTTGGTTGAGTACTCACCAGTC
ACAGAAAAGCATCTTACGGATGGCATGACAGTAAGAGAATTATGCA
GTGCTGCCATAACCATGAGTGATAACACTGCGGCCAACTTACTTCT
GACAACGATCGGAGGACCGAAGGAGCTAACCGCTTTTTTGCACAAC
ATGGGGGATCATGTAACTCGCCTTGATCGTTGGGAACCGGAGCTGA
ATGAAGCCATACCAAACGACGAGCGTGACACCACGATGCCTGTAGC
AATGGCAACAACGTTGCGCAAACTATTAACTGGCGAACTACTTACT
CTAGCTTCCCGGCAACAATTAATAGACTGGATGGAGGCGGATAAAG
TTGCAGGACCACTTCTGCGCTCGGCCCTTCCGGCTGGCTGGTTTAT
TGCTGATAAATCTGGAGCCGGTGAGCGTGGGTCTCGCGGTATCATT
GCAGCACTGGGGCCAGATGGTAAGCCCTCCCGTATCGTAGTTATCT
ACACGACGGGGAGTCAGGCAACTATGGATGAACGAAATAGACAGAT
CGCTGAGATAGGTGCCTCACTGATTAAGCATTGGTAACTGTCAGAC
CAAGTTTACTCATATATACTTTAGATTGATTTACCCCGGTTGATAA
TCAGAAAAGCCCCAAAAACAGGAAGATTGTATAAGCAAATATTTAA
ATTGTAAACGTTAATATTTTGTTAAAATTCGCGTTAAATTTTTGTT
AAATCAGCTCATTTTTTAACCAATAGGCCGAAATCGGCAAAATCCC
TTATAAATCAAAAGAATAGCCCGAGATAGGGTTGAGTGTTGTTCCA
GTTTGGAACAAGAGTCCACTATTAAAGAACGTGGACTCCAACGTCA
AAGGGCGAAAAACCGTCTATCAGGGCGATGGCCCACTACGTGAACC
ATCACCCAAATCAAGTTTTTTGGGGTCGAGGTGCCGTAAAGCACTA
AATCGGAACCCTAAAGGGAGCCCCCGATTTAGAGCTTGACGGGGAA
AGCGAACGTGGCGAGAAAGGAAGGGAAGAAAGCGAAAGGAGCGGGC
GCTAGGGCGCTGGCAAGTGTAGCGGTCACGCTGCGCGTAACCACCA
CACCCGCCGCGCTTAATGCGCCGCTACAGGGCGCGTAAAAGGATCT
AGGTGAAGATCCTTTTTGATAATCTCATGACCAAAATCCCTTAACG
TGAGTTTTCGTTCCACTGAGCGTCAGACCCCGTAGAAAAGATCAAA
GGATCTTCTTGAGATCCTTTTTTTCTGCGCGTAATCTGCTGCTTGC
AAACAAAAAAACCACCGCTACCAGCGGTGGTTTGTTTGCCGGATCA
AGAGCTACCAACTCTTTTTCCGAAGGTAACTGGCTTCAGCAGAGCG
CAGATACCAAATACTGTTCTTCTAGTGTAGCCGTAGTTAGGCCACC
ACTTCAAGAACTCTGTAGCACCGCCTACATACCTCGCTCTGCTAAT
CCTGTTAC
```

FIG. 28-2

```
CAGTGGCTGCTGCCAGTGGCGATAAGTCGTGTCTTACCGGGTTGGA
CTCAAGACGATAGTTACCGGATAAGGCGCAGCGGTCGGGCTGAACG
GGGGGTTCGTGCACACAGCCCAGCTTGGAGCGAACGACCTACACCG
AACTGAGATACCTACAGCGTGAGCTATGAGAAAGCGCCACGCTTCC
CGAAGGGAGAAAGGCGGACAGGTATCCGGTAAGCGGCAGGGTCGGA
ACAGGAGAGCGCACGAGGGAGCTTCCAGGGGGAAACGCCTGGTATC
TTTATAGTCCTGTCGGGTTTCGCCACCTCTGACTTGAGCGTCGATT
TTTGTGATGCTCGTCAGGGGGCGGAGCCTATGGAAAAACGCCAGC
AACGCGGCCTTTTTACGGTTCCTGGCCTTTTGCTGGCCTTTTGCTC
ACATGTAATGTGAGTTAGCTCACTCATTAGGCACCCCAGGCTTTAC
ACTTTATGCTTCCGGCTCGTATGTTGTGTGGAATTGTGAGCGGATA
ACAATTTCACACAGGAAACAGCTATGACCATGATTACGCCAAGCTA
CGTAATACGACTCACTAGTGGGCAGATCTTCGAATGCATCGCGCGC
AATTCACCGCCGTATGGCTGACCGGCGATTACTAGCGATTCCGGCT
TCATGCAGGCGAGTTGCAGCCTGCAATCCGAACTGAGGACGGGTTT
TTGGGGTTAGCTCACCCTCGCGGGATCGCGACCCTTTGTCCCGGCC
ATTGTAGCACGTGTGTCGCCCAGGGCATAAGGGGCATGATGACTTG
ACGTCATCCTCACCTTCCTCCGGCTTATCACCGGCAGTCTGTTCAG
GGTTCCAAACTCAACGATGGCAACTAAACACGAGGGTTGCGCTCGT
TGCGGGACTTAACCCAACACCTTACGGCACGAGCTGACGACAGCCA
TGCACCACCTGTGTCCGCGTTCCCGAAGGCACCCCTCTCTTTCAAG
AGGATTCGCGGCATGTCAAGCCCTGGTAAGGTTCTTCGCTTTGCAT
CGAATTAAACCACATGCTCCACCGCTTGTGCGGGCCCCCGTCAATT
CCTTTGAGTTTCATTCTTGCGAACGTACTCCCCAGGCGGGATACTT
AACGCGTTAGCTACAGCACTGCACGGGTCGATACGCACAGCGCCTA
GTATCCATCGTTTACGGCTAGGACTACTGGGGTATCTAATCCCATT
CGCTCCCCTAGCTTTCGTCTCTCAGTGTCAGTGTCGGCCCAGCAGA
GTGCTTTCGCCGTTGGTGTTCTTTCCGATCTCTACGCATTTCACCG
CTCCACCGGAAATTCCCTCTGCCCCTACCGTACTCCAGCTTGGTAG
TTTCCACCGCCTGTCCAGGGTTGAGCCCTGGGATTTGACGGCGGAC
TTAAAAAGCCACCTACAGACGCTTTACGCCCAATCATTCCGGATAA
CGCTTGCATCCTCTGTATTACCGCGGCTGCTGGCACAGAGTTAGCC
GATGCTTATTCCCAGATACCGTCATTGCTTCTTCTCCGGGAAAAG
AAGTTCACGACCCGTGGGCCTTCTACCTCCACGCGGCATTGCTCCG
TCAGCTTTCGCCCATTGCGGAAAATTCCCCACTGCTGCCTCCCGTA
GGAGTCTGGGCCGTGTCTCAGTCCCAGTGTGGCTGATCATCCTCTC
GGACCAGCTACTGATCATCGCCTTGGTAAGCTATTGCCTCACCAAC
TAGCTAATCAGACGCGAGCCCCTCCTCGGGCGGATTCCTCCTTTTG
CTCCTCAGCCTACGGGGTATTAGCAGCCGTTTCCAGCTGTTGTTCC
CCTCCCAAGGGCAGGTTCTTACGCGTTACTCACCCGTCCGCCACTG
GAAACACCACTTCCCGTCCGACTTGCATGTGTTAAGC
```

FIG. 28-3

```
ATGCCGCCAGCGTTCATCCTGAGCCAGGATCGAACTCTCCATGAGAT
TCATAGTTGCATTACTTATAGCTTCCTTGTTCGTAGACAAAGCGGAT
TCGGAATTGTCTTTCATTCCAAGGCATAACTTGTATCCATGCGCTTC
ATATTCGCCCGGAGTTCGCTCCCAGAAATATAGCCATCCCTGCCCCC
TCACGTCAATCCCACGAGCCTCTTATCCATTCTCATTGAACGACGGC
GGGGGAGCAAATCCAACTAGAAAAACTCACATTGGGCTTAGGGATAA
TCAGGCTCGAACTGATGACTTCCACCACGTCAAGGTGACACTCTACC
GCTGAGTTATATCCCTTCCCCGCCCCATCGAGAAATAGAACTGACTA
ATCCTAAGTCAAAGGCGTACGagaatactcaatCATGAATAAATGCA
AGAAAATAACCTCTCCTTCTTTTTTCTATAATGTAAACAAAAAAGTCT
ATGTAAGTAAAATACTAGTAAATAAATAAAAAGAAAAAAAGAAAGGA
GCAATAGCACCCTCTTGATAGAACAAGAAAATGATTATTGCTCCTTT
CTTTTCAAAACCTCCTATAGACTAGGCCAGGATCCTCGAGcttaatt
aaGGTAAAATCTTGGTTTATTTAATCATCAGGGACTCCCAAGCACAC
TAGTTTTCTACAAATCAAAATAGAAAATAGAAAATGGAAGGCTTTTT
ATTCAACAGTATAACATGACTTATATACTCGTGTCAACCAAGGTGTA
TGTAGATCtattcCTGCAGGATATCTGGATCCACGAAGCTTCCCATG
GGAATAGATCTACATACACCTTGGTTGACACGAGTATATAAGTCATG
TTATACTGTTGAATAAAAAGCCTTCCATTTTCTATTTTGATTTGTAG
AAAACTAGTGTGCTTGGGAGTCCCTGATGATTAAATAAACCAAGATT
TTACCGTTTAAACACCGGTGATCCTGGCCTAGTCTATAGGAGGTTTT
GAAAAGAAAGGAGCAATAATCATTTTCTTGTTCTATCAAGAGGGTGC
TATTGCTCCTTTCTTTTTTTCTTTTTATTTATTTACTAGTATTTTAC
TTACATAGACTTTTTTGTTTACATTATAGAAAAAGAAGGAGAGGTTA
TTTTCTTGCATTTATTCATGATTGAGTATTCTcctaggGTCGAGAAA
CTCAACGCCACTATTCTTGAACAACTTGGAGCCGGGCCTTCTTTTCG
CACTATTACGGATATGAAAATAATGGTCAAAATCGGATTCAATTGTC
AACTGCCCCTATCGGAAATAGGATTGACTACCGATTCCGAAGGAACT
GGAGTTACATCTCTTTTCCATTCAAGAGTTCTTATGCGTTTCCACGC
CCCTTTGAGACCCCGAAAAATGGACAAATTCCTTTTCTTAGGAACAC
ATACAAGATTCGTCACTACAAAAAGGATAATGGTAACCCTACCATTA
ACTACTTCATTTATGAATTTCATAGTAATAGAAATACATGTCCTACC
GAGACAGAATTTGGAACTTGCTATCCTCTTGCCTAGCAGGCAAAGAT
TTACCTCCGTGGAAAGGATGATTCATTCGGATCGACATGAGAGTCCA
ACTACATTGCCAGAATCCATGTTGTATATTTGAAAGAGGTTGACCTC
CTTGCTTCTCTCATGGTACACTCCTCTTCCCGCCGAGCCCCTTTTCT
CCTCGGTCCACAGAGACAAAATGTAGGACTGGTGCCAACAATTCATC
AGACTCACTAAGTCGGGATCACTAACTAATACTAATCTAATATAATA
GTCTAATATATCTAATATAATAGAAAATACTAATATAATAGAAAAGA
ACTGTCTTTTCTGTATACTTTCCCCGGTTCCGTTGCTACCGCGGGCT
TTACGCAATCGATCGGATTAGATAGATATCCCTTCAACATAGGTCAT
CGA
```

FIG. 2B-4

```
AAGGATCTCGGAGACCCACCAAAGTACGAAAGCCAGGATCTTTCAG
AAAACGGATTCCTATTCAAAGAGTGCATAACCGCATGGATAAGCTC
ACACTAACCCGTCAATTTGGGATCCAAATTCGAGATTTTCCTTGGG
AGGTATCGGGAAGGATTTGGAATGGAATAATATCGATTCATACAGA
AGAAAAGGTTCTCTATTGATTCAAACACTGTACCTAACCTATGGGA
TAGGGATCGAGGAAGGGGAAAAACCGAAGATTTCACATGGTACTTT
TATCAATCTGATTTATTTCGTACCTTTCGTTCAATGAGAAAATGGG
TCAAATTCTACAGGATCAAACCTATGGGACTTAAGGAATGATATAA
AAAAAAGAGAGGGAAAATATTCATATTAAATAAATATGAAGTAGAA
GAACCCAGATTCCAAATGAACAAATTCAAACTTGAAAAGGATCTTC
CTTATTCTTGAAGAATGAGGGGCAAAGGGATTGATCAAGAAAGATC
TTTTGTTCTTCTTATATATAAGATCGTGATGGTACCCTCTAGTCAA
GGCCTTAAGTGAGTCGTATTACGGACTGGCCGTCGTTTTACAACGT
CGTGACTGGGAAAACCCTGGCGTTACCCAACTTAATCGCCTTGCAG
CACATCCCCCTTTCGCCAGCTGGCGTAATAGCGAAGAGGCCCGCAC
CGATCGCCCTTCCCAACAGTTGCGCAGCCTGAATGGCGAATGGCGC
TTCGCTTGGTAATAAAGCCCGCTTCGGCGGGCTTTTTTTT
```

METHOD FOR GENERATING SPLIT, NON-TRANSFERABLE GENES THAT ARE ABLE TO EXPRESS AN ACTIVE PROTEIN PRODUCT

This application is a 371 of PCT/US00/14122 filed May 23, 2000, which claims the benefit of U.S. Provisional Application No. 60/135,677, filed May 24, 1999.

BACKGROUND OF THE INVENTION

In the past few years, agriculture in the United States has been revolutionized by the introduction of transgenic crops that are resistant to specific diseases, insects, herbicides or have improved nutritional value. At the same time, much concern has been expressed around the world that these genetically modified (GM) agricultural products may be harmful to the consumer and that the transgenes could be transferred to related plant species so as to generate insect- or herbicide-resistant "superweeds" (Ferber, D., *Science* 286:1662 (1999)) or consumed by other organisms to their detriment (Losey, et al., *Nature* 399:214 (1999)). Whereas there is little scientific basis to the fear of harmful effects of "GM foods", the possibility that transgenes are transferred to other plants and thereby have an adverse ecological impact is not entirely unfounded (Bergelson, et al., *Nature* 395:25 (1998)). Such transfer could occur either by pollination of closely related species or by the transfer of gene fragments to unrelated plants by viral or plasmid vectors whose transmission may be mediated by plant-associated fungi, bacteria or insects.

There have been a number of techniques discussed for the prevention of transgene spread, however these procedures either are designed to have a negative impact on the new hybrid plant (Gressel, *Trends Biotechnol.*, 17:361–366 (1999)), as in the case of tandem constructs or will not eliminate the possiblity of spread by horizontal gene transfer (Bertolla and Simonet, *Res. Microbiol.*, 150:375–384 (1999)).

In this disclosure, we propose a new type of transgene that allows efficient protein expression but does not require a gene coupling approach and has a significantly lower chance of spread by horizontal gene transfer.

SUMMARY OF THE INVENTION

In accordance with the present invention, there is disclosed a new type of transgene system that allows efficient protein expression in a target host such as a plant, but avoids the undesirable result of the migration of the transgene into related host systems and/or to the environment via the pollen. The methods described herein can also be applied to the expression of virtually any protein of interest (e.g. a toxic protein) in eukaryotic (yeast, insect, mammalian cells, etc.) and prokaryotic (*E. coli*, etc.) organisms.

In each case, the target gene is split into at least two segments, each can be fused to a portion of an intein coding sequence. Each fusion gene is expressed as an inactive protein and these separately expressed fusion proteins are reassembled into an active form. Compartmentalization of the gene fragments allows the target protein to be reconstituted in a desired location and can prevent the transmission of a functional gene to other organisms.

It should be noted that although the present invention is specifically exemplified in agriculture and plant biotechnology, the approach proposed here has a much broader scope and can be applied to any gene expressed in any organism for the prevention of its accidental transfer to another organism.

DESCRIPTION OF THE DRAWINGS

FIG. 2—Trans-Splicing.

FIG. 6—Sequence alignment for acetolactate synthase (ALS) genes (SEQ ID NO:42, SEQ ID NO:43, SEQ ID NO:44, SEQ ID NO:45 and SEQ ID NO:46). The gap region for E. coli acetolactate synthase II (ALSII) is underlined. The arrow indicates the split site for E. coli ALSII. The star indicates the split site for maize ALS.

FIG. 9—Assays for acetolactate synthase II (ALSII) Activity.

The activity of each 5-enolpyruvyl-3-phosphoshikimate synthetase (EPSPS) trans-splicing construct was assayed by co-transforming the matching constructs into E. coli ER2799 cells and plating on an M9 selection plate. pCYB3 or pKYB1 (New England Biolabs, Inc., Beverly, Mass.), which has no EPSPS gene present, was used to provide ampicillin or kanamycin resistance when testing the activity of each half of the EPSPS gene.

The plasmids used were: pC+E2, which contains the full length EPSPS mutant gene; p215EN2, which has the first 215 amino acids of EPSPS fused to the N-terminal splicing domain of the Ssp DnaE intein; p235EN2, which has the first 235 amino acids of EPSPS fused to the N-terminal splicing domain of the Ssp DnaE intein; pEPS#28, which contains amino acids 216–427 of the EPSPS gene fused to the C-terminal splicing domain of the Ssp DnaE intein; pEPS#29, which contains amino acids 236–427 of the EPSPS gene fused to the C-terminal splicing domain of the Ssp DnaE intein; pEPS#33, which has the first 235 amino acids of EPSPS fused to a splicing defective N-terminal domain of the Ssp DnaE intein; pEPS#37, which has amino acids 236–427 of EPSPS fused to a splicing defective C-terminal domain of the Ssp DnaE intein; pEPS#34, which has the first 235 amino acids of EPSPS, but no intein fragment; and pEPS#36, which has amino acids 236–427 of EPSPS and no intein fragment. These plasmids were co-transformed, in various combinations, into ER2799 E. coli cells, and plated-on both LB plates and M9 plates, each plate was supplemented with 100 μg/mL ampicillin and 50 μg/mL kanamycin and 0.3 mM IPTG. Individual clones were picked from each LB plate and stripped on one M9 selection plate following incubation at 37° C. overnight or RT for 2–3 days. The M9 minimal media selection plate contained 100 μg/mL ampicillin and 50 μg/mL kanamycin and 0.3 mM IPTG. The combinations used were: WT, pC+E2 and pKYB; 215NC, p215EN2 and pEPS#28; 215C, pEPS#28 and pCYB3; 235NC-Dead, pEPS#33 and pEPS#37; 235NC, p235EN2 and pEPS#29; 235N, p235EN2 and pKYB1; 235C, pEPS#29 and pCYB3; 235N-215C, p235EN2 and pEPS#28; and 235 complement, pEPS#34 and pEPS#36.

Figure 12:
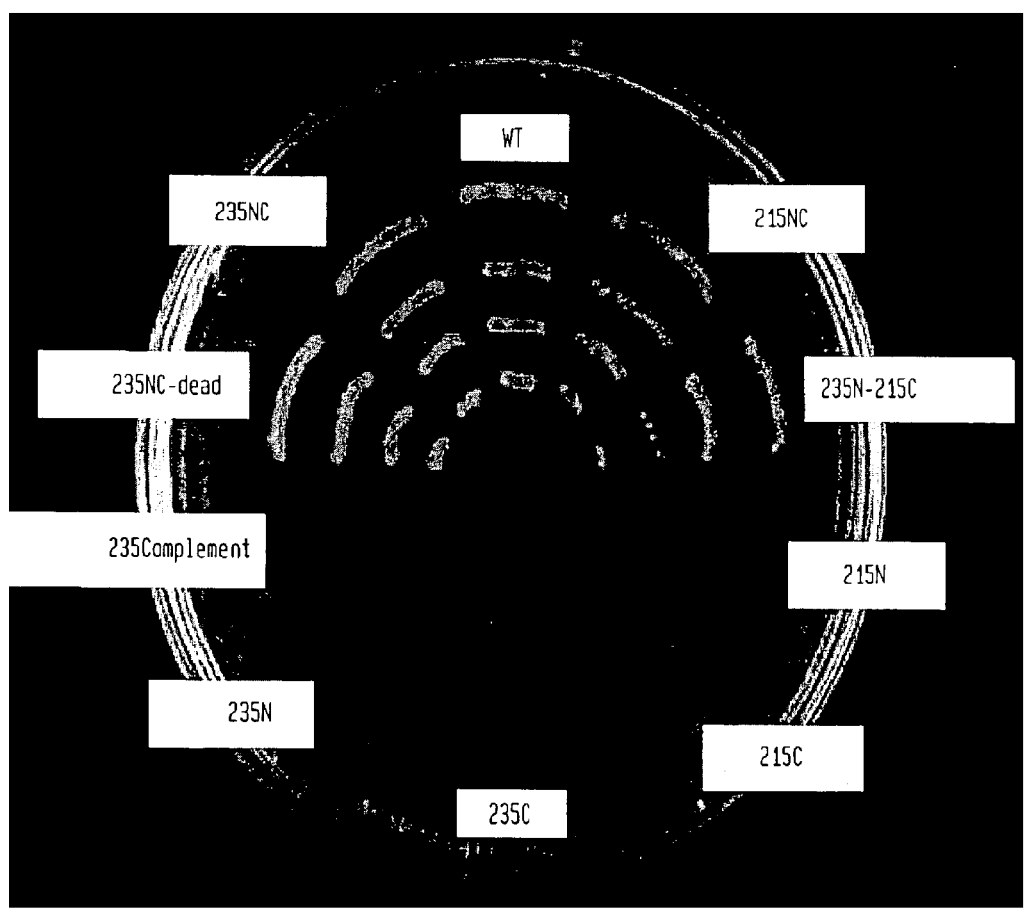
FIG. 12—Plating Assay for the Ssp DnaE intein Trans-splicing Constructs at Positions 215 and 235.
Figure 13A:
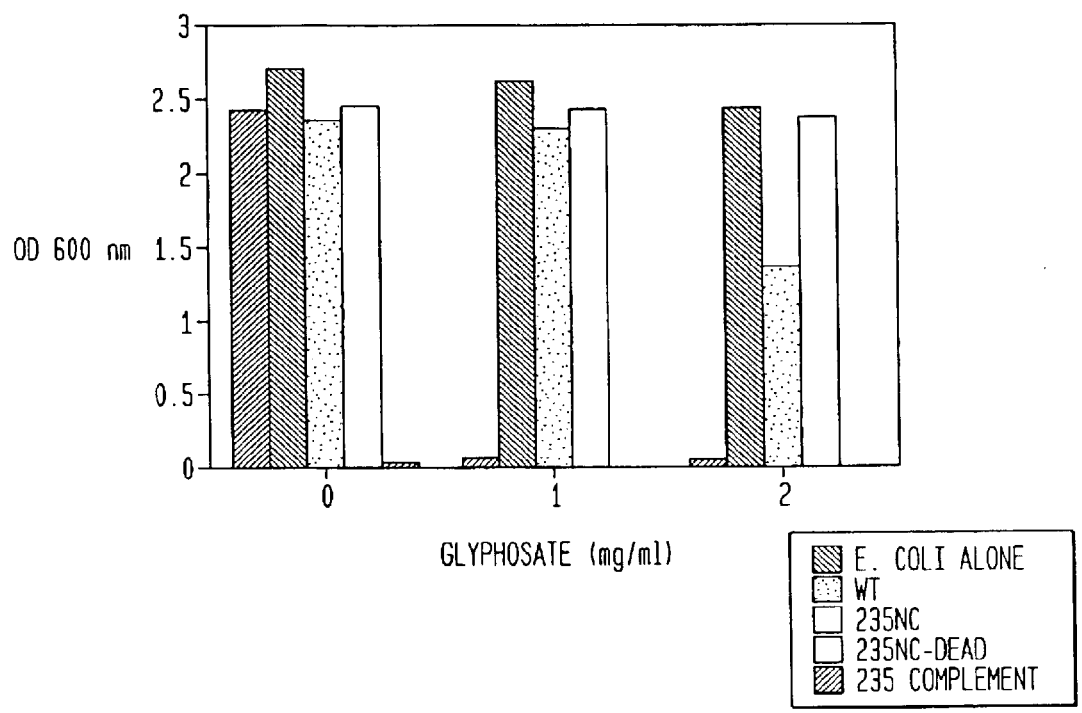
Figure 13B:
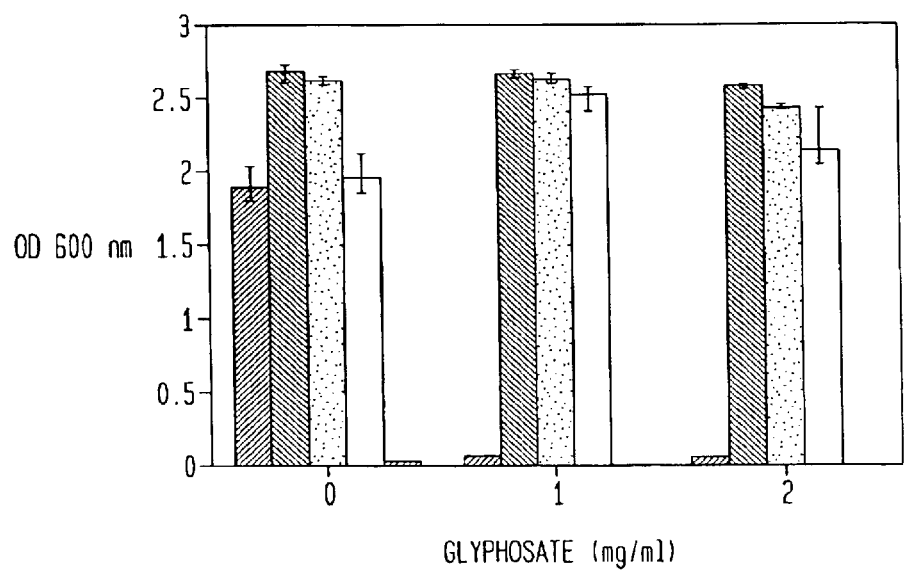

FIG. 13—Glyphosate Resistance Liquid Assay for 235 Trans-splicing Constructs. The plasmid constructs were as described in FIG. 12. The combinations used were: WT, pC+E2 and pKYB; 235NC-Dead, pEPS#33 and pEPS#37; 235NC, p235EN2 and pEPS#29; 235N, p235EN2 and pKYB1; 235C, pEPS#29 and pCYB3; and 235 complement, pEPS#34 and pEPS#36. These plasmids were co-transformed into ER2799 E. coli cells and plated on LB plates, supplemented with 100 μg/mL ampicillin and 50 μg/mL kanamycin; pCYB3/pKYB were co-transformed into E. coli ER2744, and plated on the LB plate, supplemented as described previously. A preculture was prepared for each transformation by inoculating the fresh colony into LB medium containing 100 μg/mL ampicillin and 50 μg/mL kanamycin at 30° C. for overnight. Equal amounts of pre-culture (10–11 μL depending on the cell density) was inoculated into freshly-made M9 minimal medium containing 100 μg/ml of ampicillin, 50 μg/ml of kanamycin and 0.3 mM IPTG in the absence or presence of different amounts of glyphosate. The growth of each construct was measured by OD at 600 nm. FIG. 13A, growth at 37° C. FIG. 13B, growth at 30° C.

Figure 14:
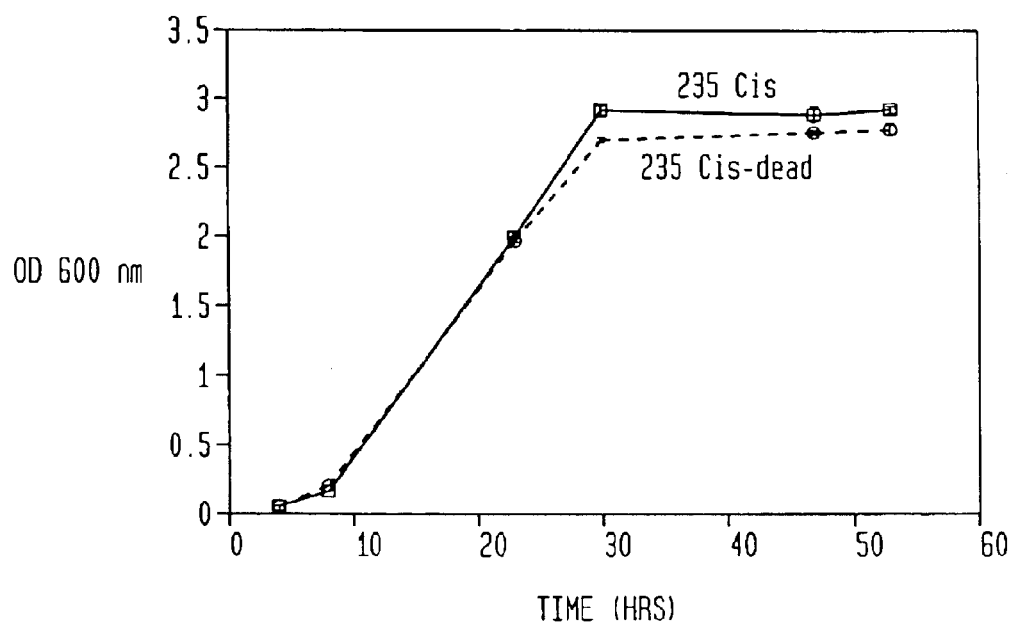

FIG. 14—Growth of the cis-splicing 235 construct in M9 liquid minimal media. A plasmid with the full length Ssp DnaE intein inserted into position 235 of 5-enolpyruvyl-3-phosphoshikimate synthetase (EPSPS) was constructed. Two plasmid vectors were created (pCE235 DnaE and pEPS#31), one with a splicing competent Ssp DnaE intein (235 cis) and another with a splicing incompetent intein (235 dead). These plasmids were co-transformed with pKEB12 into ER2799 E. coli cells and plated on LB plates supplemented with 100 μg/mL ampicillin and 50 μg/mL kanamycin. A preculture was prepared for each transformation by inoculating the fresh colony into LB medium at 30° C. for overnight. Equal amounts of pre-culture (10–11 μL depending on the cell density) was inoculated into freshly-made M9 minimal medium containing 100 μg/ml of ampicillin, 50 μg/ml of kanamycin and 0.3 mM IPTG. The cell density was determined at various times using the OD at 600 nm.

FIG. 15 is a table that shows the sites in the 5-enolpyruvyl-3-phosphoshikimate synthetase (EPSPS) protein that allow a 5 amino acid insertion and still result in active protein.

FIG. 16 is a table that shows the sites in the 5-enolpyruvyl-3-phosphoshikimate synthetase (EPSPS) protein where a 5 amino acid insertion results in inactive protein.

Figure 17:
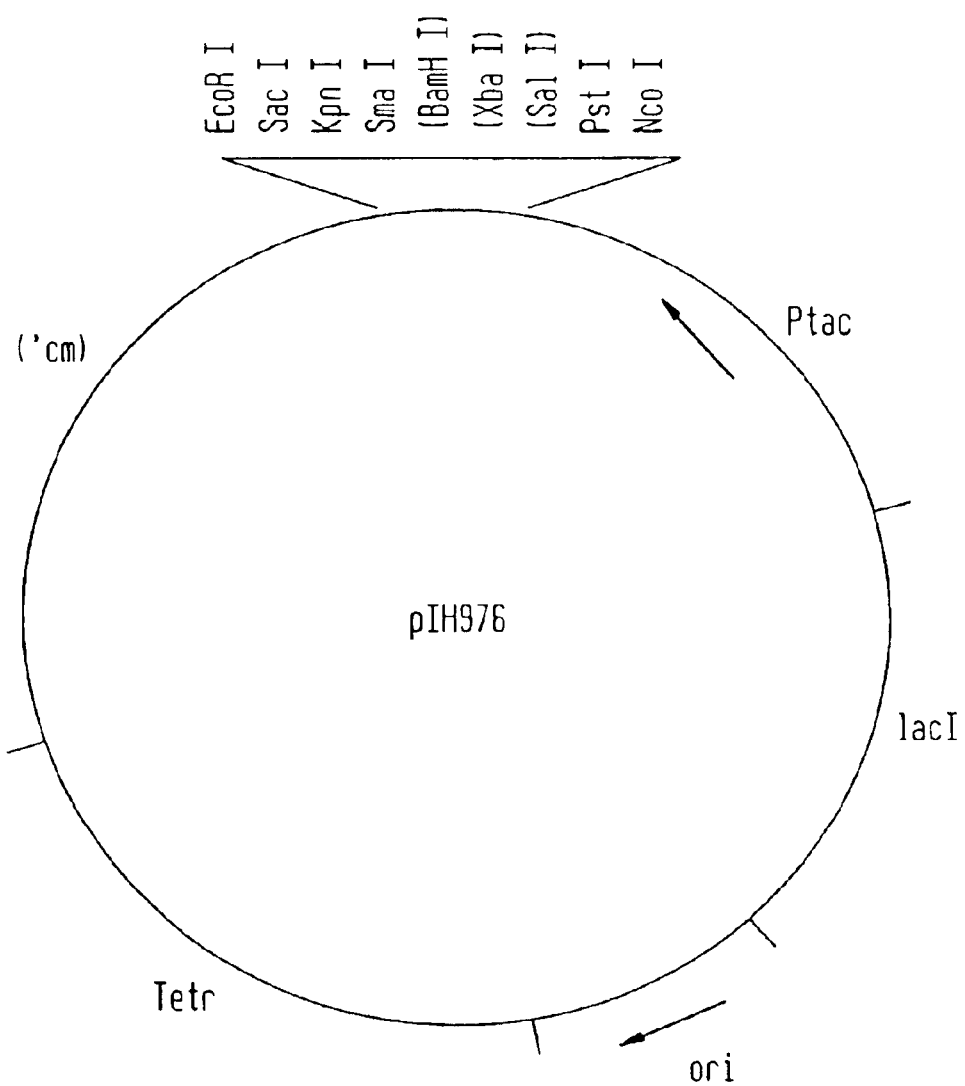

FIG. 17 is a map of pIH976. Circular double stranded DNA with a multiple cloning site. The restriction enzyme sites are indicated. Restriction sites with parenthesis are not unique. Ptac represents tac promoter. Origin of replication is ori. This plasmid has tetracyclin drug resistant marker (Tetr).

FIG. 18 is a map of pAGR3. Circular double stranded DNA (SEQ ID NO:76) with a multiple cloning site. The restriction enzyme sites are indicated below. Ptac represents Tac promoter. Origin of replication is ori. This plasmid has ampicillin drug resistant marker (ampr). Lac operator and ribosome binding sites are indicated. Plasmid pAGR3 is an expression vector which includes several elements: (1) a synthetic tac promoter coupled to a symmetric synthetic lac operator sequence; (2) a lac ribosome binding site; (3) a polylinker for cloning with the ATG within the NcoI site being about seven nucleotides downstream of the ribosome binding site; (4) a copy of the lacI$^Q$ gene to provide repression of the tac promoter; (5) the replication origin from pBR322; (6) ampicillin resistance gene; and (7) a four-fold copy of the ribosomal transcription terminator upstream of the tac promoter. The transcription terminators lower the basal level of transcription by reducing read-through transcription from upstream promoters.

FIG. 19 Trans-splicing of two unrelated gene products in E. coli using the Ssp DnaE intein as splice element.

Figure 19A:
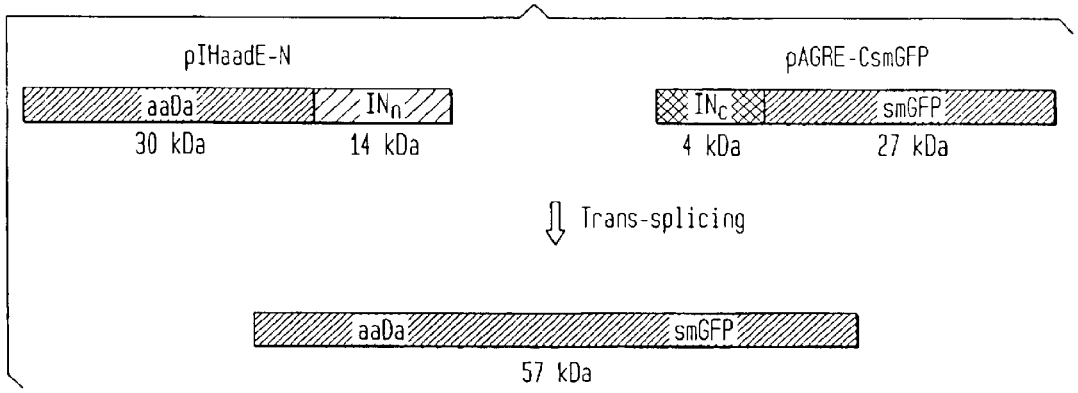

FIG. 19A Plasmid pIHaadE-N represents aadA gene (in black) fused to the N-terminal splicing domain of the Ssp DnaE Intein (IN$_n$ in grey). Plasmid pAGRE-CsmGFP plasmid represents the C-terminal splicing domain of the Ssp DnaE intein (IN$_c$ in grey) and smGFP (in black). The calculated molecular mass for each of the partners is indicated below in kDa. The arrow indicates a trans-splicing event resulting in a aadA-smGFP (57 kDa) fusion protein.

Figure 19B:
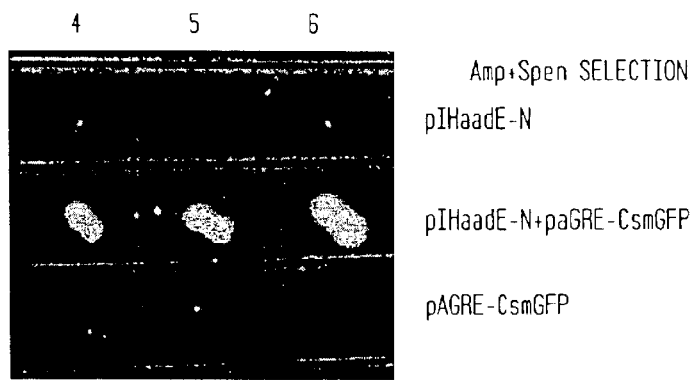

FIG. 19B Ampicillin and spectinomycin sulphate selection of pIHaadE-N and pAGRE-CsmGFP plasmid in E. coli cells. E. coli were transformed with the plasmids indicated on the right side. Colony numbers are indicated on top.

Figure 19C:
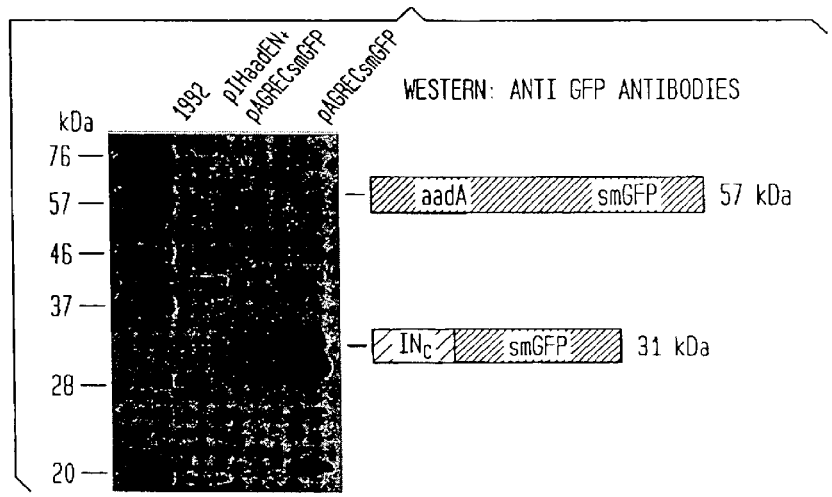

FIG. 19C Expression and detection of hybrid aadA-smGFP protein through trans-splicing. Western blot analysis of E. coli cell extracts expressing the constructs as indicated above the figure, using a monoclonal smGFP specific antibody. The relative positions of biotinylated MW markers (76, 57, 46, 37, 28 and 20) are in kDa. The protein bands corresponding to aadA-smGFP hybrid as well as IN$_c$-smGFP are indicated.

Figure 20:
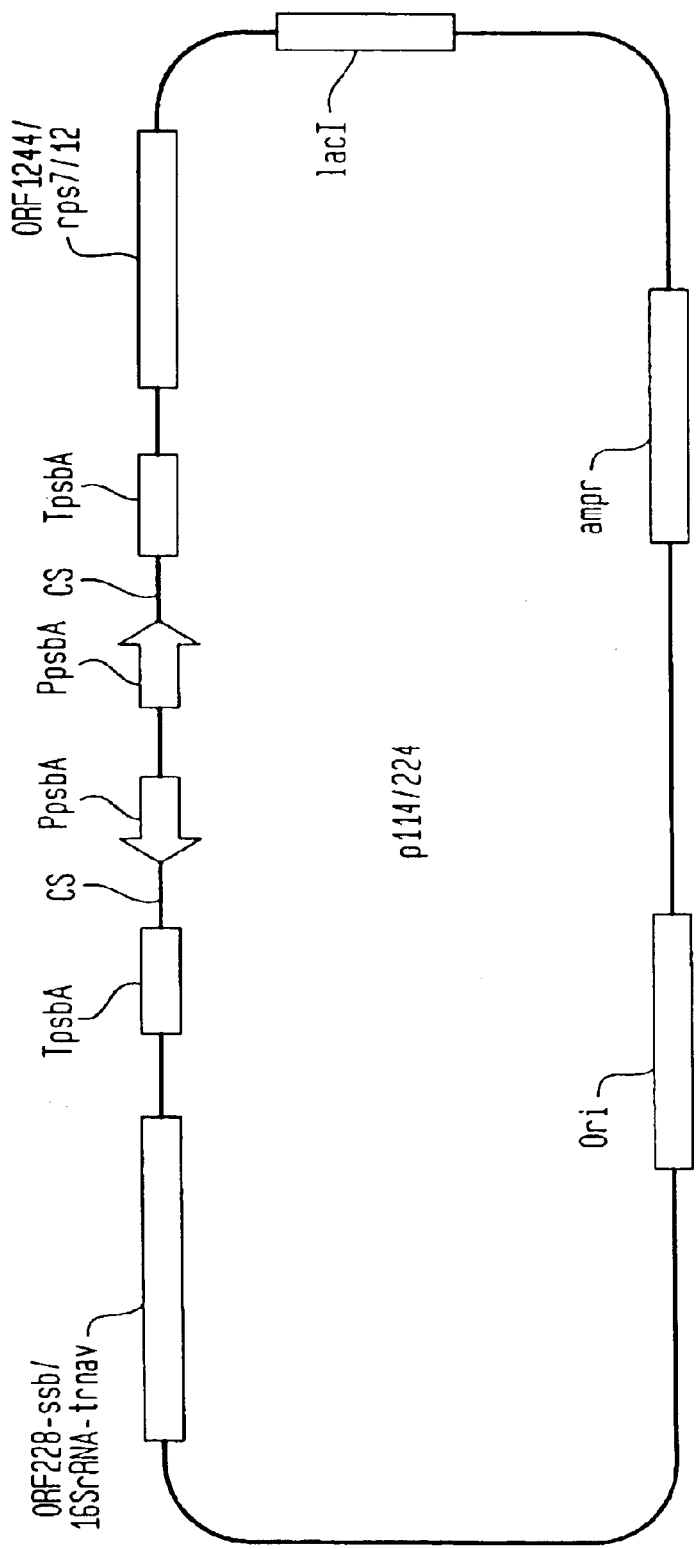

FIG. 20 is a map of pNCT114/224. Circular double stranded DNA with a multiple cloning site capable of targeting gene/(s) to predetermined locus. The restriction enzyme sites are indicated. PpsbA and TpsbA represents photosynthetic polypeptide D1 gene promoter and terminator respectively. Origin of replication is ori. This plasmid has ampicillin drug resistant marker (ampr). The homologous recombination sequences are indicated as left border (orf228-ssb for pNCT114 and 16SrDNA-trnaV for pNCT224) and right boarder (orfl244 for pNCT114 and rps7/12for pNCT224). CS represents the cloning sites.

FIG. 21 Plant promoter PpsbA activity in E. coli and Trans-splicing of aadA and smGFP.

FIG. 21A Plasmid p115ag/p225ag represents aadA gene (in black) fused to the Ssp DnaE intein N-terminal domain (IN$_n$ in grey) and the Ssp DnaE intein C-terminal domain (IN$_c$ in grey) fused to smGFP (in black). Both the hybrid genes are transcribed in opposite directions. The calculated molecular mass for each of the partner is indicated below in kDa. Arrow indicates a trans-splicing event resulting in a fused aadA-smGFP (57 kDa) protein.

FIG. 21B Ampicillin and spectinomycin sulphate selection of p115ag and p225ag plasmid in E. coli cells. E coli were transformed with the plasmids indicated on the right side. Colony identities are indicated on top. The digit after the plasmid is the isolate number. A plus symbol ("+") indicates the growth of the plasmid with the indicated antibiotics.

FIG. 21C Expression and detection of hybrid aadA-smGFP protein through trans-splicing. Western blot analysis of E. coli cell extracts expressing the constructs as indicated above the figure, using a monoclonal smGFP specific antibody. The relative positions of biotinylated MW markers are to the left in kDa. The protein bands corresponding to aad-smGFP hybrid as well as IN$_c$-smGFP are indicated.

Figure 22:
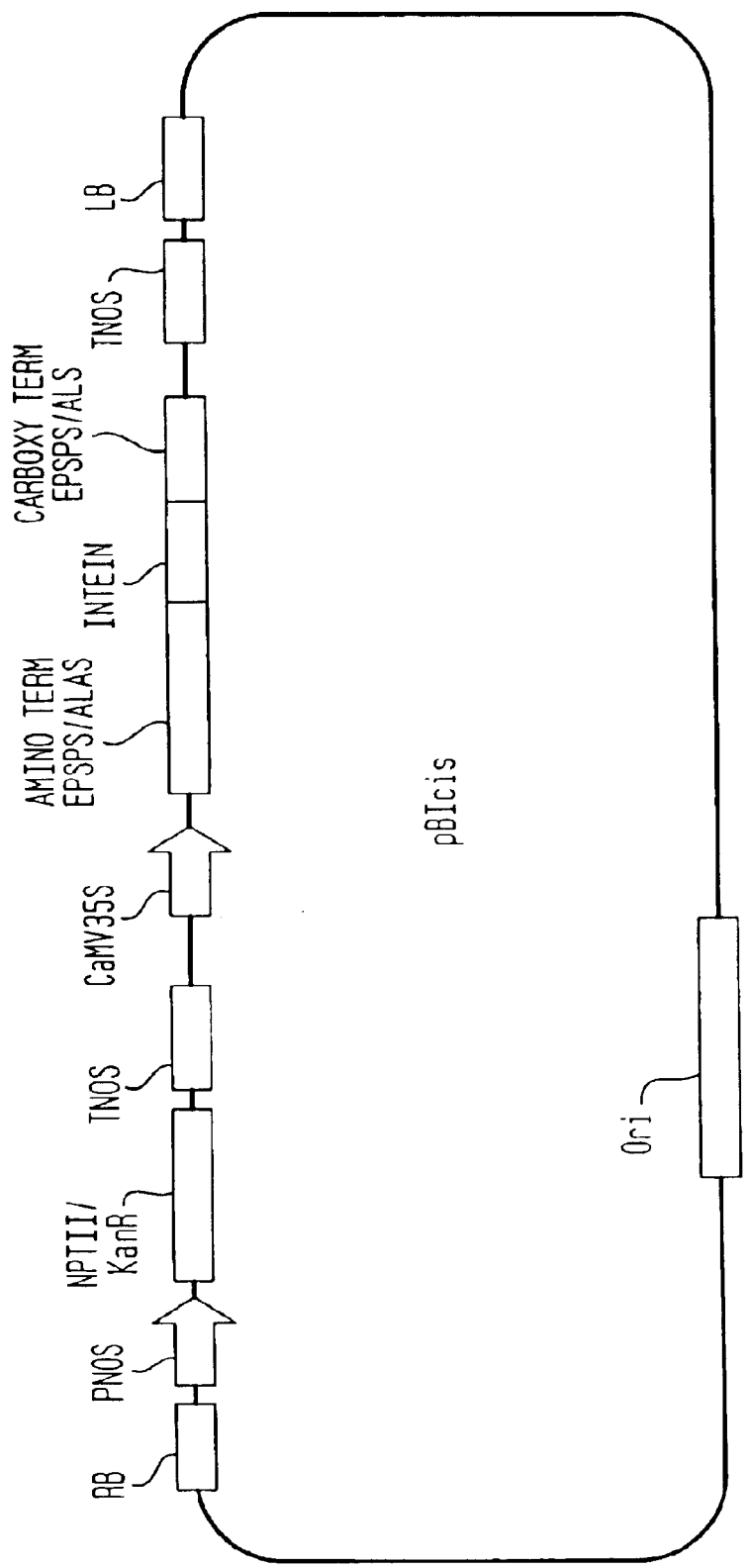

FIG. 22 Splicing in cis in plant cytoplasm. 5-enolpyruvyl-3-phosphoshikimate synthetase (EPSPS) and acetolactate synthase (ALS) genes are inserted in to the binary vector pBI121. The amino and carboxy terminal fragments of EPSPS or ALS are indicated in black. The Ssp DnaE intein (Intein) gene is flanked on either side by EPSPS/ALS fragment. Right and left boarder of the *Agrobacterium* is indicated as LB and RB. CaMV 35S promoter, NOS promoter (PNOS) and NOS terminator (TNOS) are indicated.

Figure 23:
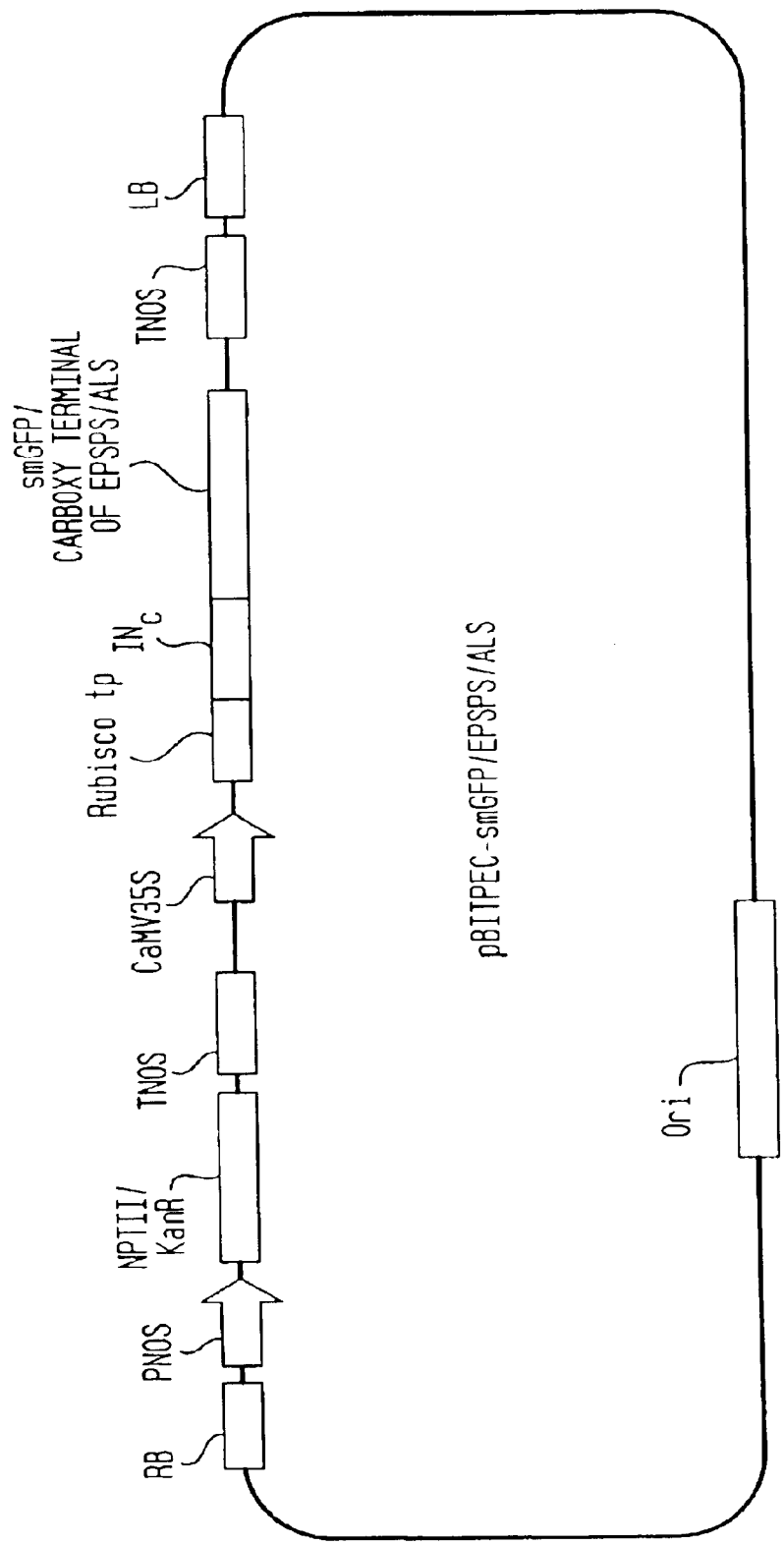

FIG. 23 Nuclear transfer vector pBITPEC or pBITPEC-smGFP. This binary vector has the CaMV35S promoter driving the rubisco3A transit peptide (TP) that is fused to the Ssp DnaE intein C-terminal splicing domain ($IN_c$). Genes to be cloned for organelle transport are indicated after $IN_c$. In case of pBITPECsmGFP the smGFP gene is cloned in to the multiple cloning site.

FIG. 24 is the psbA promoter (PpsbA) sequence (SEQ ID NO: 59).

FIG. 25 is the psbA terminator (TpsbA) (SEQ ID NO:60).

FIG. 26 is the Rubisco3 transit peptide (SEQ ID NO:61). Nucleotides in lower case represent codon optimized units.

FIG. 27 is the chloroplast gene targeting vector (pNCT114)(SEQ ID NO:62). Features of pNCT114 include: (1) vector backbone: pLITMUS28; (2) Inserted in BssHII to BsiWI the left border, (orf228-ssb, 1210 bp) chloroplast genome targeting fragment; (3) inserted in AvrII to KpnI the right border, (orf1244, 1550 bp) chloroplast genome targeting fragment; and (4) addition of PpsbA and TpsbA between BsiWI and PstI, whereas the other pair is between AvrII and NcoI site.

FIG. 28 is chloroplast gene targeting vector (pNCT224) (SEQ ID NO:63). Features of pNCT114 include: (1) vector backbone: pLITMUS28; (2) Inserted in BssHII to BsiWI the left border, (16SrDNA-trnaV, 1680 bp) chloroplast genome targeting fragment; (3) inserted in AvrII to KpnI the right border, (rps7/12, 1310 bp) chloroplast genome targeting fragment; and (4) addition of PpsbA and TpsbA between BsiWI and PstI, whereas the other pair is between AvrII and NcoI site.

DETAILED DESCRIPTION OF THE INVENTION

Figure 1A:
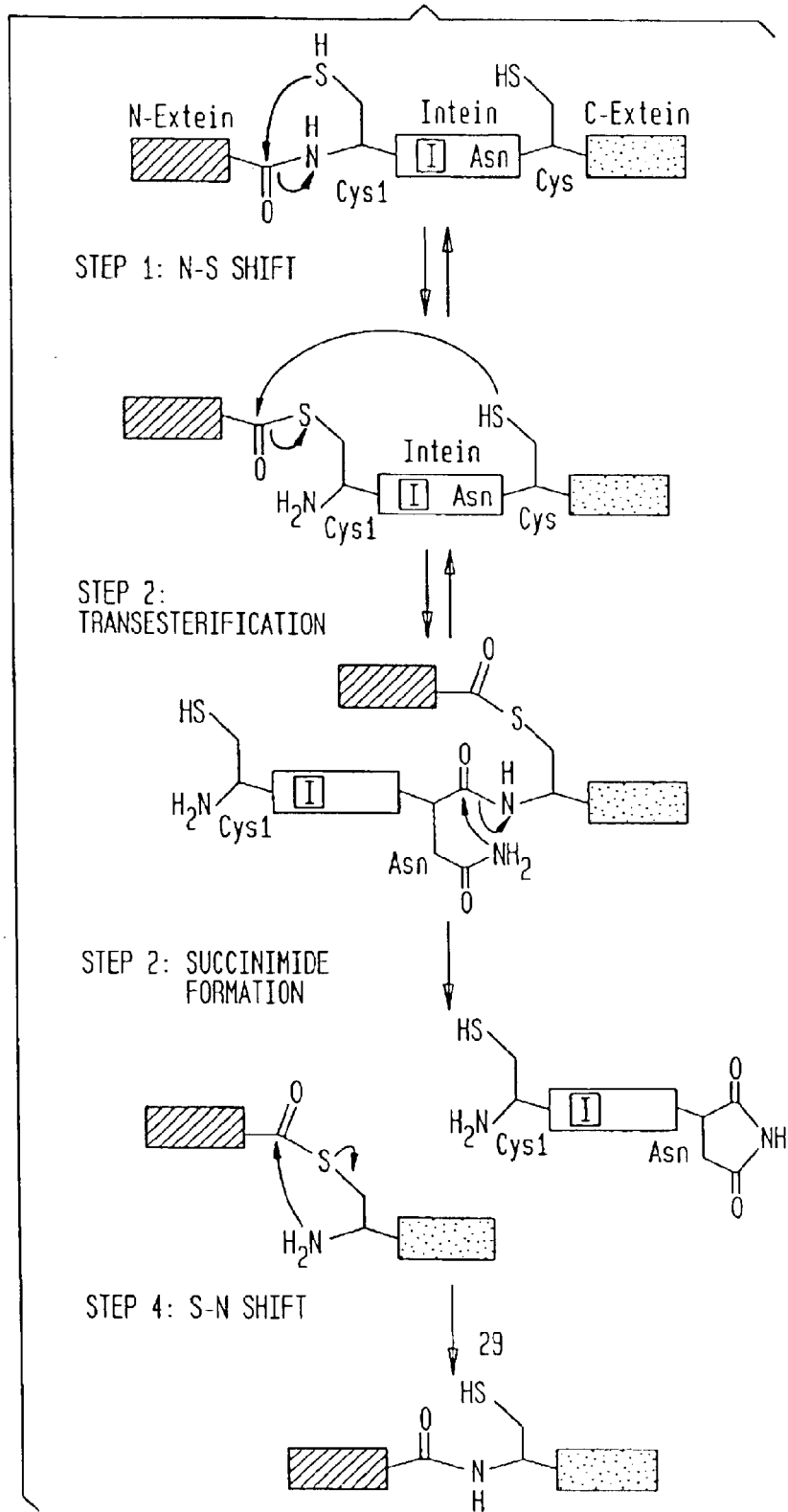
FIG. 1A—Protein Splicing Mechanism. Protein splicing is a post-translational processing event involving the excision of an internal protein segment, the intein, from a precursor protein with the concomitant ligation of the flanking N- and C-terminal regions (the exteins). Sequence alignment reveals that there are highly conserved residues at the two splice junctions: a cysteine or serine residue at the N-terminus of the intein, His-Asn at the C-terminus of the intein, and Cys, Ser or Thr as the first residue of the C-terminal extein. These conserved splice junction residues are directly involved in the catalysis of peptide bond cleavage and ligation of the protein splicing reactions. The chemical mechanism of protein splicing with an intein which has cysteine residues at its N-terminus and adjacent to its C-terminus is shown in FIG. 1: Step 1—Formation of a linear thioester Intermediate by an N—S acyl rearrangement of Cys1 at the N-terminus of the intein; Step 2—Formation of a branched Intermediate by transesterification involving attack by the Cys immediately following the C-terminus of the intein on the thioester formed in Step 1; Step 3—Excision of the intein by peptide bond cleavage coupled to succinimide formation involving the intein C-terminal Asn residue; Step 4—Spontaneous S—N acyl rearrangement of the transitory ligation product from a thioester to a stable amide bond. Protein splicing involving other inteins presumably proceeds by four analogous chemical steps, except that the Cys residues shown in FIG. 1 can be replaced by Ser or Thr, so that Steps 1 and 4 are N—O and O—N acyl shifts, respectively.
Figure 1B:
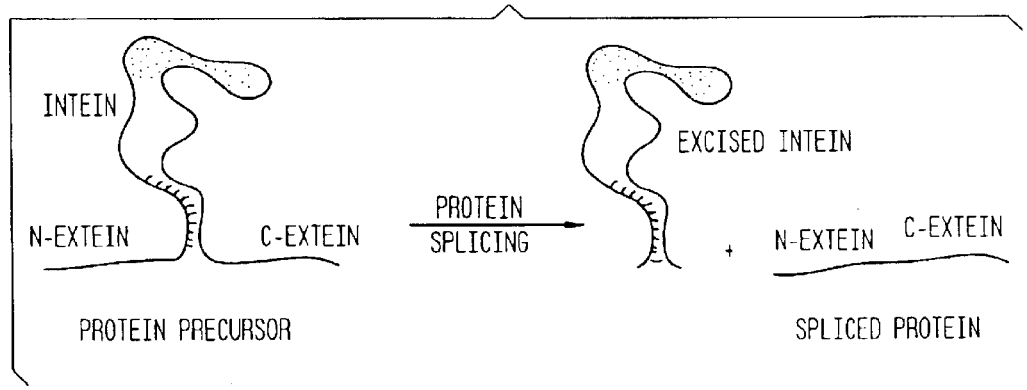
FIG. 1B—Cartoon of protein splicing.

Protein splicing involves the excision of an intervening sequence from a polypeptide with the concomitant joining of the flanking sequences to yield a new polypeptide (Chong, et al., *J. Biol. Chem.*, 271:22159–22168 (1996)), as illustrated in FIGS. 1A and 1B. The elucidation of the mechanism of protein splicing has led to a number of intein-based applications (Comb, et al., U.S. Pat. No. 5,496,714; Comb, et al., U.S. Pat. No. 5,834,247; Camarero and Muir, *J. Amer. Chem. Soc.*, 121:5597–5598 (1999); Chong, et al., *Gene*, 192:271–281 (1997), Chong, et al., *Nucleic Acids Res.*, 26:5109–5115 (1998); Chong, et al., *J. Biol. Chem.*, 273:10567–10577 (1998); Cotton, et al., *J. Am. Chem. Soc.*, 121:1100–1101 (1999); Evans, et al., *J. Biol. Chem.*, 274:18359–18363 (1999); Evans, et al., *J. Biol. Chem.*, 274:3923–3926 (1999); Evans, et al., *Protein Sci.*, 7:2256–2264 (1998); Evans, et al., *J. Biol. Chem.*, 275:9091–9094 (2000); Iwai and Pluckthun, *FEBS Lett.* 459:166–172 (1999); Mathys, et al., *Gene*, 231:1–13 (1999); Mills, et al., *Proc. Natl. Acad. Sci. USA* 95:3543–3548 (1998); Muir, et al., Proc. Natl. Acad. Sci. USA 95:6705–6710 (1998); Otomo, et al., *Biochemistry* 38:16040–16044 (1999); Otomo, et al., *J. Biolmol. NMR* 14:105–114 (1999); Scott, et al., *Proc. Natl. Acad. Sci. USA* 96:13638–13643 (1999); Severinov and Muir, *J. Biol. Chem.*, 273:16205–16209 (1998); Shingledecker, et al., *Gene*, 207:187–195 (1998); Southworth, et al., *EMBO J.* 17:918–926 (1998); Southworth, et al., *Biotechniques*, 27:110–120 (1999); Wood, et al., *Nat. Biotechnol.*, 17:889–892 (1999); Wu, et al., *Proc. Natl. Acad. Sci. USA* 95:9226–9231 (1998a); Wu, et al., *Biochim Biophys Acta* 1387:422–432 (1998b); Xu, et al., *Proc. Natl. Acad. Sci. USA* 96:388–393 (1999); Yamazaki, et al., *J. Am. Chem. Soc.*, 120:5591–5592 (1998)).

Figure 2A:
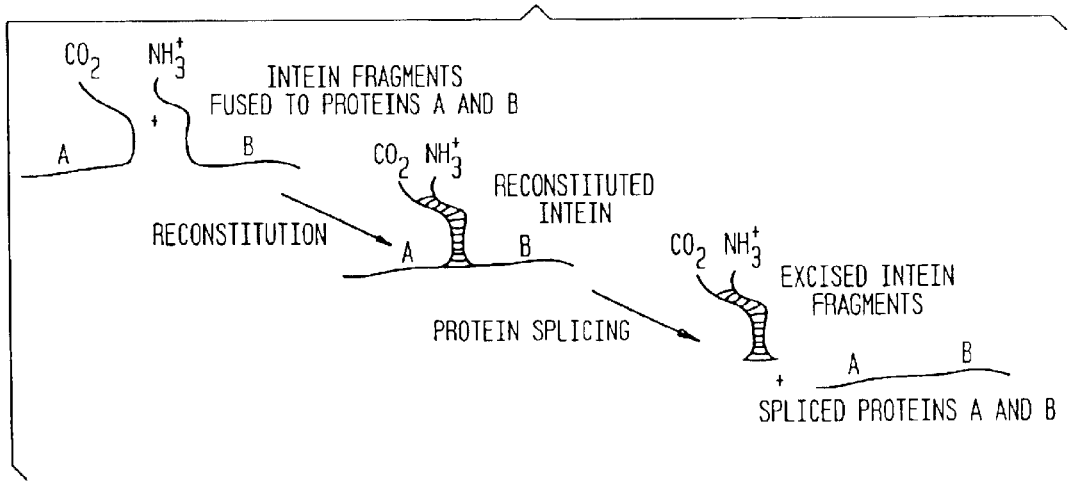
FIG. 2A—The association of the N-terminal and C-terminal intein fragments aligns the two splice junctions for the fusion of the N- and C-extein sequences. The splicing reaction presumably occurs via the same splicing pathway as the cis-splicing pathway proposed previously.
Figure 2B:
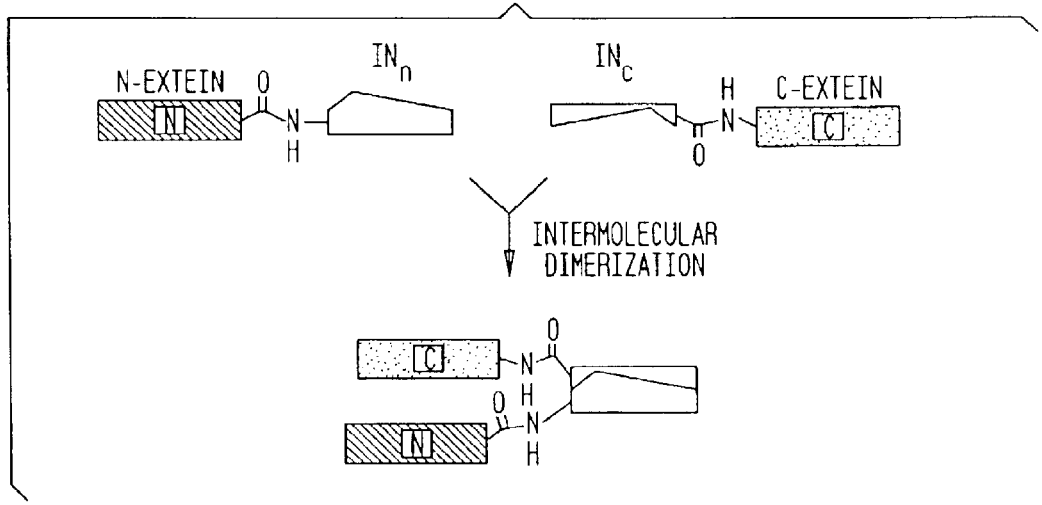
FIG. 2B—Alternatively, in the absence of splicing the intein could facilitate the association of the two extein sequences with the subsequent generation of enzymatic activity. This has been termed intein-mediated complementation.

Protein splicing in trans has recently been described both in vivo and in vitro (Shingledecker, et al., *Gene* 207:187 (1998), Southworth, et al., *EMBO J.* 17:918 (1998); Mills, et al., *Proc. Natl. Acad. Sci. USA*, 95:3543–3548 (1998); Lew, et al., *J. Biol. Chem.*, 273:15887–15890 (1998); Wu, et al., *Biochim. iophys. Acta* 1387:422–432 (1998b), Yamazaki, et al., *J. Am. Chem. Soc.* 120:5591 (1998), Evans, et al., *J. Biol. Chem.* 275:9091 (2000); Otomo, et al., *Biochemistry* 38:16040–16044 (1999); Otomo, et al., *J. Biolmol. NMR* 14:105–114 (1999); Scott, et al., *Proc. Natl. Acad. Sc. USA* 96:13638–13643 (1999)) and provides the opportunity to express a protein as two inactive fragments that subsequently can undergo ligation to form a functional product (FIG. 2).

Figure 3:
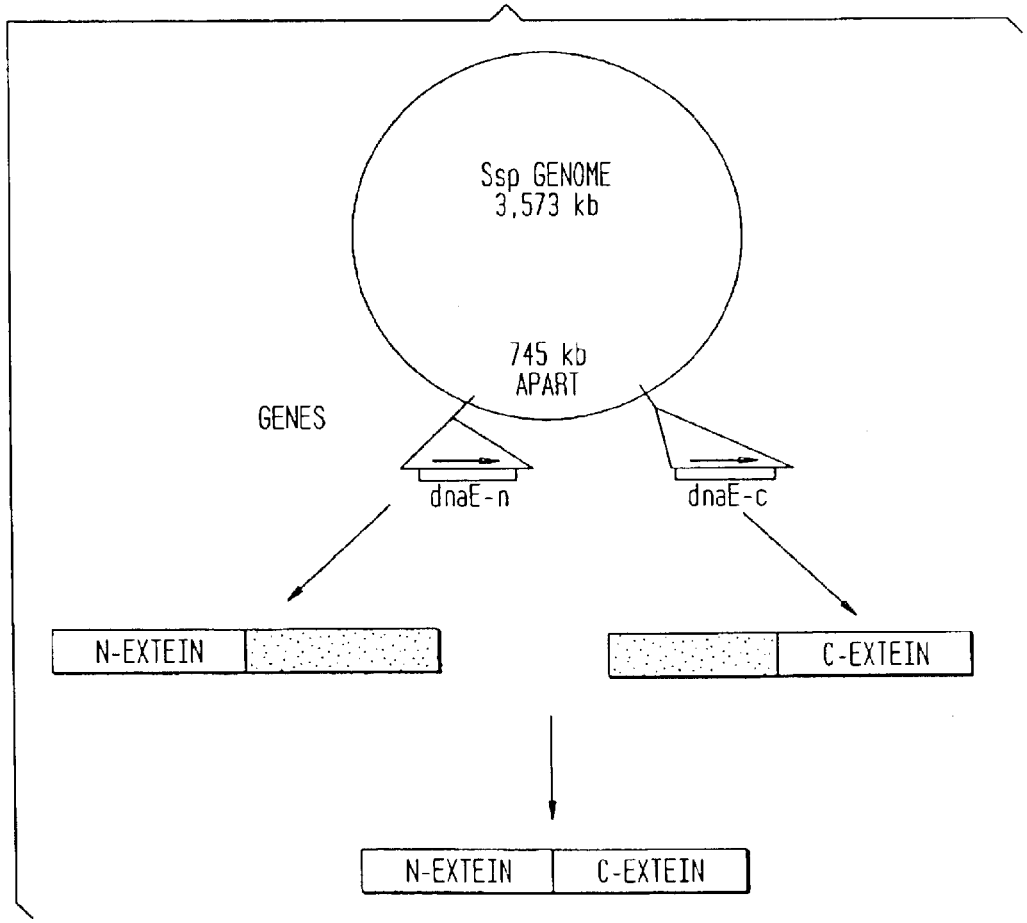
FIG. 3—Ssp DnaE intein gene arrangement in *Synechocystis* sp PCC6803. The genome of the blue-green algae *Synechocystis* sp PCC6803 contains the split dnaE gene with the fragments located 745 kb apart. The naturally occurring trans-splicing intein fuses the two gene product fragments to produce an active polymerase.

Trans-protein splicing also occurs naturally in *Synechocystis* sp PCC6803 (Wu, H., et al., *Proc. Natl. Acad. Sci.* 95:9226 (1998)), where it is essential for forming a functional DNA polymerase III by joining two fragments of the DnaE protein, encoded by two genes separated by 750 kb of chromosomal DNA (FIG. 3).

Figure 4A:
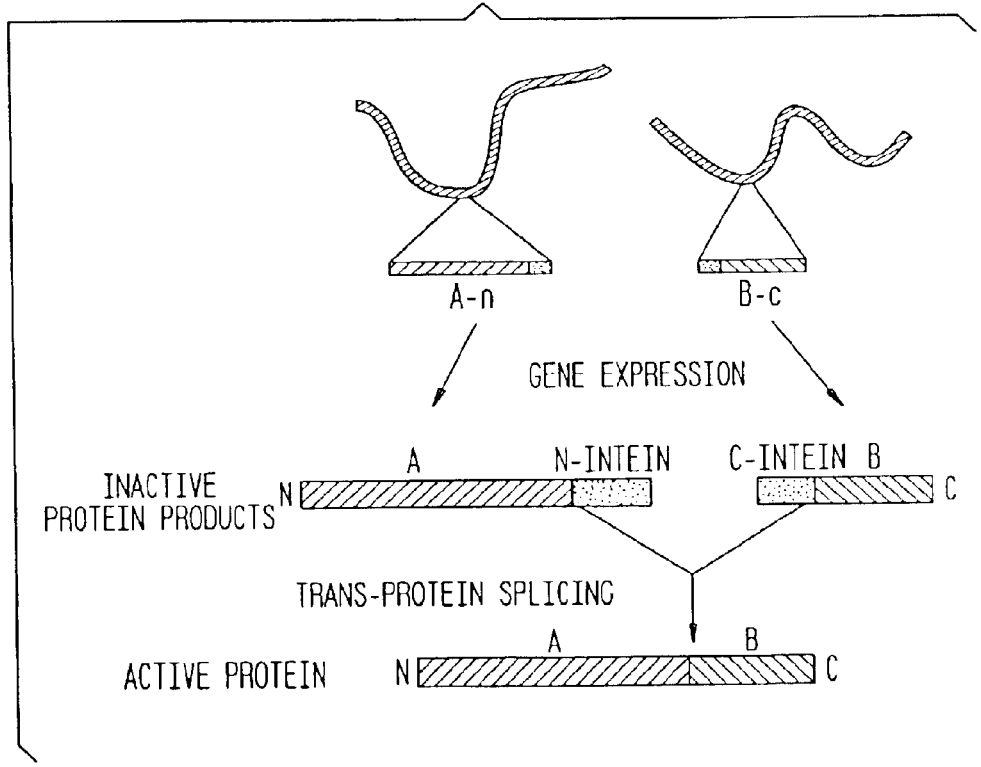
FIG. 4A—Splitting of a target gene. A target gene can be split into two fragments with partial intein genes fused at the C- and N-terminal portions. These split genes can be placed into plant chromosomes so that the following expression can be reconstituted.
Figure 4B:
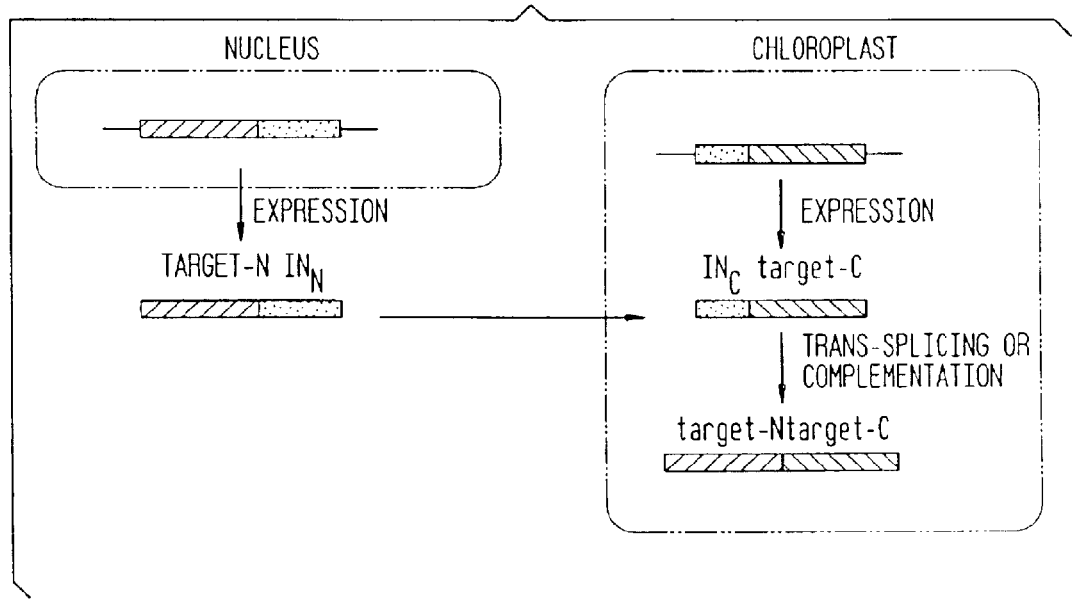
FIG. 4B—Containment of a trans-gene. The gene of interest, in this case an herbicide resistance gene, is divided into two fragments (target N and target C) and an intein ($IN_n$ and $IN_c$) is fused to each partial gene. The two gene fusions are placed on separate, remote locations on the genome. One of these may be in the chloroplast, the other in the nuclear genome. The chloroplast located transgene is transcribed and translated in the chloroplast while the nuclear transgene is transcribed in the nucleus and translated in the cytoplasm. Following translation of the nuclear gene it is transported into the chloroplast with the help of chloroplast transit peptide where it can associate with the other gene fragment using the intein as either an association or splicing element.

These observations led the present inventors to investigate whether a functional gene product could be generated by splitting the gene of interest into two fragments and fusing an intein fragment to each partial target gene. Expression of the two protein fragments followed by trans-splicing, intein mediated complementation, or protein complementation would generate an active form of the target protein (FIG. 4). In this scenario the target gene fragments can be located anywhere in the host genome, including being widely separated in the nucleus, chloroplast, mitochondria, plasmids, bacterial artificial chromosomes, yeast artificial chromosomes, or any combination of these. Furthermore, by placing the gene fragments into different organelles or plasmids, such as one half in the nucleus and the other half in the chloroplast or mitochondria of a plant, the transfer of both gene halves, needed to reconstitute the fully active target protein, for example, to a distant relative by pollination or by horizontal gene transfer via a bacterial, fungal, or viral vector would be virtually eliminated. This would greatly reduce and possibly eliminate the risk of the spread of a transgene outside of its relevant environment.

Two examples of splitting a target gene and reconstituting activity using a protein splicing element are described below. The two genes investigated were mutant forms of the acetolactate synthase (ALS) gene from *Escherichia coli* and the 5-enolpyruvyl-3-phosphoshikimate synthetase (EPSPS) gene from *Salmonella typhimurium*, which confer resistance to the sulfonylurea and glyphosate herbicides, respectively. Both enzymes are involved in the biosynthesis of protein building blocks. ALS is the first common enzyme in the biosynthesis of branched-chain amino acids (LaRossa and Schloss, *J. Biol. Chem.*, 259:8753–8757 (1984); Chaleff and Ray, *Science*, 223:1148–1151 (1984); Falco and Dumas, *Genetics*, 109:21–35 (1985)) while EPSPS is required in the synthesis of aromatic amino acids (Stalker, et al., *J. Biol. Chem.* 260:4724–4728 (1985)). Inhibition of these enzymes by chemical compounds can lead to the death of the organism.

The commonly used sulfonylurea herbicides (SU), such as sulfometuron methyl (SM) (Short and Colburn, *Toxicol*

*Ind. Health,* 15:240–275 (1999)), block the growth of bacteria, yeast and higher plants by inhibiting acetolactate synthase (ALS) (EC 4.1.3.18). In order to generate herbicide resistant plants, there was a great effort in identifying a mutant ALS gene which permits growth in the presence of SM. The mutations which render bacteria and yeast resistant to SM were the first to be reported (Hill, et al., *Biochem. J.,* 335:653–661 (1998)). Subsequently, similar point mutations were confirmed in the ALS genes isolated from naturally occurring resistant crops, corn, cocklebur and tobacco (Lee, et al., *EMBO J.,* 7:1241–1248 (1988); Bernasconi et al., *J. Biol. Chem.,* 270:17381–17385 (1995)). Some of these SU tolerant crops, such as corn ICI8532 IT and Pioneer 3180 IR have been commercialized.

In Example I below, the herbicide resistant gene was split and an intein fragment fused in-frame to each partial gene. The split gene was determined to confer resistance to the herbicide SM in *E. coli. E. coli* was used as a model system since it contains the active ALSI and acetolactate synthase III (ALSIII) enzymes, but not an active ALSII. ALSI and ALSIII are the two isoforms of ALS genes in *E. coli* which are crucial for the synthesis of valine, isoleucine and leucine (DeFelice, et al., *Ann. Microbiol.* (Paris) 133A:251–256 (1982)). Their activity is sensitive to valine feedback inhibition. Therefore, by saturating the growth medium with valine, ALSI and III will be inhibited and the cells will stop growing. By introducing a recombinant ALSII into *E. coli* cells, their growth will be rescued since ALSII is resistant to valine inhibition. This feature makes *E. coli* strain ER2744 a good in vivo model system for investigating the activity of the *E. coli* ALSII gene genetically modified by a linker insertion or a trans-splicing intein element.

The second herbicide resistant gene tested was the aroA gene from *Salmonella typhimurium* that has a C301 to T mutation (Stalker, et al., *J. Biol. Chem.* 260:4724 (1985)). This encodes the 5-enolpyruvyl-3-phosphoshikimate synthetase (EPSPS) (EC 2.5.1.19) protein with a Pro101 to Ser change and is known to confer resistance to the herbicide glyphosate (commonly marketed as Round-Up®). In this embodiment, an N-terminal fragment of the EPSPS gene was fused to the N-terminal splicing domain of the Ssp DnaE intein and the C-terminal fragment of the EPSPS gene was fused to the C-terminal splicing domain of the Ssp DnaE intein. In order to determine the sites in the EPSPS protein that would tolerate the insertion of an intein, a linker scanning experiment was performed (Biery, et al., *Nucleic Acids Res.,* 28:1067–1077 (2000)) (GPS®-LS from New England Biolabs, Inc., Beverly, Mass.) that randomly inserted 5 amino acids throughout the protein sequence. Inteins were inserted into those sites found to be tolerant of amino acid insertion. Trans-splicing constructs were then created that placed the gene fusion encoding the N-terminal fragment of EPSPS fused to the N-terminal domain of the Ssp DnaE intein on one plasmid and the C-terminal portion of EPSPS fused to the C-terminal splicing domain of all the Ssp DnaE Intein on another plasmid. For example the EPSPS protein could be split at the site corresponding to Gly235. The two plasmids were co-transformed into *E. coli* cells which lacked a functional EPSPS protein and cell growth on M9 minimal media in the presence or absence of the herbicide glyphosate was observed.

The activity of both the split ALS and the split EPSPS herbicide resistant genes were observed whether the intein was unmodified or had its catalytic residues changed, thus eliminating trans-splicing activity. This indicated that although splicing would generate a covalently attached protein product, it is not necessary to do so in every situation. The intein in this manifestation would work as an affinity domain to bring the two protein fragments together and in the correct orientation. In these experiments the presence of the intein was absolutely required for activity of the split proteins. This is based on the observation that both the split ALS and EPSPS genes without an intein fusion were not able to allow *E. coli* growth on the appropriate herbicides.

In one embodiment of the invention, two gene fragments, fused to an intein splicing domain, are introduced independently into nuclear chromosomes, using selectable markers such as resistance to an antibiotic or other growth inhibitors to verify gene transfer. Independent transfer of the two fusion genes will assure a remote location on the plant genome, probably on separate chromosomes, thus excluding the possibility that both genes could be acquired by a single virus or plasmid vector for transfer to other organisms. If so desired, the remote location of the two genes can be assured by targeting to specific sites by homologous recombination with known DNA sequences.

In another embodiment, one of the two fusion proteins is transformed into the cell nucleus and the other into chloroplasts, so as to eliminate virtually any chance of gene transfer to related plants by any conceivable mechanism, including cross-pollination of related species, since only inactive fragments of the gene would be present in the pollen. The gene fragments in chloroplast are maternally transmitted and cannot be transmitted through pollen. The same consideration would apply to gene fragments expressed in mitochondria.

This technology may also be applied to non-plant systems. By way of example, a transgene to be compartmentalized could be split and an intein fused to the gene fragments. In the case of bacteria, the split genes are preferably placed far apart on the bacterial chromosome using standard chromosomal transformation techniques. As a further control measure the gene segments may also be arranged in opposite orientations. Another manifestation of this method is to split a target transgene in two and fuse to the appropriate intein domains prior to insertion of the split gene into a eukaryotic cell to prevent the transgene's activity from being spread to the environment or neighboring cells. The split gene is also placed far apart on the eucaryotic chromosome or placed on separate chromosomes. Furthermore, the gene fragments may be located in separate organelles such as the nucleus and mitochondria. The gene fragment in mitochondria is maternally transmitted.

One application of the present invention is in preventing the spread of complete transgenes to the environment from transgenic plants. This is accomplished by splitting the transgene fusions into two or more fragments and fusing these to intein fragments. The partial transgene fusions are located in separate compartments, such as one portion in the nuclear DNA and the second portion in the chloroplast DNA. Following expression of the partial genes, the protein fragments are directed to the site of activity where they associate to reconstitute the target protein activity. Only the transgene fragment present in the nucleus is spread through pollen since the chloroplast DNA is passed to the next generation only maternally. This will vastly reduce the spread of the complete transgene to the environment.

Another advantage of the present invention is that the host cells expressing only one inactive fusion protein species of a protein can be handled safely, thereby reducing the risk of exposing humans and the environment to the target protein, which may be a toxin, etc. Also, splitting a target gene into two separate loci greatly reduces the chance of transferring the entire protein coding sequence into other organisms through DNA carriers (plasmid, virus, cosmid, etc.) or other means (cell fusion, etc.). One hypothetical case is to express a toxic gene, for example the diphtheria toxin. The diphtheria toxin protein is an extremely toxic protein to human and animal cells and needs to be handled extremely carefully. This protein has been tested in preclinical and clinical phase I trials for use as a drug to eradicate tumor cells (Kelley, *Proc. Natl. Acad. Sci. USA* 85(11):3980–3984 (1988); Alexander, *Neuron* 3(1):133–139 (1989); Maxwell, et al., *Cancer Res.* 51(16)4299–4304 (1991); Madshus, *J. Biol. Chem.*, 269(26):17723–17729 (1994); Murphy and vanderSpeck, *Semin Cancer Biol.* 6(5) 259–267 (1995); Rozemuller and Rombouts, *Leukemia,* 12(5):710–717 (1998); Veggeberg, *Mol. Med. Today* 4(3):93 (1998); Kreitman, *Current Opin. Immunol.,* 11(5):570–578 (1999); Vallera, et al., *Protein Eng.* 12(9):779–785 (1999)). Therefore it would be advantageous to split the diphtheria toxin gene into two intein fusion DNA segments and express them in two different bacteria or yeast strains. The two fusion proteins can be mixed, when it is needed, to assemble the toxin.

Thirdly, by compartmentalizing at least one of the fragments of the target gene into an organelle that is subject to maternal inheritance (e.g., chloroplasts or mitochondria), the genetic transfer of the functional gene to related organisms through processes such as cross-pollination can be avoided.

The invention described may also be utilized as a means for expressing any gene of interest in transgenic animals. Transgenic animal models have been widely used as a scientific tool to conduct biomedical studies or to produce desired proteins. Transgenic mice and other transgenic animals, such as transgenic fish, frog, rat, cow, pig, etc. have been shown to express human genes (or a foreign gene) for research and commercial purposes, such as production of a vaccine or therapeutic agent, or used as an animal model for human disease (Alexander, *Neuron* 3(1):133–139 (1989); Groner, et al., *J. Physiol.* 84(1):53–77 (1990); Patil, et al., *Neuron* 4(3):437–447 (1990); Aloe, et al., *Growth Factors* 9(2):149–155 (1993); Aguzzi, et al., *Brain Pathol.* 4(1)3–20 (1994); Groner, et al., *Biomed. Pharmacother.* 48(5–6) 231–240 (1994); Schorderet, *Experientia* 51(2):99–105 (1995)). One of the concerns is that the transgenic animal may acquire an undesired foreign gene and pass it on to the next generation and thereafter. This would result in genetically altered animal strains, which may have unforeseen social and ethical consequences. In accordance with the present invention, such a transgene can be split into two inactive fusion DNA fragments. One of them could be genetically integrated into an animal genome and the other fragment could be supplied by a DNA carrier (such as virus, etc.) which cannot be incorporated into the genome. Therefore, when one fusion protein from the animal and the other from the DNA carrier co-express, the fusion proteins will reassemble, trans-splice and produce an active protein. This gene arrangement can prevent animals from acquiring an intact foreign gene, thereby avoiding genetic contamination.

The compartmentalization of two gene fragments is an extension of trans-splicing. The protein in question is divided into fragments and the appropriate split genes separated onto the same or different DNA molecules. For example, the genes for the two halves of the DnaE protein from *Synechocystis* sp PCC 6803 with the Ssp DnaE or Ssp DnaB intein splicing domains fused to the appropriate fragments (Wu, et al., *Proc. Natl. Acad. Sci. USA,* 95:9226–9231 (1998a); Wu, et al., *Biochim Biophys Acta* 1387:422–432 (1998b)) could be divided so that one half is in the nucleus and the second half is in the mitochonria of a specified organism.

In carrying out the present invention, one must employ one or more of the following methods:

(1) identifying a suitable split site on the target transgene;

(2) the methodology for splitting the gene into two or more fragments and fusing each fragment to a split intein;

(3) the methodology for successfully generating the split gene product into a functional enzyme or protein;

(4) the methodology for screening the host cell for active gene product or organism;

(5) location of split gene sequences in the relevant cellular compartment;

(6) a method of splitting the target gene into more than two fragments;

(7) use of protein complementation to present transgene spread; and (8) introduction of the transgene.

(1) A method for identification of a suitable split site on any transgene

One preferred method for identifying a split site on the transgene is based on the structural analysis of the protein of interest or its analogs and by sequence homology. This approach involves studying the known biochemical and X-ray, NMR or related structural information in order to determine a preferable intein insertion site and/or sites to divide the protein into fragments. In particular, one should determine which are the pertinent reactive amino acid residues and their spacing and spatial arrangement within the protein. If possible, it may be ideal to split the target gene so that catalytic amino acids are distributed onto each fragment. This will increase the likelihood that neither fragment will have activity alone. The protein split site may be anywhere in the protein, but initial sites for testing should be loops or linkers present between secondary motifs such as beta sheets or alpha helices. The first loops chosen should not be part of the catalytic site, although the eventual split site may be located there. As a first trial, the preferred split site would be a loop or linker region between two folding domains within a protein. This increases the possibility that the protein fragments will fold properly when expressed separately.

If no biochemical or structural information is available for the protein of interest, then the alignment of similar protein sequences from different organisms or of similar protein sequences from the same organism may be informative. The protein alignment could be by sequence comparison by traditional methods or using any of a variety of computer programs such as GCG (Genetics Computer Groups, Madison, Wis.) Regions of high conservation between similar proteins in all likelihood represent areas of general importance and splitting the protein in a region of high conservation should be reserved for later testing. Instead one should determine regions of low conservation, preferably regions that also vary in amino acid number that lie between regions of high conservation. The low conservation indicates that there is a low probability of a catalytic residue being present and the variation in amino acid residue length indicates that the exact spacing between the conserved domains may not be dictated by this stretch of amino acids. These properties would be advantageous for a site of intein insertion and splitting a target protein.

Also, when choosing the site to insert an intein in the protein of interest one should test sites that possess amino acid residues favorable for the splicing activity of the intein being tested. Preferably a site in the target protein that was similar or identical to the naturally occurring extein residues of the intein under investigation could be chosen. Alternatively, residues known to facilitate proficient splicing may be inserted together with the intein. In this case, following the splicing reaction these residues would be present in the sequence of the spliced product and may alter the activity of the target protein. The effect of these extra residues on the target protein should be tested by inserting the extra amino acids into the target protein and checking for the desired property or activity.

Another preferred method is based on systematic scanning of a protein of interest by random linker insertion. Linker scanning can be performed by many methods (Gustin, et al. *Methods Mol. Biol.* 130:85–90 (2000); Hobson, et al. *Methods Mol. Biol.* 57:279–285 (1996); Biery, *Nucleic Acids Res.* 28:1067–1077 (2000)). This protocol generates a library of genes with extra stretches of DNA randomly inserted throughout. When this library is translated it produces a set of proteins with extra amino acid residue(s) inserted in different positions. The library is then screened for the desired property of the target protein. For example, if the target protein confers resistance to an herbicide then the library is screened to determine which of the proteins with the extra amino acid residues can allow growth of the target organism in the presence of an herbicide. A list of sites in a protein that can tolerate extra amino acids is created. If structural or biochemical information is available, this list can be compared with the known information. An ideal case would involve choosing a split site that tolerates the extra amino acid insertion and is present in a linker or loop region and results in catalytic residues being located on different fragments. If no structural information is available then one would preferably begin by splitting the gene at the tolerant site closest to the middle of the target protein and continue testing split sites outward from there until the desired activity can be reconstituted. In both methods a preferred insertion site would also posses the native extein sequence for the intein being used, although this is not required. The fusion proteins may have optimized amino acid residues at the splice junctions that allow for a functional product to be assessed.

(2) A method for splitting a gene and fusing each gene fragment in-frame to a split intein coding sequence Once a site to split a gene of interest has been determined (see above), then the target gene is split into two or more fragments using common genetic techniques (Sambrook, et al., *Molecular Cloning: A Laboratory Manual*, $2^{nd}$ Edition, Cold Spring Harbor Laboratory, NY: Cold Spring Harbor Laboratory Press (1989)). For example, PCR primers, with appropriate restriction sites, may be designed so that one corresponded to the start of the target gene and the other to the sequence at the split site. Another set of PCR primers may be designed that correspond to the split site and the other end of the target gene. The two target gene fragments are then amplified by PCR (Sambrook, et al., supra) and cloned into a plasmid vector with the same unique cloning sites present in the PCR primers. Once cloned into separate vectors, intein fragments would be fused to the target genes. In one method, the C-terminal end of DNA coding for an N-terminal portion of the target protein would be fused to the N-terminal end of the DNA coding for an N-terminal portion of the intein, and—in a separate fusion—the N-terminal end of DNA coding for a C-terminal portion of the target protein would be fused to the C-terminal end of DNA coding for a C-terminal portion of the intein.

These gene fragment fusions are then transferred to the same or separate expression vectors and transformed into bacterial or eucaryotic cells, existing as single or multicellular organisms, to screen for the desired activity of the target protein. It should be noted that the gene fragments in question could be cloned using restriction sites within or external to the intein gene present either naturally or added by mutation. Also, recombination sites may be used instead of restriction enzyme sites for the movement of the gene by recombination. The gene or gene fragments may then be transferred and/or expressed from a plasmid vector, a viral genome or the genome of a bacterial, eucaryotic, or archeal organism. One preferred method is to utilize a naturally occurring trans-splicing intein, for example the intein from the dnaE gene of *Synechocystis* species PCC6803 (Wu, et al., *Proc. Natl. Acad. Sci. USA* 95:9226–9231 (1998)). However, any of the known inteins could be used (See InBase at http://www.neb.com/neb/frame_tech.html; Perler, et al., *Nucleic Acids Res.*, 28:344–345 (2000)). This would involve splitting the full length intein in order to generate the desired affinity or trans-splicing domains. One method would be to split the full length intein in the linker region between the blocks B and F of the protein splicing domains (Petrokovski, *Protein Sci.* 7:64–71 (1998); Perler, et al., *Nucleic Acids Res.* 25:1087–1093 (1997); Perler, et al., *Nucleic Acids Res.*, 28:344–345 (2000)).

(3) Creating a functional protein from expressed split fragments

The next step is to use an intein as an affinity domain to facilitate complementation and reconstitution of the N- and C-terminal halves of a protein into a functional enzyme. The sites to determine protein splitting would be as described in (1) above and the cloning of the target gene fragments and the addition of the intein domains as described in (2). In this case the intein fragments need not cause splicing of the two protein fragments to reconstitute enzyme activity. In one preferred embodiment, the intein domains would be mutated to abolish the possibility of splicing activity and would act only as a facilitator of protein complementation. The intein splicing activity could be abolished by mutating the amino acid residues involved in the splicing reaction (Xu, et al., *EMBO J.* 15:5146–5153 (1996); Chong, et al., *J. Biol. Chem.* 271:22159–22168 (1996); Chong, et al., *Biochem. Biophys Res. Commun.*, 259:136–140 (1999); Chong, et al., *Gene*, 192:271–281 (1997); Chong, et al., *Nucleic Acids Res.*, 26:5109–5115 (1998); Chong, et al., *J. Biol. Chem.*, 273 10567–10577 (1998); Chong and Xu, *J. Biol. Chem.*, 272:15587–15590 (1997); Evans, et al., J. Biol. Chem., 274:18359–18363 (1999); Evans, et al., *J. Biol. Chem.*, 274:3923–3926 (1999), Evans, et al., *Protein Sci.*, 7:2256–2264 (1998); Evans, eta I., *J. Biol. Chem.*, 275:9091–9094 (2000); Mathys, et al., *Gene*, 231:1–13 (1999); Paulus, *Chem. Soc. Rev.*, 27:375–386 (1998); Perler, et al., *Nucleic Acids Res.*, 25:1087–1093 (1997); Pietrokovski, et al., *Protein Sci.*, 3:2340–2350 (1994); Pietrokovski, et al., *Protein Sci.*, 7:64–71 (1998), Scott, *Proc. Natl. Acad. Sci. USA*, 96:13638–13648 (1999), Shingledecker, et al., *Arch Biochem. Biophys.* 375:138–144 (2000); Southworth, et al., *Biotechniques* 27:110–120 (1999); Telenti, et al., *J. Bacteral.*, 179:6378–6382 (1997); Wood, et al., *Nat. Biotechnol.*, 17:889–892 (1999); Wu, et al., *Biochim Biophys Acta* 1387:422–432 (1998b); Wu, et al., *Proc. Natl. Acad. Sci. USA* 95:9226–9231 (1998a)).

In another embodiment the intein affinity domain could retain its normal catalytic residues. Furthermore, the intein may be comprised of a deletion or mutant form such that it is significantly smaller or larger or contains non-native amino acid residues when compared to its original primary sequence. The deletion forms of the intein could be created by sequentially decreasing the size of the intein either at the gene level or proteolytically and then testing for affinity activity. The affinity activity could be tested by using the split herbicide resistant gene and fusing the new deletion mutant to the appropriate herbicide resistant gene fragments and looking for growth on the herbicide in question. Mutants of the intein fragment could be formed by error prone PCR, linker scanning, site directed mutagenesis, or by mutagenic compounds and the activity of the intein fragments tested as described above. Note the herbicide resistance gene could be substituted by a drug resistance gene, green fluorescent protein or any selectable marker. The affinity of the intein fragments could also be tested by immobilizing one fragment on a solid support and testing for the binding of the second fragment to the first fragment.

(4) A method of screening for constructs producing active proteins of interest in a suitable host cell or organism The screen for the target gene activity will vary with the target gene but could be by in vitro assay following expression and purification or in a crude cell lysate or in vivo by determining protein activity by cell phenotype, such as viability, morphology, sensitivity, or insensitivity to a drug or compound, appearance, or ability to bind or not bind a specific molecule or compound. One preferred method is to use E. coli as host cells to test, for example, herbicide resistant activity of the re-assembled product of a split gene. The E. coli cells must be sensitive to the herbicide in question. The target gene fragments, with the intein fusion, is present on a plasmid or plasmids and is transformed into E. coli cells using standard techniques.

The gene fusions are expressed either constitutively or by an inducible promoter. E. coli are then tested for growth under selection conditions, i.e. in the presence of herbicide, in both the presence or absence of the appropriate gene fragments. Growth in the presence of the gene fragments indicates the reconstitution of the target protein activity. The E. Coli cells could be substituted with any bacterial, archaea, or eucaryotic cell type (either single or multicellular) as well as a virus by employing techniques well known in the art.

Furthermore, both of the target gene fragments could be present in the genome of the organism, or one fragment could be present in the genome and the other in a plasmid or some other vector. The target protein fragments could be expressed in one organism together or separately and added to another cell type for assay. The fusion could be tested directly in plant cells or other multicellular organisms by placing the transgene fragments in the host organisms nuclear, chloroplast, or mitochondrial genome and determining if the desired activity is present. The target gene or protein fragments could be delivered by a bacterial, fungal, viral, micellar, mechanical (biolistic) or similar vector to the cell type or organism to be tested.

(5) Location of split genes

The present invention also comprises location of the split target gene sequences in different cellular compartments, different locations on the chromosome, or different vectors. One preferred method is to position the two split gene sequences in the nucleus, chloroplast, mitochondria, bacterial artificial chromosome, yeast artificial chromosome, plasmid, preferably not both in any one of the aforementioned. Location of fragments can be accomplished in accordance with standard molecular biology techniques. In order to reconstitute the gene product from its fragments, the appropriate gene fragments must be fused to a targeting/localization sequence so that their protein products are transported into a cellular compartment (e.g., the chloroplasts) where functional reconstitution can occur.

(6) A method of splitting the target gene into two or more fragments

The present invention also embodies methods for splitting the target gene into two or more fragments and reconstituting the desired activity by trans-splicing, intein mediated complementation or protein complementation of all the necessary fragments. For example, inteins with differing affinities could be attached to the target protein fragments so that they reassemble the active protein, in a manner described previously (Otomo, et al., Biochemistry, 38:16040–16044 (1999); Otomo, et al., J. Biomol. NMR, 14:105–114 (1999)). In this case each fragment could be located far apart in the chromosome, on a separate chromosome or in multiple locations as described above, except that the number of locations could match the number of fragments the protein was divided into.

(7) Use protein complementation in the prevention of transgene spread

This protocol uses the natural complementation activity of two protein fragments to reconstitute the desired protein property. The two genes encoding the protein halves may be located in the nucleus, chloroplast, mitochondria, bacterial artificial chromosome, yeast artificial chromosome, plasmid or any combination of those organelles or vectors. Following expression, both protein fragments may be targeted to the site of protein action and the desired protein property generated by complementation of the protein fragments. Protein complementation has been reported previously (Rossi, et al., Trends Cell Biol. 10:119–122 (2000)) and so makes a viable alternative to using an intein as a complementation domain. The procedures necessary to carry out this experiment are similar to what has already been discussed except no intein fusion is used. A site to split a target gene is determined as described in (1). The transgene fragments are cloned as described in (2), except that an intein is not used as a fusion partner. The screening for activity of the split protein is conducted as described in (4).

(8) Introducing a transgene into an organism by viral infection

In yet another embodiment, the two transgene fragments, either intein fusions or not, may be packaged into separate viral particles. These viruses co-infect an organism and both transgenes are expressed. The desired protein property is generated following protein splicing, intein mediated complementation, or protein complementation. One preferred method comprises choosing the split site, clone the fragments and check for activity in trans as described in (1), (2), and (4). The appropriately split transgene or transgene-intein fusions are packaged into adenovirus. The adenoviruses containing the appropriate transgenes can be introduced into a subject organism and upon transfection introduce the two gene fragments so that the target protein activity can be expressed.

BRIEF DESCRIPTION OF THE EXAMPLES

In Example I, we demonstrate a method of splitting a herbicide resistant gene by an intein. We show how to select potential split sites in the E. coli herbicide resistant gene encoding for acetolactate synthase (ALS) based on the sequence homology analysis and the crystal structure of the protein of interest or its analog. The DNA fragment encoding for the N-terminal 327 amino acid residues of the ALS protein was fused in frame to the N-terminal 123 amino acids of the Ssp DnaE intein while the DNA fragment encoding for the C-terminal 221 amino acid residues was fused in frame to the C-terminal 36 amino acids of the Ssp DnaE intein. A plasmid vector bearing one of the fusion genes was expressed as an inactive ALS protein fragment. When both fusion gene vectors were Introduced into the same host cell and co-expressed, the two inactive fusion proteins underwent trans-splicing to produce a functional enzyme in vivo, conferring herbicide resistance to the *E. coli* host cells. This approach may be applied to selection of suitable sites in any gene for fusion to an intein sequence.

In Example II, we demonstrate how to choose a split site in the maize ALS gene based on the sequence homology of the maize ALS gene and its *E. coli* counterpart, ALSII gene. The DNA encoding the N-terminal 397 amino acid residues of the maize ALS gene was fused in-frame to the DNA sequence encoding the N-terminal 123 amino acids of the Ssp DnaE intein while the DNA fragment encoding the C-terminal 241 amino acid residues was fused in frame to the DNA encoding the C-terminal 36 amino acids of the Ssp DnaE Intein. We show that, when the two fusion genes were co-expressed, the two fusion proteins underwent trans-splicing to produce a protein product of expected size for the mature protein.

In Example III, we demonstrate a method of identifying potential split sites in a mutant *S. typhimurium* aroA gene encoding 5-enolpyruvyl-3-phosphoshikimate synthetase (EPSPS) based on transposon random linker insertion. Two sites at amino acid positions 215 and 235 of EPSPS among all 42 potential sites were chosen to split the EPSPS gene. The DNA fragment encoding the N-terminal 215 or 235 amino acid residues of the EPSPS protein was fused in-frame to the N-terminal 123 amino acids of the Ssp DnaE intein while the DNA fragment encoding the C-terminal 212 or 192 amino acid residues of EPSPS was fused in-frame to the DNA encoding the C-terminal 36 amino acids of the Ssp DnaE intein. When only introducing half of the EPSPS gene with or without the intein fused and the two complement halves without intein into ER2799, the EPSPS was expressed as a non-functional protein. However, when introducing both the halves of EPSPS fused with both active or inactive intein halves into ER2799, the EPSPS was expressed as a functional protein and confers resistance to the herbicide glyphosate indicating that the N- and C-terminal halves of the Ssp DnaE intein facilitate the complementation and reconstitution of the N- and C-terminal halves of the EPSPS protein by bringing the EPSPS halves in close proximity.

In Example IV, we describe a method in which two unrelated gene products such as aminoglycoside-3-acetyltransferase (enzyme responsible for metabolism of drug spectinomycin or streptomycin) and *Aequorea victoria* soluble modified green fluorescent protein could be trans-spliced to one hybrid protein in *E. coli* cell. Both the genes are located on two different plasmids with respective trans-splicing elements from Ssp DnaE intein. The plasmids have two independent mechanisms of expression. This hybrid protein confers resistance to spectinomycin sulphate.

In Example V, we describe a method in which two unrelated genes, such as aadA (encodes for aminoglycoside-3-acetyltransferase) and smGFP (soluble modified green fluorescent protein), could be located on a single *E. coli*-plant binary vector under the transcriptional and translational control by a chloroplast promoter (PpsbA). Both the genes when expressed are capable of producing a hybrid aminoglycoside-3-acetyltransferase—soluble modified green fluorescent protein. Thus this method allows for rapid trans-splicing screening of protein/protein fragments before introducing to the plant cells using promoter that could be recognized both by *E. coli* and plant cellular machinary.

In Example VI, we describe a method in which a cis-splicing construct containing two fragments of either 5-enolpyruvyl-3-phosphoshikimate synthetase (EPSPS) or acetolactate synthase (ALS) genes along with a Ssp DnaE intein is capable of splicing into a mature protein in plant cytoplasm. This experiment will enforce the idea of cis/trans-splicing in the cytoplasm. This technique would be useful for proteins, which need specific modification for activity/folding in cytoplasmic environment. A part of the target protein gene with necessary transport signal and splicing element will be placed in an organelle for cytoplasmic transport in the form of a pre-cursor polypeptide.

In Example VII, Section 1, we describe a method in which two unrelated genes, such as aadA (encodes for aminoglycoside-3-acetyltransferase) and smGFP (soluble modified green fluorescent protein), could be located on the chloroplast genome and produce a hybrid protein via protein trans-splicing. Success in this method will lead to compartmentalization of protein/protein fragments and trans-splicing of the functional protein. Also transformation of several separated genes in one vector to form a multifunctional protein simplifying engineering of novel characters.

In Example VII, Section 2, we describe a method in which two unrelated genes/gene fragments could be localized in two different compartments in plant cell, such as chloroplast and nucleus and express the respective protein/polypeptide. The nuclear encoded component is tripartite with a chloroplast transit peptide which will help the protein fragment to be synthesized in cytoplasm and migrate in to the chloroplast for the trans-splicing event to occur. The chloroplast half will be as an integrated component in the circular genome of the organelle. The resulting plants will not be able to transfer the novel character of the newly introduced transgene to any closely related species.

The present invention is further illustrated by the following Examples. These Examples are provided to aid in the understanding of the present invention and are not construed as a limitation thereof.

The references cited above and below are hereby incorporated by reference.

EXAMPLE I

Figure 5:
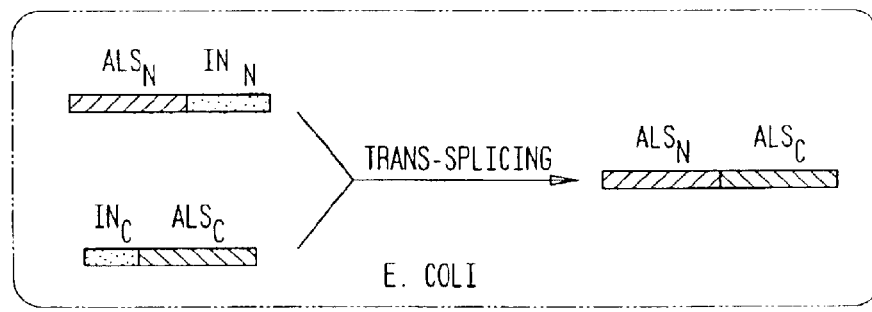
FIG. 5—Trans-splicing of acetolactate synthase (ALS) in E. coli strain ER2744. The target gene is split by intein fragments ($IN_n$ and $IN_c$) and expressed as two inactive partial proteins. Protein trans-splicing produces an active target protein product in host cells.

Production of Functional Herbicide-Resistant Acetolactate Synthase In *E. coli* by Protein Trans-Splicing In this Example we demonstrate a method to split the gene which encodes *E. coli* acetolactate synthase II (ALSII; EC 4.1.3.18; acetohydroxyacid synthase), possessing a herbicide-resistant mutation (Yadav et al, *Proc. Natl. Acad. Sci. USA*, 83:4418–4422 (1986); Hill et al., *Biochem. J.*, 335:653–661 (1998)), by fusion with Ssp DnaE Intein coding sequences (Evans et al, *J. Biol. Chem.* 275:9091–9094 (2000); Scott, et al., *pro. Natl. Acad. Sci. USA*, 96:13638–13643 (1999)). We were able to reconstitute a functionally active ALSII enzyme through protein trans-splicing in the bacterium *E. coli* ER2744 (fhuA2 ginV44 e14-rfbD1? relA1? endA1 spoT1? thi-1 ΔA(mcrC-mrr) 114::IS10 lacZ::T7 gene1) (FIG. 5). First, we show how to select a potential split site in the acetolactate synthase II gene based on the analysis of its sequence and structure homology. Then we show how to design and carry out experiments to analyze the protein trans-splicing activity of the split ALS protein and how to assay the enzymatic activity of reconstituted ALS. We demonstrate that the two portions of the ALS fusion protein, produced from two separate plasmid vectors, undergo trans-splicing to produce a protein product of expected size for the mature protein. Furthermore, co-expression of the split ALS gene fragments conferred resistance to a herbicide in the *E. coli* ER2744. This method may be applied to the production of any protein of interest utilizing trans-splicing inteins.

1. Cloning of wild-type *E. coli* ALSII and generation of its herbicide resistant mutant The initial step is to clone the wild type ALSII and to create a herbicide resistant ALSII mutant carrying Alanine26 to Valine substitution (Yadav et al, *Proc. Natl. Acad. Sci. USA,* 83:4418–4422 (1986); Hill et al., *Biochem. J.,* 335:653–661 (1998)). *E. coli* strain MI162, containing an enzymatic active copy ALSII, was obtained from CGSC, *E. coli* Genetic Stock Center (Yale University, New Haven, Conn.). Genomic DNA was extracted from *E. coli* strain MI162 using QIAamp Tissue Kit (Qiagen, Inc., Studio City, Calif.). DNA Polymerase Chain Reaction (PCR) was performed on the *E. coli* DNA sample to clone the full length ALSII using primers 5'-GGACGGGGAACTAA CTATG-3' (SEQ ID NO:1) and 5'-CCACGATGACGCACCACGCG-3' (SEQ ID NO:2) and Vent® DNA Polymerase (New England Biolabs, Beverly, Mass.). The ALSII coding sequence was further amplified using primers 5' GGAGGGGGCATAT-GAATGGCGCACAGT GGG-3' (SEQ ID NO:3) and 5'-GGGGGGTCATGATAATTTCTCCAAC-3' (SEQ ID NO:4) and cloned into NdeI and PstI sites of pTYB1 plasmid (New England Biolabs, Beverly, Mass.), creating a vector, pALSII. A shorter construct, pTYBT-ALSII, was obtained by the removal of a 3-kb non-essential sequence from pALSII by restriction digestion with PmeI and BstZ172 followed by self ligation. The herbicide resistant mutation, Alanine26 to Valine, was introduced in pTYBT-ALSII by site-directed mutagenesis using Quickchange Site-Directed Mutagenesis kit (Stratagene, La Jolla, Calif.). The mutagenesis primers were 5'-CCGGGTGGCG TAATTATGCCGGTTTACG-3' (SEQ ID NO:5) and 5'-CGTAAACCG GCATAATTACGCCACCCGG-3' (SEQ ID NO:6). The mutated ALSII (ALSIIm) coding sequence generated by partial NdeI and PstI digestion of pTYBT-ALSIIm was ligated with pTYB1 to produce an ALSIIm expression vector, pALSIIm.

2. Selection of Split Site

One preferred method for identifying a suitable split site within any gene, is to analyze the sequence homology of a family of proteins and to examine its protein structure or the structure of its homologues (Ibdah et al., *Biochemistry,* 35:16282–16291 (1996)). Sequence alignment and structure comparison suggest that the ALS genes of bacteria, yeast and higher plants share highly conserved regions (FIG. 6, only partial sequence alignment is shown here). Still, there are highly variable regions present in the proteins, such as the region around amino acid residues Q327 and C328 in the isoform II of the *E. coli* acetolactate synthase (FIG. 6). *E. coli* ALSII has a 10 amino acid gap in this region compared to other homologues and the flanking sequence has less homology among ALS genes from different species (FIG. 6). Furthermore, analysis of the crystal structure of a homologue, pyruvate oxidase, suggests that Q327 and C328 are likely to be located in a linker structure between two intra-molecular domains, away from the catalytic core (Ibdah et al., *Biochemistry,* 35:16282–16291 (1996)). We reasoned, therefore, that ALSII split by an intein at this region may retain the necessary flexibility to allow efficient protein trans-splicing. In addition, insertion of a foreign protein sequence into this location may have less or no effect on the structure of the catalytic domain of ALSII and its enzymatic activity. Thus amino acid residues Q327 and C328 were selected as one of the split sites for *E. coli* ALSII (indicated by an arrow, FIG. 6).

3. *E. coli* assay system

The isoform II of the *E. coli* acetolactate synthase that possesses the mutation Ala26Val, referred to as ALSIIm, confers resistance to sulfonylurea herbicides (SU), such as sulfometuron methyl (SM), In *E. coli* strain ER2744. *E. coli* ER2744 strain was employed as an in vivo model system for assessing the activity of the herbicide resistant *E. coli* ALSII gene, genetically modified by a linker insertion between Q327 and C328. *E. coli* ER2744 is derived from wild type *E. coli* K12 that contains the active ALSI and ALSIII enzymes, but not an active ALSII. ALSI and ALSIII are two isoforms of ALS genes in *E. coli,* which are crucial for the synthesis of valine, isoleucine and leucine (LaRossa and Schloss, *J. Biol. Chem.* 259:8753–8757 (1984)). Their activity is sensitive to the valine feedback inhibition. Therefore, by saturating the growth medium with 100 µg/ml valine (Sigma, St. Louis, Mo.), ALSI and III will be inhibited and the cells will stop growing. By introducing a recombinant herbicide resistant ALSII (ALSIIm) into *E. coli* cells, their growth will be rescued since ALSII is resistant to valine inhibition.

4. Generation of a modified herbicide resistance ALS gene

Inteins often require certain amino acid residues flanking its N- and C-termini to achieve optimal splicing or trans-splicing activity. For example, the intein from the dnaE gene of *Synechocystis* species PCC6803 spliced efficiently when 5 native residues were present at both its N- and C-termini, while deletion of these residues inhibited splicing activity to various extents (Evans et al., *J. Biol. Chem.* 275:9091–9094 (2000)). Inclusion of these optimal amino acid residues at the splice junctions may be required for proficient splicing activity. The resulting product may therefore possess these residues at the ligation junction of two protein sequences. Thus, for each intein insertion site, it is necessary to assess if these extra amino acid residues will have an adverse effect on the activity of the product.

ALSIIm-14 was constructed by insertion of a synthetic DNA linker (New England Biolabs, Beverly, Mass.), encoding the following 14 amino acid residues (NH2-LEKFAEYCFNKSTG-COOH (SEQ ID NO:7)), into the ALSIIm coding sequence between Q327 and C328A. The herbicide resistance activity of ALSIIm-14 was examined using *E. coli* ER2744 host cells transformed by the plasmid expressing ALSIIm-14 protein. *E. coli* ER2744 cells transformed with plasmids expressing the wild type ALSII and herbicide resistant ALSII (ALSIIm) were used as controls.

Figure 7:
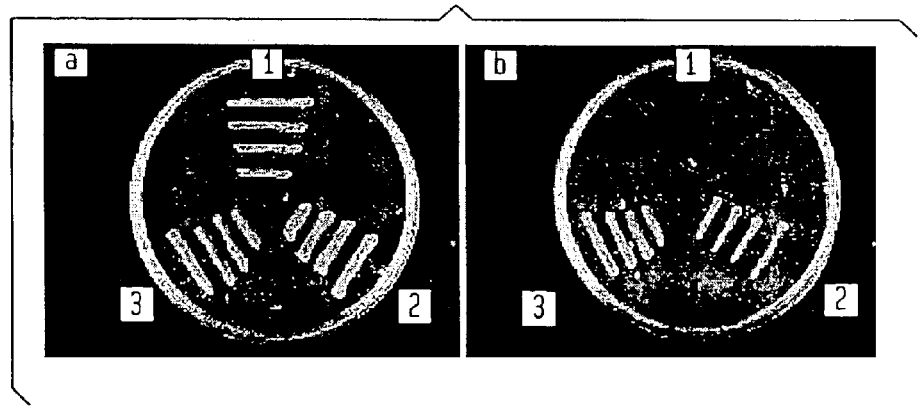
FIG. 7—Plate assay showing that ALSIIm-14 renders E. Coli ER2744 resistant to valine and herbicide, SM. E. coli ER2744 cells were transformed with plasmid DNA expressing ALSII protein (1), ALSIIm (2), ALSIIm-14 (3) and plated on M9 medium containing 0.3 mM IPTG, with 100 μg/ml of valine (a), or with 100 μg/ml valine and 50 μg/ml SM (b). The plate assay was performed at 30° C. for 50 hours.

Plate assays were conducted to examine the capability of ALSIIm-14 to rescue *E. coli* ER2744 from valine (100 µg/ml) or valine plus herbicide SM (50 µg/ml, Supelco Park, Bellefonte, Pa.) saturated M9 minimum medium plate (Sambrook et al., (1989)). The M9 medium contains 2 µg/ml Thiamin, 2 mM $MgSO_4$, 0.1 mM $CaCl_2$, 0.2% glucose, 50 µg/ml of kanamycin, 100 µg/ml of ampicillin and 0.3 mM IPTG. For the plating assay, 100 µl of 25 mg/ml Valine with or without 50 µl of 25 µg/ml Sulfometuron methyl (SM) was spread on M9 selection plate. To assay bacterial growth, overnight cultures were streaked on M9 plates with or without valine and/or SM. The plates were incubated at various temperatures (as indicated in FIG. 7) for 48 to 72 hrs before the pictures were taken. On the plate supplemented with valine, cells expressing either ALSII, ALSIIm or ALSIIm-14 were able to grow (FIG. 7-*a*). However, when both valine and SM was applied, only strains expressing herbicide-resistant ALSIIm or ALSIIm-14 were able to grow (FIG. 7-b). These in vivo results demonstrated that ALSIIm with 14 amino acid residues inserted at the proposed split site, rescued E. coli ER2744 growth in the presence of valine and SM. Therefore, ALSIIm-14 is functionally active and the 14 amino acid insertion does not affect its enzymatic activity.

5. Construction of ALSII-Intein fusion genes

Next, the E. coli ALSIIm gene was split and fused in-frame to the N- and C-terminal halves of the Ssp DnaE intein coding regions. The fusion genes were created using two compatible E. coli expression vectors, pMEB10 and pKEB1, which are capable of co-expressing two intein fusion genes in the same E. Coli host cell, as previously described by Evans et al. (J. Biol. Chem. 275:9091–9094 (2000)). The DNA sequence encoding for an N-terminal fragment of 327 amino acids of the herbicide resistant ALSII (ALSIIM) gene was fused in frame to the coding region for the 7 amino acid residues flanking the N-terminus of the Ssp DnaE intein, followed by the Intein N-terminal 123 amino acid residues ($IN_n$) (FIG. 5). The DNA sequence encoding the C-terminal 221 amino acid residues of ALSIIm was fused in frame to the DNA sequence encoding the C-terminal 36 amino acid residues of the Ssp DnaE intein ($IN_c$) and the 7 amino acid residues flanking the C-terminus of the intein (FIG. 5). ALSII N-terminal fragment was amplified from pALSIIm using primers 5'-GGGGGTCATGAATGGCGCACAG TGGG-3' (SEQ ID NO:10) and 5'-GCGCGCTCGAGTTGATTTAACGG CTGCTGTAATG-3' (SEQ ID NO:11). The amplified fragment was digested and cloned into the NcoI and XhoI sites of pMEB16, which contains the sequence encoding the N-terminal 123 amino acid residues of the Ssp DnaE intein. The resulting vector pEA(N) expresses a fusion protein composed of the ALSIIm N-terminal fragment and the DnaE N-terminal fragment (ALSIIm(N)—$IN_n$). The ALS II C-terminal fragment was amplified using primers 5'-GCGCGACCGGTTGTGACTGGCA GCAACACTGC-3' (SEQ ID NO:12) and 5'-GGGGGGCTGCAGTCA TGATAATTTCTCCAAC-3' (SEQ ID NO:13). The fragment was digested with AgeI and PstI and then cloned into the AgeI and PstI sites of pMEB9. The resulting plasmid PEA(C) expresses a fusion protein composed of the Ssp DnaE intein C-terminal fragment and the ALSII C-terminal fragment (ALSIIm(C)—$IN_c$). A 1 kb XbaI-PstI fragment containing ALSIIm(C)—$IN_c$ fusion gene was subcloned from pEA(C) into the XbaI and PstI sites of pKEB1 plasmid to produce a kanamycin resistant expression vector pKEC3.

When pEA(N) and pKEC3 were co-expressed in E. coli ER2744, it was predicted that trans-splicing of the two fusion proteins would result in ligation of the two split halves of the E. coli ALSIIm, with 14 amino acids present at the ligation junction.

6. Characterization of protein trans-splicing activity

To determine whether ALSII-DnaE Intein fusion proteins are able to trans-splice in E. coli cells to produce ALSIIm-14, western blots were performed using rabbit antiserum specifically against either the N- or C-terminal fragment of ALSII.

Two rabbit antisera were raised against peptides derived from the N-terminal and C-terminal regions of ALSII, respectively (COVANCE). These two peptides are 1) $NH_2$—CAQ WVVHALRAQGVNTVFGYG-COOH (SEQ ID NO:8) derived from the ALSII N-terminal sequence (amino acid residues Ala4 to Tyr23) and 2) $NH_2$—CVWPLVPPGASNSEMLEKLS-COOH (SEQ ID NO:9) derived from the ALSII C-terminal sequence (amino acid residues Val 530V to Ser548). A single bacterial colony was inoculated in LB medium supplemented with 100 µg/ml of ampicillin for 4 hrs at 37° C. Then it was induced by addition of IPTG to 0.3 mM final concentration. Cells were further cultured for 2–16 hours at 15° C. 20 µl of cell culture was removed, mixed with 3×SDS loading buffer (New England Biolabs, Beverly, Mass.), boiled for 5 minutes and 2 µl was loaded to 12% Tris-glycine gel (Novex, San Diego, Calif.). Subsequently proteins were transferred to a nitrocellulose membrane and blocked with 5% dry milk for one hour at room temperature (Sambrook, et al., Molecular Cloning, (1989)). Immunoblotting was performed using antiserum (1:20000 dilution) overnight at 4° C. in the presence of 1% dry milk. Blots were then washed three times for 15 minutes each and incubated with 1:10000 diluted HRP-conjugated anti-rabbit secondary antibody for 1 hour at room temperature. The reactions were visualized with Chemiluminescent Western Detection kit (New England Biolabs, Beverly, Mass.).

Figure 8A:
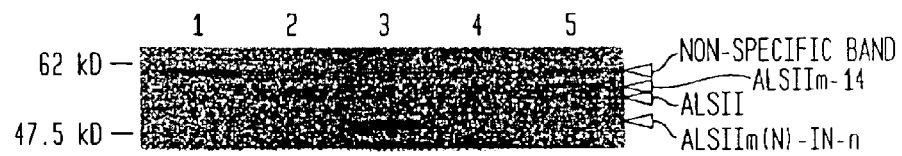
FIG. 8—Production of recombinant ALSIIm-14 through Ssp DnaE intein mediated trans-splicing. 2 μl of whole cell extract, from cells transformed with expression plasmids for control (lane 1), ALSII (lane 2), ALSIIm(N)—$IN_n$ (lane 3), ALSIIm(C)—$IN_c$ (lane 4), ALSIIm(N)—$IN_n$ and ALSIIm (C)—$IN_c$ (lane 5), was run on an SDS-polyacrylamide (12%) gel, transferred to a S&S nitrocellulose membrane, and probed with antiserum against ALSII N-terminus (FIG. 8A) or against ALSII C-terminus (FIG. 8B).
(FIG. 8C) The efficiency of trans-splicing is temperature sensitive. Western blot was performed using a antiserum against ALSIIm N-terminus. Protein extract was made from cells transformed with expression plasmids for control E. Coli extracts contain a non-specific protein (the top band) that reacts with antiserum: (lane 1), ALSII (lane 2), ALSIIm(N)—$IN_n$ and ALSIIm(C)—$IN_c$ (lane 3 to lane 6). The cell culture temperature is 37° C. for lane 1 to lane 3, 30° C. for lane 4, 25° C. for lane 5, and 15° C. for lane 6.
Figure 8B:
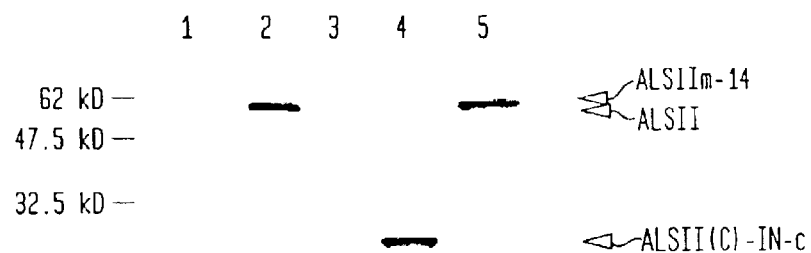

In control cells cultured at 15° C., expression of ALSII (FIGS. 8A, 8B & 8C, lane 2) was recognized specifically by both antibodies. In cells bearing a single ALSII-intein fusion vector and another control vector to confer both ampicillin and kanamycin resistance only ALS(N)—$IN_n$ or ALS(C)—$IN_c$ protein was detected by anti-ALS(N) or anti-ALS(C) serum (FIG. 8A, lane 3, FIG. 8B, lane 4). When ALS(N)—$IN_n$ and ALS(C)—$IN_c$ were co-expressed a 60 kD band, as expected for the spliced product ALSIIm-14, reacted with antibodies raised against the N-terminus and C-terminus of ALSII (FIGS. 8A & 8B, lane 5). This band of AlSIIm-14, as predicted, exhibited a slightly higher molecular weight than native ALSII. The data indicated that trans-splicing occurred between the two ALSII-intein fusion proteins. A non-specific protein reacting with anti-ALS(N) was observed (FIG. 8A and FIG. 8C, lane 1 to lane 5).

Trans-splicing activity of the Ssp DnaE intein was previously shown to be temperature sensitive (Evans et al., J. Biol. Chem. 275:9091–9094 (2000)). The temperature sensitivity of trans-splicing of the ALSII-Ssp DnaE intein proteins were examined by western blot analysis using an antiserum against ALSII N-terminal fragment (FIG. 8C). Cells were transformed by plasmids expressing ALSII, or both ALSIIm(N)—$IN_n$ and ALSIIm(C)—$IN_c$. Expression of the ALSII proteins were induced at 37° C. for 3 hours. Co-expression of ALSIIm(N)—$IN_n$ and ALSIIm(C)—$IN_c$ was induced at 37° C. for 3 hours, 30° C. for 3 hours, 25° C. for 6 hours, or 15° C. for 16 hours. Cell extracts were treated with SDS sample buffer and denatured at 95° C. to 100° C. for 5 minutes and then subjected to electrophoresis on a 12% SDS-PAGE. A western blot was probed using an antiserum raised against the ALSII N-terminal fragment. FIG. 8C includes the following samples: cells with no ALSII (lane 1, control), ALSII (lane 2), ALSIIm(N)—$IN_n$ and ALSIIm(C)—$IN_c$ (lane 3 to lane 6). The cell culture temperature are 37° C. for lane 1 to lane 3, 30° C. for lane 4, 25° C. for lane 5, and 15° C. for lane 6.

Figure 8C:
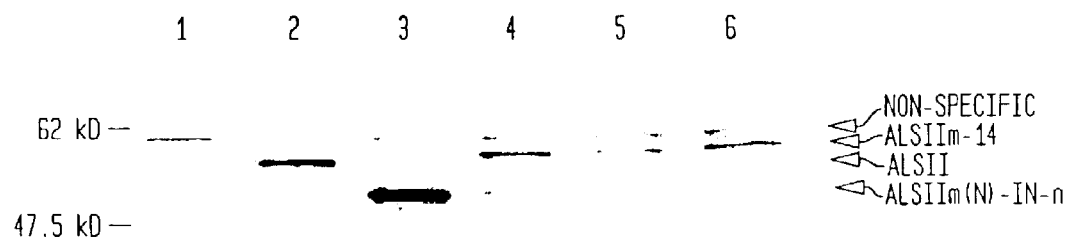
Figure 9A:
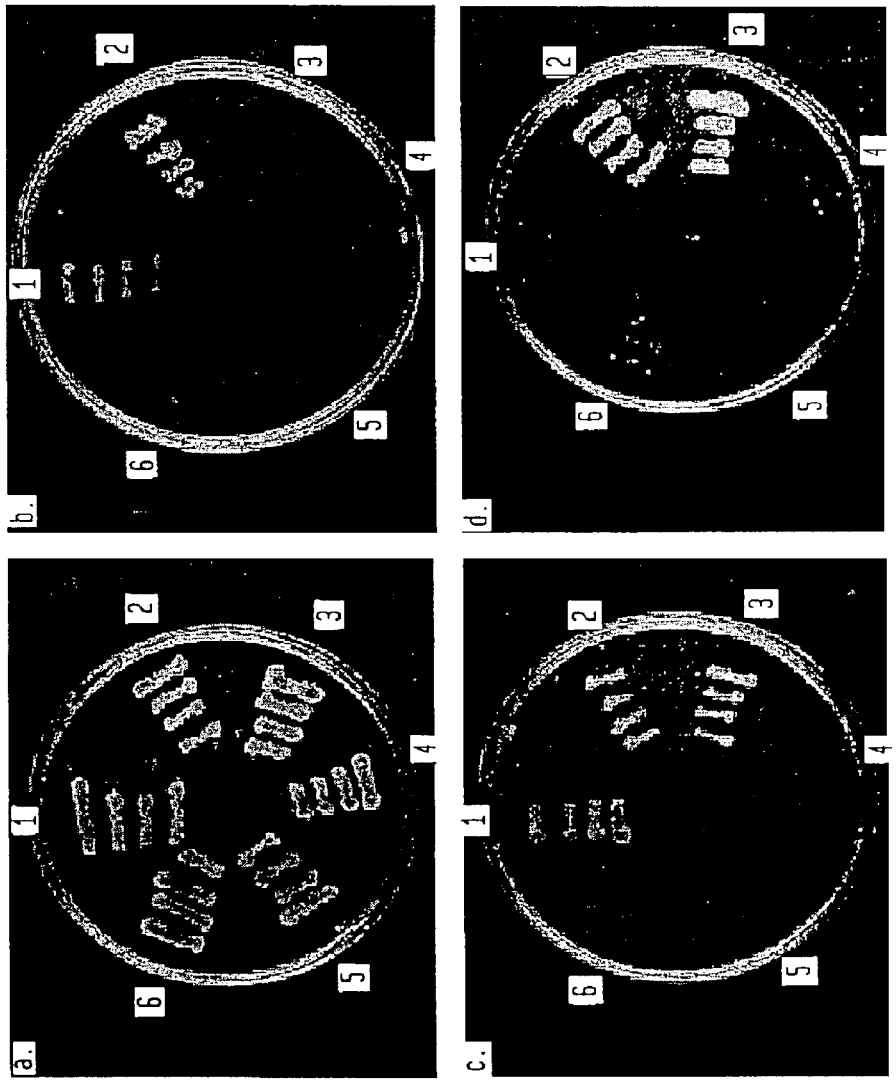
FIG. 9A—Co-expression of ALSIIm(N)—$IN_n$ and ALSIIm(C)—$IN_c$ rescued cell growth on a valine plus herbicide added plate. E. coli ER2744, transformed with expression plasmids for ALSII (1), ALSIIm (2), ALSIIm (N)—$IN_n$ and ALSIIm(C)—$IN_c$ (3), ALSIIm(N)—$IN_n$ (4), ALSIIm(C)—$IN_c$ (5), ALSIIm(N) and ALSIIm(C) (6), were plated on M9 medium at 37° C. (a), 37° C. with 100 μg/ml valine (b), 30° C. with 100 μg/ml valine (c), and 30° C. with 100 μg/ml valine and 50 μg/ml sulfometuron methyl (SM) (d). Plates contained 0.3 mM IPTG.
Figure 9B:
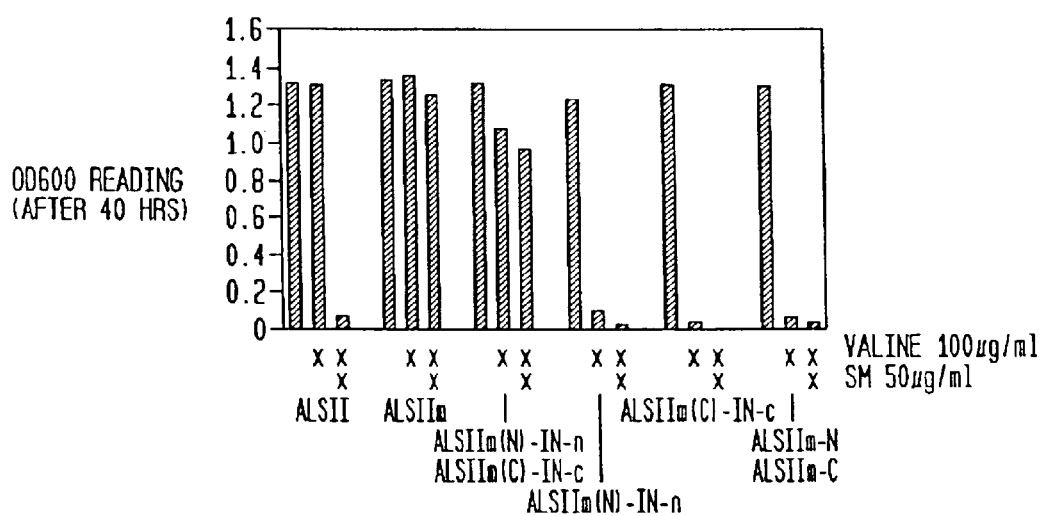
FIG. 9B—Co-expression of ALSIIm(N)—$IN_n$ and ALSIIm-(C)—$IN_c$ rescued cell growth in valine and herbicide added medium. E. coli ER2744, transformed with expression plasmids for fusion proteins as indicated under graph, was cultured in M9 medium (0.3 mM IPTG), with or without 100 μg/ml valine and 50 μg/ml sulfometuron methyl (SM) as indicated. $OD_{600}$ was taken to determine the cell growth rate after cells were cultured for 40 hours at 30° C.
Figure 9C:
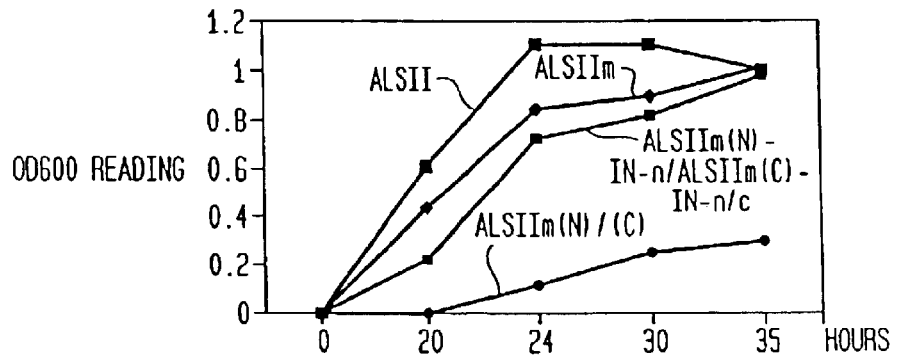
FIG. 9C—The time course study on the growth rate of cells expressing ALSIIm(N)—$IN_n$ and ALSIIm(C)—$IN_c$. E. coli ER2744, transformed with the expression plasmids for proteins as indicated, was cultured at 30° C. in M9 medium (0.3 mM IPTG) with the addition of 100 μg/ml valine. The cell density was determined by measuring $OD_{600}$ at several time points as indicated.

In cells grown at 37° C., ALSIIm-14 was not detectable (FIG. 8C, lane 3). However, in cells cultured at 30° C., the spliced product was observed with a significant amount of N-terminal fusion protein accumulation (FIG. 8C, lane 4). In cells cultured at 25° C. and 15° C. (FIG. 8C, lane 5 and 6), only the spliced product was detected, indicating a complete conversion of the N-terminal fusion protein to the spliced product. The ALSIIm(C)—$IN_c$ protein was produced in excess under all the expression conditions. The data demonstrated that the Ssp DnaE intein was capable of mediating trans-splicing of the N- and C-terminal ALSIIm protein segments to form ALSIIm-14. The splicing reaction was inhibited when the experiment was conducted at 37° C. Splicing appeared to be more efficient when cells were cultured at 15° C.–25° C. rather than at 30° C.

7. Herbicide resistance in cells bearing the spilt ALS gene

The next step was to determine whether the spliced product, as the result of trans-splicing of the ALSIIm (ALSIIm(N)—$IN_n$ and ALSIIm(C)—$IN_c$) fusion proteins, would render *E. coli* ER2744 resistant to valine and SM. The first experiment was to test the effect of co-expression of ALSIIm(N)—$IN_n$ and ALSIIm(C)—$IN_c$ fusion proteins on cell growth in valine saturated M9 minimum medium. In a plating assay (see Section 4.), all transformed cells grew well on M9 medium in the absence of valine (FIG. 9A-a). However, only ALSII and its herbicide resistant mutant ALSIIm rescued the cells growth at both 30° C. and 37° C. (FIG. 9A-b, 9A-c) in the presence of valine. Significantly, co-expression of ALSII(N)-$IN_n$ and ALSII(C)—$IN_c$ rescued cell growth at 30° C. (FIG. 9A-c) or lower temperatures (data not shown) from a valine plate. Furthermore, expression of ALSIIm or ALSIIm(N)—$IN_n$ and ALSIIm(C)—$IN_c$ rescued cells from additional herbicide inhibition (FIG. 9A-d). Moreover, transformation of wild type ALSII could not rescue cell growth from herbicide inhibition (FIG. 9A-d). The control cells which expressed either ALSII(N)—$IN_n$ or ALSII(C)—$IN_c$ alone did not grow on a valine plate (FIG. 9A-b, 9A-c); neither did the co-expression of native ALSII N- and C-terminal segments which were not fused to the intein (FIG. 9A-b, 9A-c). The data indicates that co-expression of ALSIIm(N)—$IN_n$ and ALSIIm(C)—$IN_c$ fragments is required for trans-splicing and generating a functional ALSII, which can rescue cell growth from valine and herbicide inhibition.

A quantitative liquid culture assay was performed to verify the results obtained from the plating assay. The liquid assay was performed as follows. A single colony was used to inoculate LB medium supplemented with kanamycin and ampicillin at 37° C. for 4 hours. Expression was induced by 0.3 mM IPTG and cell cultures were shifted to 30° C. for another 2 hrs. Then, 200 $\mu$L of equivalent $OD_{600}$ 8.0 was spun down, washed one time with M9 medium and resuspended in 200 $\mu$l M9 medium. 40 $\mu$l was aliquoted into 2 ml of appropriate culture medium and grown for 24–72 hours before its $OD_{600}$ was measured. The concentration for valine is 100 $\mu$g/ml and for SM is 50 $\mu$g/ml. At 30° C., all transformed cells grew equally well in M9 minimum medium (FIG. 9B). In valine saturated M9 medium, wild type ALS allowed cells to grow, but no growth was observed when SM was added. However, the expression of ALSIIm or co-expression of ALSIIm(N)—$IN_n$ and ALSIIm(C)—$IN_c$ allowed cells to grow in valine M9 medium, as well as medium containing SM. In control experiments, ALSIIm (N)—$IN_n$ or ALSIIm(C)—$IN_c$ alone or co-expression of ALSIIm N- and C-terminus not fused to the intein, did not rescue cell growth in valine containing medium. This data is in agreement with that from the plating assay. To further compare the growth kinetics for trans-splicing mediated cell growth to wild type ALSII mediated cell growth, a time course study was performed (FIG. 9C). Data showed that ALSII expressing cells have the fastest growth rate followed by ALSIIm expressing cells. ALS(N)—$IN_n$ and ALS(C)—$IN_c$ transformed cells have slower growth rates compared to ALSII wild type expressing cells, but not significantly less than the growth rate of ALSIIm expressing cells. Cells expressing split ALSII, with no fusion to the intein, have very slow growth. Therefore, from the plating and liquid assay we have demonstrated that the Ssp DnaE can mediate ALSII trans-splicing, which results in a functionally herbicide-resistant ALSIIm-14 in vivo.

In conclusion, the data indicated that the two ALS-intein fusion proteins, produced from two different loci, underwent trans-splicing in a temperature-dependent manner to form a full length, functional ALSIIm protein. *E. coli* host cells possessing both ALSIIm fusion gene fragments showed the herbicide resistance phenotype.

EXAMPLE II

Trans-Splicing of a Maize Acetolactate Synthase in *E. coli*

In this Example, we demonstrate a method to produce a full length maize acetolactate synthase by protein trans-splicing in *E. coli*. We demonstrate how to choose a split site in the maize ALS gene based on the sequence homology of the maize ALS gene and its *E. coli* counterpart, the ALSII gene. We show that, when the split maize ALS-intein fusion genes were co-expressed, the two fusion proteins underwent trans-splicing to produce a protein product of expected size for the mature maize ALS protein.

1. Selection of split site.

It is important to demonstrate the trans-splicing of other herbicide resistant genes, such as the maize acetolactate synthase (cALS) gene, of which the herbicide resistant mutant form has been utilized to genetically modify plants (Bernasconi et al., *J. Biol. Chem.* 270:17381–17385 (1995)). One preferred method for the identification of a suitable split site within any gene is to analyze the trans-splicing activity of a homologous gene from a different organism. We have described in Example I, that *E. coli* ALSII gene, after being split between Q327 and C328, can be reconstituted by the trans-splicing activity of the Ssp DnaE intein in vivo. Sequence alignment between *E. coli* ALSII and maize ALS was conducted to search for the region in the maize ALS gene corresponding to the split site of the *E. coli* ALSII gene. The result suggests that Serine397 and Threonine398 align with the split site (Glutamine327 and Cysteine328) of *E. coli* ALSII. Splitting the maize ALS between Serine397 and Threonine398, as indicated by a star (FIG. 6), may yield two maize ALS-intein fusion proteins which would be capable of proficient splicing.

2. Cloning of the maize ALS gene

Reverse transcriptase polymerase chain reaction (RT-PCR) was carried out to clone the maize ALS cDNA.

Total RNA was isolated from corn leaves using the RNAqueous kit (Ambion, Inc., Tex.). The RNA was then used for first strand cDNA synthesis using the reverse primer 3—3 (5'-AT CAGTACACAGTCCTGCCATC-3' (SEQ ID NO:14)) and Superscript Reverse Transcriptase (LTI-GIBCOBRL, Rockville, Md.). The first strand cDNAs were then treated with RNaseH (LTI-GIBCO BRL, Rockville, Md.) before being used as a template in a PCR reaction. The PCR reaction was carried out using Expand Long Template PCR system (Boehringer Mannheim, Germany). The primers used in this reaction were Reverse Primer 3—3 and cALS 5-4 primer (5' GAGACAGCCGCCG CAACCAT-3' (SEQ ID NO:15)).

An aliquot of the PCR product was electrophoresed on an agarose gel and a band of approximately 2 kb was observed. This fragment was cloned into the TOPO 2.1 vector (Invitrogen, San Diego, Calif., manufacturer's protocol) to make pCALS1. The sequence of pCALS1 was confirmed using M13 forward and reverse primers.

3. Construction of the maize ALS-intein fusions

The DNA encoding for the N-terminal 397 amino acid residues of the maize ALS gene was amplified by PCR using forward primer 5'-GGGCCCATATGGCCACCGCC-GCCGCCGCG-3' (SEQ ID NO:16), reverse primer 5'-GGGCCCTCGAGGCTTCCTTC AAGAAGAGC-3' (SEQ ID NO:17), and the template pCALS1 (Sambrook et al., *Molecular Cloning*, (1989)). A 1.2 kb PCR product was cloned into TOPO-blunt vector (Invitrogen, San Diego, Calif. manufacturer's protocol), resulting in TOPO-cALS (N). Then TOPO-cALS(N) was digested with NdeI and XhoI. A 1.2 kb digested DNA fragment was recovered from low melting agarose gel and fused in-frame to the DNA sequence encoding the N-terminal 123 amino acids of the Ssp DnaE intein, resulting In a vector (MEB10-cALS(N) which expresses the N-terminal cALS-intein fusion protein, cALS(N)—IN-n. A DNA fragment encoding for the C-terminal 241 amino acid residues of the maize ALS gene was PCR amplified using forward primer 5'-GGGCCACCGGTACATCAAAGAAGAGCTTG-3' (SEQ ID NO: 18), reverse primer 5'-GGGGCTGCATTCAGTACACAGTCCTGC CATC-3' (SEQ ID NO:19), and the template pCALS4. A 0.8 kb PCR product was cloned into a TOPO-blunt vector (see protocol above), TOPO-cALS(N). TOPO-cALS(N) was then digested with AgeI and PstI. A 700 bp DNA fragment was recovered from low melting agrose gel and was fused in frame to the DNA encoding the C-terminal 36 amino acids of the Ssp DnaE intein, resulting in a vector MEB9-cALS (C). MEB9-cALS(C) was further cut by XbaI and PstI and released a 1 kb fragment. This 1 kb fragment was cloned into pKEB1 vector to create a kanamycin resistant expression vector for the cALS-intein C-terminal fusion protein, cALS (C)—$IN_c$. The same extra 7 amino acids, $NH_2$-LEKFAEY-COOH (SEQ ID NO:20) and $NH_2$—CFNKSTG-COOH (SEQ ID NO:21) were also present at the junctions of the N- and C-terminal cALS-intein fusion proteins, respectively.

4. Trans-splicing of the maize ALS-intein fusion proteins

Figure 10A:
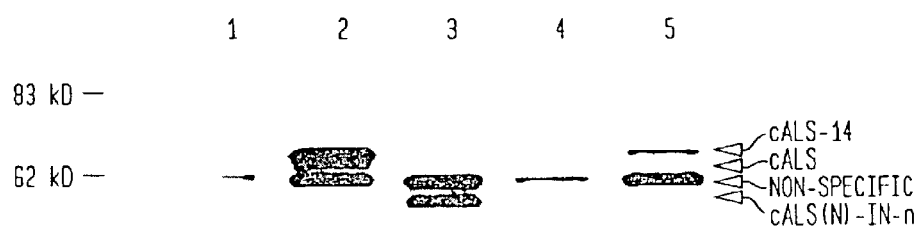
FIG. 10—Western blot detection of trans-splicing product, maize ALS-14. 2 μl of whole cell lysate, from E. coli ER2744 cells transformed with expression plasmids for control (lane 1) (please note the antibody reacts with a non-specific protein in E. coli), cALS (lane 2), cALS(N)—$IN_n$ (lane 3), cALS(C)$IN_c$ (lane 4), cALS(N)—$IN_n$ and cALS(C)—$IN_c$ (lane 5), was run on a 12% SDS polyacrylamide gel, transferred to a S&S Nitracellulose membrane and probed with antiserum against cALS N-terminus (A) or cALS C-terminus (B). cALS indicates corn/maize ALS protein.
Figure 10B:
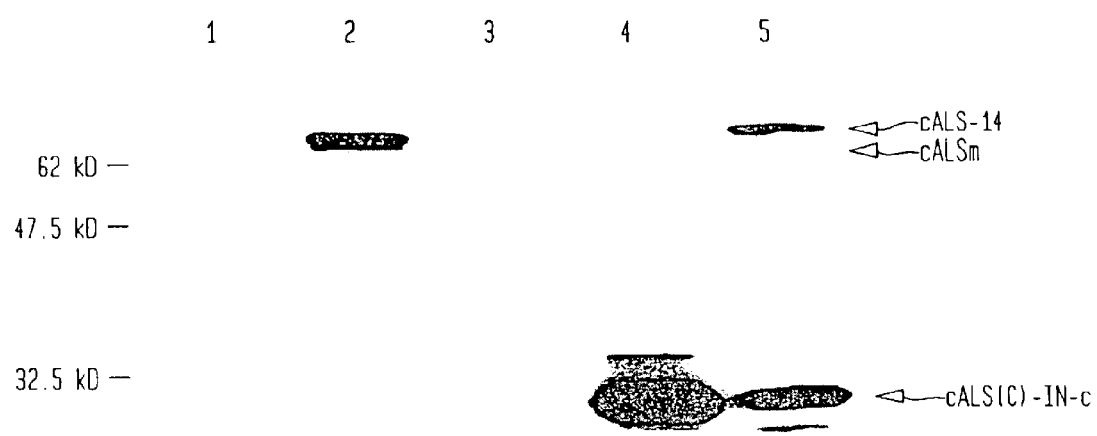

Both ALS-intein fusion fragments, cALS(N)—$IN_n$ and cALS(C)—$IN_c$, described in Section 3, were co-expressed in *E. coli* ER2744 under the same conditions as described in Example I, Section 6. A western blot was performed to detect the trans-splicing product (Method, see Example I, Section 6). On the blot, a fragment of 69 kD, which corresponds to the size of the wild type cALS (FIG. 10A and FIG. 10B, lane 2), was detected in both fusion proteins expressed cells and was recognized by rabbit antisera specifically raised against two peptides derived from N- and C-terminal sequence of maize ALS (FIG. 10A and FIG. 10B, lane 5). A non-specific protein reacting with antiserum against N-terminal of maize ALS was observed (FIG. 10A, lane 1 to lane 5). The peptides used to raise antibodies are 1) ALS-N peptide corresponding to the sequence from Lys66 to Ala85, $NH_2$-CKGADILVESLERCGVRDVFA-COOH (SEQ ID NO:22), and 2) ALS-C peptide corresponding to the sequence from Ile619 to Tyr638, $NH_2$-CI PSGGAFKDMILDGDGRTVY-COOH (SEQ ID NO:23). The full length cALS species was not detected in cells expressing either N- or C-terminal fusion protein (FIG. 10A and FIG. 10B, lane 3 and lane 4). This demonstrated that split maize ALS, like *E. coli* ALSII, when fused with the Ssp DnaE intein, was also able to perform trans-splicing to produce the full length ALS.

In conclusion, the maize ALS gene was split by the Ssp DnaE intein and cloned into two separate plasmid vectors. When both the fusion gene vectors were introduced into the same host cell and co-expressed, the two fusion proteins underwent trans-splicing to produce a full length cALS. Although a functional assay is needed to determine the activity of the spliced maize ALS protein in plants, it does raise the possibility of successfully splitting a plant herbicide resistant or disease resistant genes into two inactive gene segments. These two gene fragments can be confined into two separate cellular compartments, such as the chloroplast and nucleus, or two separate loci on the chromosomes, or two separate DNA vector. This novel mode of gene expression may greatly lessen the chance of spreading an intact active transgene into other species.

EXAMPLE III

The present Example details the feasibility of splitting the aroA gene and regenerating the desired protein activity using an intein. The experiment consisted of dividing the gene encoding the mutant aroA gene at various positions and fusing the gene encoding the N-terminal splicing domain of the Ssp DnaE intein ($IN_n$) to the gene encoding the N-terminal fragment of the EPSPS protein. Concurrently, the gene encoding the C-terminal splicing domain of the Ssp DnaE intein ($IN_c$) was fused to the gene encoding the C-terminal fragment of the EPSPS protein. When the fusion genes were placed on to two separate plasmids and co-transformed and co-expressed in the same bacterial cell it was demonstrated that those bacterial cells were resistant to the herbicide glyphosate.

The Cloning of *Salmonella typhimurium* aroA Gene That Confers Resistance to Glyphosate 1. Creation of plasmid pEPS#1

The *Salmonella typhimurium* aroA gene with the C301 to T mutation was acquired from the American Type Culture Center in the form of a cosmid in the bacteria *Salmonella choleraesuis* subsp *choleraesuis* (ATCC No. 39256). The modified aroA gene was amplified from the cosmid by the polymerase chain reaction using primers EPSP#1 (5'-GGATC CTAAGAAGGAGATATACCCATGGAATCC-CTGACGTTACA-3' (SEQ ID NO:24)) and EPSP#2 (5'-GTCGACGCTCTCCTGCAGTTAGGCAGGC GTACTCATTC-3' (SEQ ID NO:25). The PCR product was inserted into the StuI site of the plasmid LITMUS 28 (New England Biolabs, Inc., Beverly, Mass.). Following transformation and plasmid preparation, sequencing revealed an unexpected mutation (C103 to G) which was reverted using Stratagene's (La Jolla, Calif.) Quick Change Site Directed Mutagenesis Kit and primers EPSP#10 (5'-GCTTTGCTCCTGGCGGCTTTACCTTGTGGT AAAACCGC-3' (SEQ ID NO:26)) and EPSP#11 (5'-GCGGTTTTAC CACAAGGTAAAGCCGCCAGGA-GCAAAGC-3' (SEQ ID NO:27)). Sequencing of DNA from the resulting colonies revealed that the unexpected mutation had been reverted to the expected C. This plasmid was termed pEPS#8 and used as the acceptor plasmid in the subsequent transposition linker scanning reactions.

2. Description of ER2799, an *E. coli* strain used to test the aroA gene constructs An *E. coli* strain that has the aroA gene deleted from its chromosome was acquired from the Yale *E. coli* stock center (*E. coli* strain AB2829, CGSC#2829, ID#8215). This strain was made hsdR- and named ER2799. Because ER2799 lacks the aroA gene, which is necessary for aromatic amino acid synthesis, it does not grow on M9 minimal media. This strain is used to test the various aroA gene constructs to see if the new aroA gene can rescue the bacteria and allow growth on minimal media either in the presence or absence of glyphosate.

3. Finding a site to split the aroA target gene by transposon based linker scanning The first step in performing this experiment was to determine the sites in the 5-enolpyruvyl-3-phosphoshikimate synthetase (EPSPS) protein which could allow insertion of an intein in cis. In cis refers to the fact that the complete intein is inserted into the complete EPSPS protein. However, it was not known which portions of the EPSPS protein itself would be tolerant to extra amino acid residues. So to determine where the EPSPS protein could tolerate amino acid insertions a new technology, the GPS®-LS kit (available from New England Biolabs, Inc., Beverly, Mass.), was used to randomly insert 5 amino acid residues throughout the EPSPS protein sequence. An expression plasmid library was constructed with the EPSPS gene with the randomly inserted 5 amino acids. This library was transformed into E. coli strain ER2799 and applied to plates containing M9 minimal media. ER2799 lacks the aroA gene and will not grow on M9 minimal plates unless an active EPSPS gene is supplied by plasmid transformation. The ER2799 E. coli that grew following transformation with the library should contain an EPSPS protein that is active with the 5 amino acid insertion. These were sequenced to determine the position of the 5 amino acid insertion and 42 unique sites were discovered in the EPSPS protein that allowed growth of ER2799 on M9 minimal plates (FIG. 15). Furthermore, another 19 unique sites were found that did not tolerate a 5 amino acid insertion (FIG. 16).

4. Transposition Reaction

The reaction was performed by adding 6 µl of 20 ng/µl pEPS#8 (target DNA), 1.5 µl of 20 ng/µl PmeI donor DNA, 3 µl of distilled water, 3 µl of 10×GPS®-LS buffer and 1.5 µl of Tn*ABC and mixing for 15 min at 37° C. 1 µl of Start Solution was added and the reaction incubated at 37° C. for 1 hour and 20 min. The reaction was stopped by heat inactivation for 15 min at 75° C. Following cooling the reaction mixture to room temperature and dialysis against water for 2 hours the reaction mixture was transformed into freshly-made ER2685 (fhuA2 ginV44 el4-rfbD1? relA1? endA1 spoT1? thi-1 Δ(mcrC-mrr)114::IS10 Δ(lacI-lacA)200 F'proA+B+lacIq D1 (lacZ)M15 zzf:Tn10 (TetR)) cells by electroporation. The cells were incubated for 1 hour at 37° C. and then plated onto LB plates containing ampicillin and kanamycin. Cell growth was allowed to proceed at 37° C. overnight. It was discovered that 10 µl of reaction mixture gave over 10,000 colonies (enough to cover all possible transposon insertion sites, 2840 sites in pEPS#8, 3.3 times) following transformation.

5. Isolating the DNA fragment (3.0 kb) containing the EPSPS gene plus transposon All the transformants from the transposition reaction were recovered using LB medium and 66% of the cells were saved at −70° C. by adding 20% glycerol. The rest were grown in 500 ml of LB liquid medium containing 100 µg/ml ampicillin, and 50 µg/ml kanamycin at 37° C. overnight. The cells were harvested by centrifugation and the plasmid DNA was purified (508 µg total) using a Qiagen Midi kit (Qiagen, Studio City, Calif.). The 3.0 kb aroA gene-Transposon DNA fragment was released by digesting the DNA(58 µg) with PstI, NcoI and AhdI and isolated by gel-purification using agarase following ethanol precipitation (4 µg DNA was recovered).

6. Cloning the aroA gene-Transposon 3.0 kb fragment into the pCYB3 vector

The gel-purified 3.0 kb aroA gene-Transposon DNA fragment was ligated into the NcoI to PstI sites of pCYB3 (5.2 kb), and transformed into ER2685 by electroporation after drop dialysis for 2 hours. The electroporated cells were incubated for 1 hour in LB medium. 250 µl of this cell suspension was plated onto LB plates containing 100 µg/mL ampicillin and 50 µg/mL kanamycin while another 5.5 ml was inoculated into 1 liter of LB liquid medium with 100 µg/mL ampicillin and 50 µg/mL kanamycin and grown at 37° C. overnight. The plasmid DNA library containing the transposon within the aroA gene was isolated by Qiagen (Studio City, Calif.) Midi kit (750 µg).

7. Screening the library EPSPS protein that is active with the 5 amino acid linker 105 µg of the library DNA was digested with PmeI to remove the transposon from the aroA gene. This leaves 15 bases (or 5 amino acid residues) at the transposon insertion site. A 7 kb fragment was recovered (in a final volume of 400 µl EB), self-ligated (86 µl out of 400 µl 7 kb fragment in a 100 µl rxn), transformed (30 µl of the 100 rxn) into E. coli strain ER2799 and plated onto both LB and M9 minimal plates, each containing 100 µg/mL ampicillin In the presence of 0.3 mM IPTG. Following incubation at 37° C. overnight ca. 20% of the original cells survived on M9 minimal plates as compared to the LB plates. Individual colonies that grew on M9 minimal media plates were analyzed by DraI digestion and DNA sequencing to confirm the site of linker insertion site into the aroA gene.

42 different insertion sites were identified among 72 active Individual clones that can tolerate 5 amino acid residues inserted into the aroA gene and 19 different insertion sites were identified among 39 inactive clones that can not grow on M9 minimal media selection plates (see FIG. 15 and FIG. 16). Plasmids pCE-5-22, pCE-5-21, pCE-5-35 and pCE-5-23 were the active clones that have 5 amino acid residues incorporated into the EPSPS protein (aroA gene product) at positions 182, 215, 235 and 267, respectively. These four sites were chosen for further studies.

Construction of Ssp DnaE C is- and Trans-Splicing Vectors

1. Creation of vectors pCE182DnaE, pCE215DnaE, pCE235DnaE, and pCE267DnaE for Cis-Splicing This involved inserting an intein into the sites in the target protein that were discovered to tolerate 5 amino acid insertions.

Figure 11:
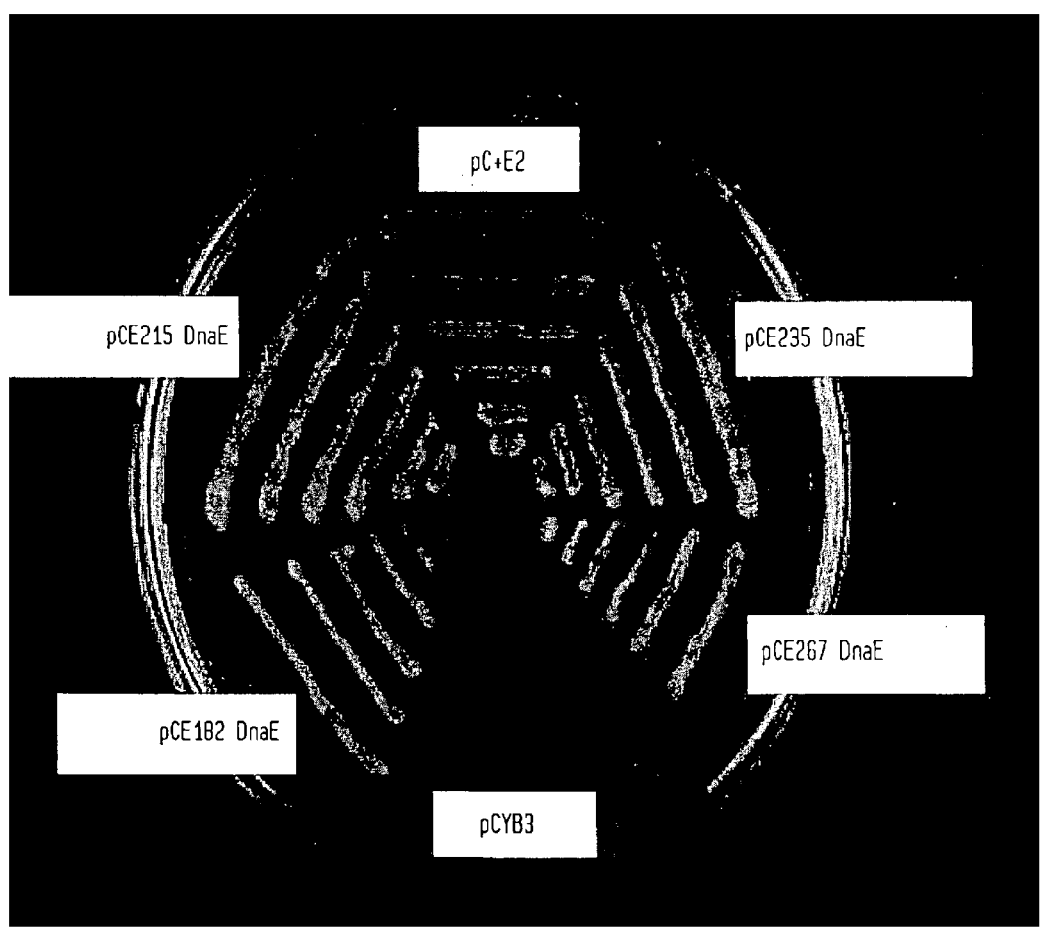
FIG. 11—Plating Assay for Ssp DnaE intein Cis-splicing Constructs. Plasmids pCE182DnaE, pCE215DnaE, pCE235DnaE, and pCE267DnaE encode for the 5-enolpyruvyl-3-phosphoshikimate synthetase (EPSPS) protein with the full length Ssp DnaE intein inserted at amino acid positions 182, 215, 235 and 267, respectively. These were transformed into ER2799 E. coli cells (which require the EPSPS protein for viability in M9 minimal media), and plated on M9 minimal plates. Following incubation at 37° C. overnight, individual clones on each plate were picked and stripped onto a single M9 minimal plate. This master plate was then incubated at 37° C. overnight or RT for 2–3 days. As a control the pCYB3 plasmid was used as it carries no EPSPS gene, and there is no growth on the selection plate. pC+E2, a plasmid which contains the full length wild type EPSPS containing a Pro101Ser mutation, grows on M9 selection plate and also confers glyphosate resistance.

Four sites were chosen for further study (positions 182, 215, 235, and 267). The full length Ssp DnaE Intein was inserted into these sites and the EPSPS-intein fusion was tested for its ability to permit ER2799 cells to grow on M9 minimal plates. All four sites were found to grow on M9 plates, indicating that the EPSPS protein could tolerate the intein inserted at these positions (see FIG. 11 and FIG. 14).

CE182 or CE215, which was the linear DNA of pCE-5-22 or pCE-5-21 with the exception that the five amino acid linker at 182 or 215 has been removed, was generated by polymerase chain reaction (PCR) from templates pCE-5-22 or pCE-5-21 using primers 5'-GCCCCTAAAG-ACACAATTATTCGCG-3' (SEQ ID NO:28) and 5'-CAGCGGCGCCGTCATCAGCAGAGCG-3' (SEQ ID NO:29) for CE182 or 5'-GCGAACCACCACTACCAA-CAATT TG-3' (SEQ ID NO:30) and 5'-TATCTCCACGCCAAAGGTTTTCATT-3' (SEQ ID NO:31) for CE215. The Ssp DnaE intein gene containing two native N-extein residues and three native C-extein residues was amplified by PCR from pMEB8 (Evans, et al., *J. Biol. Chem.*, 275:9091 (2000)) using primers 5'-GAATAT TGCCTGTCTTTTGGT-3' (SEQ ID NO:32) and 5'-GTTAAAGCAGTT AGCAGCGAT-3' (SEQ ID NO:33). The resultant PCR fragment was phosphorylated with T4 polynucleotide kinase, purified by QIAquick column (Qiagen, Inc., Studio City, Calif.) and ligated into CE182 or CE215 to generate pCE182DnaE or pCE215DnaE, respectively.

The Ssp DnaE intein gene containing four native N-extein residues and three native C-extein residues was amplified by PCR from pMEB8 using primers 5'-TGCTGAATATTG CCTGTCTTTTGG-3' (SEQ ID NO:34) and 5'-CCGTTAAAGCAGTTAG CAGCGATAGC-3' (SEQ ID NO:35). The resultant PCR fragment was purified by QIAquick column (Qiagen Inc., Studio City, Calif.) and ligated into the gel-purified, PmeI cut pCE-5-35 or pCE-5-23 vector DNA to generate pCE235DnaE or pCE267DnaE, respectively.

2. Creation of vectors p215EN2/pEPS#28 and p235EN2/pEPS#29 for Trans-Splicing:

Two plasmids were constructed with compatible origins of replication. The N-terminus of the appropriate EPSPS protein was fused to the N-terminus of the N-terminal Ssp DnaE splicing domain ($IN_n$) and inserted into one plasmid. The remaining C-terminal portion of the appropriate EPSPS protein was fused to the C-terminus of the C-terminal splicing domain of the Ssp DnaE intein ($IN_c$). This fusion was inserted into the second plasmid. The plasmids were co-transfected into ER2799 by electroporation. Expression of the fusion protein was under the control of an IPTG Inducible pTac promoter. The transformed cells grew on M9 minimal plates, liquid M9 minimal media, or liquid M9 minimal media supplemented with glyphosate (FIGS. 11, 12, 13 and 14). This indicated that the protein halves could generate an active EPSPS protein when co-expressed in the same cell.

The 0.6 kilobase XhoI to PstI fragment of pMEB4 was gel-purified using the QIAquick extraction kit and ligated into the XhoI to PstI sites in the pCYB3 (New England Biolabs, Inc., Beverly, Mass.) vector to generate pCEN1. The NcoI site between the Ssp DnaE intein and the chitin-binding domain (CBD) was removed by PacI and SapI digestion of pCEN2 followed by T4 DNA polymerase treatment and self-ligation to generate plasmid pCEN2. This vector contains the N-terminal 123 amino acid residues of the Ssp DnaE intein ($IN_n$) under the control of pTac promoter and confers resistance to ampicillin.

p215EN2 or p23SEN2 were constructed by ligating the NcoI to KpnI fragment of pCE21SDnaE or pCE235DnaE into the same sites of pCEN2. p215EN2 or p235EN2 has the N-terminus of EPSPS (residues 1–215 for p215EN2, 1–235 for p235) fused to the $IN_n$.

The NcoI to FspI fragment of pCYB3 was ligated into the NcoI to DraI sites of pKEB1 to generate pKEB12 (NEB#1282). A sample of pKEB12 plasmid transformed in *E. coli* strain ER2566 has been deposited under the terms and conditions of the Budapest Treaty with the American Type Culture Collection on May 23, 2000 and received ATCC Patent Deposit Designation No. PTA-1898. This vector has the C-terminal 36 amino acid residues of the Ssp DnaE intein ($IN_n$) fused to CBD and confers resistance to kanamycin.

pEPS#28 and pEPS#29 were constructed by ligating the BglII to PstI fragment of pCE21SDnaE and pCE23SDnaE into the same sites of pKEB12. pEPS#28 or pEPS#29 has the C-terminus of EPSPS (residues 216–427 for pEPS#28, 236–427 for pEPS#29) replacing the CBD In pKEB12 and attached to the C-terminus of $IN_c$.

3. Creation of the EPSPS complementary construct pEPS#34 and pEPS#36.

When the EPSPS protein fragments, lacking the intein domains, were co-expressed in ER2799 cells, the cells failed to grow on M9 minimal plates, liquid M9 minimal media, or liquid M9 minimal media supplemented with glyphosate (FIG. 12 and FIG. 13). This indicated that EPSPS activity was absolutely dependent on the presence of both intein halves.

DNA encoding the N-terminus of the EPSPS protein, residues 1–235, (EPS235N) was amplified by PCR from pCE235DnaE using primers 5'-GGATCCTAAG- AAG-GAGATATACCC ATGGAATCCCTGACGTTACA-3' (SEQ ID NO:36) and 5'-GATATC CTGCAGTT-AACCTGGAGAGTGATACTGTTGACC-3' (SEQ ID NO:37). The resultant PCR product was purified using a QIAquick PCR kit, digested with NcoI and PstI, purified from an agarose gel using the QIAquick extraction kit and ligated into the NcoI to PstI sites of plasmid pCYB3 to generate pEPS#34.

Plasmid pEPS#36 was created by amplifying DNA encoding the C-terminus of EPSPS, residues 236–427, (EPS235C) by PCR from pC+E2 using primers 5'-GATATCCCATG GGACGCTATCTGGTCGAGGGCGATG-3' (SEQ ID NO:38) and 5'-GT CGACGCTCTCCTGCAGTTAGG-CAGGCGTACTCATTC-3' (SEQ ID NO:39). The resultant PCR product was purified using the QIAquick PCR kit, digested with NcoI and PstI, purified from agarose gel and ligated into the NcoI to PstI sites of plasmid pKEB12. Two extra residues Met-Gly were also incorporated at the N-terminus of EPS235C due to the NcoI site for cloning.

4. Creation of Vectors Containing the C is or Trans "dead" Ssp DnaE intein at position 235 (pEPS#31, pEPS#33, pEPS#37).

Interestingly, trans-splicing was not required for activity, because if three of the most highly conserved catalytic residues of the Ssp DnaE intein were changed to alanine the co-transformed ER2799 cells still grew. This event demonstrates that the intein can act as an affinity domain to bring the two EPSPS intein fragments together (FIG. 12 and FIG. 13).

The Ssp DnaE intein gene containing four native N-extein residues and three native C-extein residues was amplified by PCR from pMEB8 using primers 5'-TGCTGAATATGC GCTGTCTTTTGGTACCGAA-3' (SEQ ID NO:40) and 5'-CCGTTAAA CGCCGCAGCAGCGATAGCGCC-3' (SEQ ID NO:41). The resultant PCR fragment was purified by QIAquick column (Qiagen Inc., Studio City, Calif.) and ligated into the PmeI site of plasmid pCE-5-35 to generate pEPS#31. This Ssp DnaE intein contains three mutations, Cys1→Ala/Cys+1→Ala/Asn159→Ala, in the catalytic residues that eliminates its spicing activity.

5. Methods of Assaying EPSPS Activity

Plating assay for EPSPS activity. The presence of a functional EPSPS protein could be determined in vivo using *E. coli* strain ER2799, which lacks an endogenously active EPSPS (see above). ER2799 cells alone fail to grow on M9 minimal plates (supplemented with 0.3 mM IPTG). In the following description when M9 minimal plates are mentioned they also contain 0.3 mM IPTG. Plasmid pC+E2, which contains the full length wild type EPSPS gene with a C301 to T mutation, is able to rescue growth of ER2799 on the M9 minimal plates when introduced by transformation.

Assaying the Ssp DnaE cis-splicing constructs. Plasmids pCE182DnaE, pCE21SDnaE, pCE235DnaE, pCE267DnaE (0.05 μg of each) were transformed into *E. coli* ER2799 cells by electroporation (Sambrook, et al., *Molecular Cloning: A Laboratory Manual*, 2$^{nd}$ Edition, Cold Spring Harbor Laboratory, NY: Cold Spring Harbor Laboratory Press (1989)), see FIG. 11. 0.8 mL of LB media was added to the transformed cells and these were incubated at 37° C. for 1 hour with shaking. 200 μL of this solution was plated onto either LB or M9 minimal plates supplemented with 0.1 mg/mL ampicillin (Sambrook, et al., *Molecular Cloning: A Laboratory Manual*, 2$^{nd}$ Edition, Cold Spring Harbor Laboratory, NY: Cold Spring Harbor Laboratory Press (1989)). The plates were incubated for varying length of time and at various temperatures. The most commonly used being overnight at 37° C.

Assaying the Ssp DnaE trans-splicing constructs. The activity of each EPSPS trans construct was assayed by co-transforming the constructs to be tested into ER2799 and plating on either an M9 minimal plate, containing 0.3 mM IPTG, or an LB plate in which both were supplemented with 0.1 mg/mL ampicillin and 0.05 mg/mL kanamycin. In cases where only one plasmid contained the EPSPS gene or a portion of the EPSPS gene the complementary antibiotic resistance was supplied by co-transforming the *E. coli* with either pCYB3 or pKYB1 (New England Biolabs, Beverly, Mass.), which has no EPSPS gene present.

The plasmids used were: pC+E2, p215EN2, p235EN2, pEPS#28, pEPS#29, pEPS#33, pEPS#37, pEPS#34, and pEPS#36. These plasmids were co-transformed (Sambrook, et al., *Molecular Cloning: A Laboratory Manual*, 2$^{nd}$ Edition, Cold Spring Harbor Laboratory, NY: Cold Spring Harbor Laboratory Press (1989)) using 0.1 μg of the appropriate plasmids, in various combinations, into ER2799 *E. coli* cells, and plated on both LB plates and M9 minimal media plates, each containing 100 μg/mL ampicillin and 50 μg/mL kanamycin. The M9 minimal plate also contained 0.3 mM IPTG. Individual clones were picked from each LB plate and stripped on one M9 minimal media selection plate following incubation at 37° C. overnight or RT for 2–3 days. The combinations used were: WT, pC+E2 and pKYB1 (New England Biolabs, Beverly, Mass.); 215NC, p215EN2 and pEPS#28; 215C, pEPS#28 and pCYB3; 235NC-Dead, pEPS#33 and pEPS#37; 235NC, p235EN2 and pEPS#29; 235N, p235EN2 and pKYB1; 235C, pEPS#29 and pCYB3; 235N-215C, p235EN2 and pEPS#28; and 235 complement, pEPS#34 and pEPS#36 (see FIG. 12).

Determination of ER2799 growth in liquid culture in the presence or absence of glyphosate. The testing of glyphosate resistance for the 235 trans constructs was made using plasmid combinations as follows; WT, pC+E2 and pKYB1; 235NC-Dead, pEPS#33 and pEPS#37; 235NC, p235EN2 and pEPS#29; 235N, p235EN2 and pKYB1; 235C, pEPS#29 and pCYB3; and 235 complement, pEPS#34 and pEPS#36. These plasmids were co-transformed into ER2799 *E. coli* cells as described above and plated onto LB plates containing 100 μg/mL ampicillin and 50 μg/mL kanamycin. As a control, pCYB3/pKYB were co-transformed into *E. coli* strain ER2744, and plated on an LB plate containing 100 μg/mL ampicillin and 50 μg/mL kanamycin. A preculture was prepared for each transformation by inoculating the fresh colony into LB medium supplemented with 100 μg/mL ampicillin and 50 μg/mL kanamycin at 30° C. for overnight. Equal amounts of pre-culture (10–11 μL depending on the cell density) was inoculated into freshly-made M9 minimal medium containing 100 μg/ml of ampicillin, 50 μg/ml of kanamycin and 0.3 mM IPTG in the absence or presence of different amounts of glyphosate. The growth of each construct was measured by OD at 600 nm, see FIG. 13.

Growth of the cis 235 construct in M9 liquid minimal media. Two plasmid vectors one with a splicing competent Ssp DnaE intein (235 cis) and another with a splicing incompetent intein (235 dead), pCE235DnaE and pEPS#31, respectively, were transformed into separate ER2799 *E. coli* cells and plated on LB plates supplemented with 100 μg/mL ampicillin and 50 μg/mL kanamycin. A preculture was prepared for each transformation by inoculating the fresh colony into LB medium supplemented with 100 μg/mL ampicillin and 50 μg/mL kanamycin at 30° C. for overnight. Equal amounts of pre-culture (10–11 μL depending on the cell density) was inoculated into freshly-made M9 minimal medium containing 100 μg/ml of ampicillin, 50 μg/ml of kanamycin and 0.3 mM IPTG. The cell density was determined at various times using the OD at 600 nm (see FIG. 14).

The NcoI to KpnI fragment of pEPS#31 was ligated into the same sites in plasmid pCEN2 to generate pEPS#33. Plasmid pEPS#37 was created by cloning the BglII to PstI fragment of pEPS#31 into the same sites in plasmid pKEB12.

EXAMPLE IV

Trans-Splicing of Two Unrelated Gene Products Aminoglycoside-3-Acetyltransferase (aadA) and Soluble Modified Green Fluorescent Protein (smGFP), to Give Rise to a Functional Hybrid Protein in *E. coli*

Aminoglycoside-3-acetyltransferase gene was fused to Ssp DnaE intein N-fragment ($IN_n$). The C fragment of the Ssp DnaE intein ($IN_c$) was fused to the smGFP gene. The fusion proteins could be translated as individual polypeptides from the respective constructs. These fusion protein coding DNA sequences were cloned into either pIH976 (FIG. 17) or pAGR3 (FIG. 18) plasmids. Both the plasmids (pIHaadE-N (pIH976 containing aadA and $IN_n$ terminal) and pAGRE-CsmGFP (pAGR3 containing $IN_c$ and smGFP)) were co-transformed in to *E. coli* (FIG. 19A). The trans-formed *E coli* were resistant to spectinomycin/streptomycin sulfate (FIG. 19B). The cell extracts were made after 16 hrs of growth. The proteins in the extract was separated on SDS tris glycine gel and blotted on to a PVDF membrane. This membrane was probed with anti GFP monoclonal antibodies. Trans-splicing was observed in *E. coli* extracts, where both the plasmids were introduced. As a result of trans-splicing the fusion product had a molecular mass identical with the calculated cumulative mass of both the proteins (FIG. 19C).

The following protocol describes the production of cassettes, pIHaadE-N (Aminoglycoside-3-acetyltransferase gene fused to DNA encoding $IN_n$), pAGRE-CsmGFP (DNA encoding $IN_c$ was fused to smGFP gene), Western blotting and detection.

Polymerase chain reaction (PCR) was used for cloning of the open reading frames (ORFs) in to the desired plasmids. The reaction contains Vent® DNA polymerase buffer supplemented with 2 mM magnesium sulfate, 200 μM dNTPs, 1 μM of each primer and 100 ng plasmid DNA in a total volume of 50 μl with 2 units of Vent® DNA polymerase. Between 10 to 20 rounds of amplification were carried out using a Perkin-Elmer gene amp PCR 2400 system (Emeryville, Calif.). The following primers used for amplification of the aadA gene (aadA forward primer: GCCTTAATTAACCATGAGGGAAGCGGTGATCGC CG (SEQ ID NO:47), aadA reverse primer: TGCGGTC-GACTTTGC CGACTACCTTGGTGATCTC (SEQ ID NO:48). PCR products were purified using a PCR purification kit (QIAquick PCR purification) from Qiagen (Valencia, Calif.). Purified PCR products were digested by Pac I and Sal I restriction enzymes and cloned in to pNEB193 (New England Biolabs, Inc., Beverly, Mass.) plasmid. The clone containing the aadA gene was named pNEBaad3. Similar protocol was used for amplification and cloning of the smGFP gene using specific primers (smGFP forward primer: CCCAAGCTTGGCGCCATGAGTAAAG-GAGAAGAACTTTTCAC (SEQ ID NO:49) and smGFP reverse primer; GCGACCGGTTTATTTGTATAG TTCATCCATGCCATG (SEQ ID NO:50) into pLITMUS 28 (New England Biolabs, Inc., Beverly, Mass.). The clone containing the smGFP gene was named psmGFP7. Sequences for both aadA and smGFP genes were verified by DNA sequencing.

The intein from the dnaE gene of *Synechocystis* species PCC6803 was PCR amplified. The amino terminal part of the intein (amino acids 1–123) is referred to as $IN_n$ and the carboxy terminal as $IN_c$ (amino acids 124–159). Both $IN_n$ and $IN_c$ fragments were cloned into pLITMUS 28 and pNEB193 respectively. The primer pairs for amplification of $IN_n$ and $IN_c$ are listed ($IN_n$ forward primer: AGGGAAT-TCGTCGACAAATTTG CTGA ATATTGCCTGTCT (SEQ ID NO:51), $IN_n$ reverse primer: GGCCTCGAGTTATT-TAATTGTCCCAGCGTCAAGTAATG (SEQ ID NO:52), $IN_c$ forward primer: AGCTTTGTTTAAACCATGGT-TAAAG TTATCGGTCGTAGATC (SEQ ID NO:53), $IN_c$ reverse primer: CAGCGTCGACGGCGCCGTGG-GATTTGTTAAAGCAGTTAGCAGC (SEQ ID NO:54)). The plasmids containing the $IN_n$ and $IN_c$ fragments were pLitDnaE-N1 and pNEBDnaE-C2 respectively.

Fusion constructs of intein fragments and either aadA or smGFP gene products were made in the following way: BamHI and SalI fragment (800 bp) from pNEBaad3 was ligated into BamHI-SalI digested pLitDnaE-N1 to give rise to pAEN1. In a similar way, the 150 bp insert (pNEBIN-c digested with PstI and KasI) was ligated into PstI and KasI digested pLit SmGFPS to give rise to pGFPEC. Plasmid pAEN contains aadA gene in frame with $IN_n$ and pGFPEC contain smGFP gene in frame with $IN_c$.

The fused genes were PCR amplified and cloned into *E. coli* expression vectors. The inserts of pAEN and pGFPEC were cloned into pIH976 (NcoI and SacI site) and pAGR3 (EcoRI and SacII sites) vectors. The primers are listed (aadA-$IN_n$ forward primers: CATGCCATGGGGGAAGCG-GTGATCGC CGAAG (SEQ ID NO:55), aadA-$IN_n$ reverse primers: ACGCG AGCTCTTATTTAATTGTCCCAGCGT-CAAGTAATG (SEQ ID NO:56), $IN_c$-smGFP forward primer: CGAATTCTATGGTTAAAGTTATCGG TCGTA-GATC (SEQ ID NO:57), $IN_c$-smGFP reverse primer: AG CCCGCGGTTATTTGTATAGTTCATCCATGCCATG (SEQ ID NO:58)). The *E. coli* expression plasmids were pIH976-aadE-N and pAGR-$N_c$-smGFP, under the control of Ptac promoter of the host. Either of the plasmids or both together were transformed into *E. coli* ER1992 (New England Biolabs, Inc., Beverly, Mass.) and plated on LB agar-Ampicillin plates as well as LB agar ampicillin and spectinomycin plates.

For Western blotting, *E. coli* cell extracts were mixed with SDS loading dye with 1 mM DTT, boiled at 95° C. for 5 min and loaded on a 10–20% Tris-glycine-SDS gradient gel. The proteins were blotted on an Immobilin-P membrane and probed with an anti-GFP monoclonal antibody (Roche Molecular Biochemicals, Indianapolis, Ind.) followed by chemiluminescent detection of the GFP and aadA-GFP fusion protein.

EXAMPLE V

Utilization of Plant Promoters in *E. coli* for Trans-Splicing of Two Unrelated Gene Product, Aminoglycoside-3-Acetyltransferase (aadA) and Soluble Modified Green Fluorescent Protein (smGFP) to Give a Functional Hybrid Protein The above DNA fragments were cloned downstream of the chloroplast specific promoter PpsbA (SEQ ID NO:59). A terminator sequence of the same gene (TpsbA (SEQ ID NO:60) was placed down stream of the cloned gene. The two genes were expressed in opposite direction to avoid read through. The plant promoters were functional upon transformation in to *E. coli* and trans-spliced products (aadA-smGFP fusion protein, 57 kDa) were observed in Western blot assay using anti GFP antibodies. Thus chloroplast specific promoters are functional in *E. coli* and could be used for gene expression studies.

The following protocol describes the production of a *E. coli* plant shuttle vector (pNCT114/pNCT224) that is capable of homologous recombination of a transgene(s) in vivo.

A shuttle vector consists of elements that will make it functional in both *E. coli* as well as plant cell. Plasmid pLITMUS28 (New England Biolabs, Inc., Beverly, Mass.) is the backbone for the pNCT114 and pNCT224 gene targeting vector. The vector DNA comprises, at least (1) two DNA sequence homologous to the plastid genome (also referred as targeting sequence/fragment), (2) one or more promoter element, (3) transcription terminator elements, and (4) one or more selectable/drug resistance (non-lethal) marker gene.

Promoter element (PpsbA) DNA sequences were PCR amplified from genomic DNA extracted from 7 days old tobacco seedlings using the CTAB method as described by Murray and Thompson (Nucleic Acids Res., 8:4321–4325 (1980). The primers used for amplification are listed (PpsbA forward primer: AACTGCAGGAATAGATCTACATA-CACCTTGG (SEQ ID NO:64), PpsbA reverse primer: CCGCTCGAGCTTAATTAAGGTAA AATCTTGGTT-TATTTAATC (SEQ ID NO:65)). Similarly the terminator sequence (TpsbA) was amplified by PCR and cloned. The primers used for amplification are listed (TpsbA forward primer: GCGACCGGTGATCCTGGCCTAGTCTAT-AGGAGG (SEQ ID NO:66), TpsbA reverse primer: AGGC-CTAGGAGAATACT CAATCATGAATAAATGC (SEQ ID NO:67)). A vector with a psbA promoter and terminator DNA sequence allows genes to be cloned in between these for expression of the protein. The targeting DNA sequences were amplified and inserted outside of the promoter and terminator in a flanking manner (FIG. 20), thus facilitating homologous recombination of the trans-gene at a predetermined loci. pNCT114 contains 16SrDNA-trnaV and rps7/12 targeting sequence (SEQ ID NO:61), whereas, pNCT224 contains orf228-ssb as left border and orf1244 as right border (SEQ ID NO:62). The following primers were used for PCR amplification of the targeting sequences.

Primers for pNCT114
Left border forward primer:
TTGGCGCGCTTGACGATATAGCAATTTTGCTTGG
(SEQ ID NO:68)
Left border reverse primer:
TTGCGTACGATTTATCTCAGATTAGATGGTCTAG
(SEQ ID NO:69)
Right border forward primer:
TTGCCTAGGCGTATTGATAATGCCGTCTAACCAG
(SEQ ID NO:70)
Right border reverse primer:
AGGGGTACCGAATTCAAGATTCTAGAGTCTAGAG
(SEQ ID NO:71)
Primers for pNCT224
Left border forward primer:
TTGGCGCGCAATTCACCGCCGTATGGCTGACCGG
(SEQ ID NO: 72)
Left border reverse primer:
TTGCGTACGCCTTTGACTTAGGATTAGTCAGTTC
(SEQ ID NO:73)
Right border forward primer:
TTGCCTAGGGTCGAGAAACTCAACGCCACTATTC
(SEQ ID NO:74)
Right border reverse primer:
AGGGGTACCATCACGATCTTATATATAAGAAGAAC
(SEQ ID NO:75)

A detailed diagram for pNCT114/224 is in FIG. 20A. Both the plasmids contain two promoters and two terminator DNA fragments. For directional cloning, unique restriction enzyme sites are incorporated. Plasmid pNCT114 and pNCT224 have unique restriction enzyme sites (PmeI-AgeI and PacI-XhoI sites). Insert from plasmid pAEN (aadA gene in frame with $IN_n$) was obtained by digesting with PacI-XhoI and pGFPEC (smGFP in frame with $IN_c$) was obtained by digesting with PmeI-AgeI and ligated sequentially into pNCT114 or pNCT224. The plasmids are designated as p115ag and p225ag (FIG. 21A). The plasmids were transformed into *E. coli* and selected with ampicillin and spectinomycin (FIG. 218B). The cell extracts were made from overnight cultures and separated on 10–20% Tris-glycine-SDS gradient gel. The proteins were blotted on an Immobilin-P membrane and probed with an anti-GFP monoclonal antibodies (Roche Molecular Biochemicals, Indianapolis, Ind.) followed by chemiluminescent detection of the GFP and aadA-GFP fusion proteins (FIG. 21C).

EXAMPLE VI

Cis-Splicing of the EPSPS and ALS Gene Products in Plant Cytoplasm Expressed from a DNA Cassette Integrated into Molecular DNA The introduction of DNA into plant nuclei has been achieved in many different ways, such as, electroporation, polyethylene glycol mediated, *Agrobacterium* mediated, microinjection and biolistic transformation. In accordance with the present invention, one should determine if the plant cytoplasm will mediate protein-splicing event in cis or trans. This will be a prerequisite for further trans-splicing technologies in plants. This technique will be useful if the target protein needs specific cytoplasmic modification for activity. Either of the above techniques may be employed to introduce the EPSPS and/or ALS gene cassettes into tobacco or any other suitable plant tissue or cells. The general cassette consists of: (1) Drug selection/degrading marker gene such as kanamycin or any other suitable selection marker; (2) a strong promoter element such as 35sCMV (cauliflower mosaic virus); and (3) right and left border T DNA repeats of *Agrobacterium*. Such a cassette could be introduced into plants either by a biolistic process or by *Agrobacterium* mediated gene transfer Horsch, et al., *Science* 227:1229–1231 (1985)). The cassette is based on pBI121 gene transfer vector (Jefferson, et al., *EMBO J.*, 6:3901–3907 (1987)). The design of the final cassette is illustrated in FIG. 22.

In the biolistic process, the transforming DNA is coated on the surface of fine gold particles and introduced into the plant cell by a particle accelerator gun (PDS1000/He gun, Biorad, Richmond, Calif.). For *Agrobacterium* mediated gene transfer the transforming DNA cassette is introduced into the bacteria. The *Agrobacterium* harboring the cassette is allowed to be in contact with a disk or tissue section from tobacco or other suitable plant leaves. This facilitates the transfer of the DNA cassette to the plant nuclei. In either of the above approaches, the DNA finally gets integrated into the plant nuclei. The putative transformed cells are used for marker gene (drug) selection. The plants regenerated in presence of the selected drugs are strong transgenic candidates. After the plants are mature, the cell extracts will be taken and mixed with SDS loading dye with 1 mM DTT, boiled at 95° C. for 5 min and loaded on a 10–20% Tris-glycine-SDS gradient gel. The separated proteins will be blotted on an Immobilin-P membrane and probed with an anti-ALS or EPSPS antibody. PCR may then be performed to determine if the gene has integrated in a predictable fashion without rearrangement.

This technique would be useful for proteins that need specific modification for activity/folding in cytoplasmic environment. A part of the target protein gene with necessary transport signal and splicing elements will be placed in an organelle for cytoplasmic transport in the form of a precursor polypeptide.

These plants are allowed to grow in the greenhouse till they mature and the seeds will be collected. The collected seeds are then germinated and F1 plants tested for herbicide resistance. A small-scale trial may be done to see whether or not the segregation pattern of the introduced transgenes follows a Mendelian inheritance pattern. Integration into nuclear DNA would yield Mendelian inheritance, whereas integration into chloroplast DNA woule yield non-Mendelian maternal inheritance.

EXAMPLE VII

Trans-Splicing of a Split Gene, Such as EPSPS/ ALS or of Two Unrelated Gene Products, Such as Aminoglycoside-3-Acetyltransferase (aadA) and Soluble Modified Green Fluorescent Protein (smGFP), to Give a Functional Hybrid Protein in Plant Chloroplast The aim of these experiments is to investigate if transsplicing is feasible in plant chloroplasts. Plant chloroplasts are similar to bacteria with respect to their transcription and translation machinery. In Examples IV–VI, we have used the naturally occurring intein from the dnaE gene of the *Synechocystis* species PCC6803, which is a *cyanobacterium*. *Cyanobacteria* are photosynthetic bacteria which are similar to plant chloroplasts. Thus it should be possible for inteins to splice or trans-splice in plant chloroplasts. These proposed experiments are in two sections: Section 1, To demonstrate the trans-splicing event of two unrelated gene products aadA and smGFP in plant chloroplasts, where both genes are integrated in chloroplast genome; and Section 2, Trans-splicing in chloroplast, where the smGFP gene cassette is integrated into the nuclear genome and the translated protein containing a transit peptide (rubisco 3A-$IN_c$-smGFP) is imported into the chloroplast for the reaction to proceed. The chloroplast will have aadA gene fused to $IN_n$ fragment. The detailed protocol is narrated below.

To demonstrate trans-splicing of two unrelated gene products, aminoglycoside-3-acetyltransferase (aadA) and soluble modified green fluorescent protein (smGFP) in chloroplast, upon transcription and translation in chloroplasts.

The plasmids are designated as p115ag and p225ag as in Example V. These plasmids will be delivered into plant organelles using a biolistic device. Tobacco or any other suitable plant tissue will be harvested aseptically from sterile greenhouse grown plants or tissue culture plant cells. Plant tissue will be equilibrated overnight with plant growth medium and sorbitol or any other suitable osmoticum. The plant cells will be bombarded with the above plasmids coated on gold particles. After a suitable recovery time the cells will be placed on plant growth medium along with phytohormone and spectinomycin sulphate 500µg/ml. The spectinomycin resistant callus tissue will be harvested and will be placed on shoot differentiation medium. When shoots are about 2 cm length they will be dissected out and put in the rooting medium. The transgenic plant or sector of the plants will be identified by hand held UV lamp (a normal (non-transgenic) plant will fluorescent red in UV, whereas, a transgenic plant will look green). The transgene integration and copy numbers will be verified by Southern blot analysis and PCR. The transgenic sectors will be tested for trans-splicing of aadA and smGFP using anti GFP antibody. These sectors would further be used for generating a pure trans-plastomic line. The F1 plants will be tested for spectinomycin resistance.

Trans-splicing in the chloroplast. The smGFP gene cassette is integrated into the nuclear genome and the translated protein containing the transit peptide of the rubisco 3A-$IN_c$-smGFP Is imported into the chloroplast for the reaction to proceed.

This method will enable any split protein (e.g., EPSPS or ALS) to be expressed as fused proteins with either $IN_n$ or $IN_c$ either in chloroplasts or the nucleus. The nuclear-encoded component will be fused to a chloroplast transit peptide to facilitate its migration into the chloroplast after translation in the cytoplasm. A detailed method for aadA and GFP is given below. Similar methods could be followed for any other protein/split genes.

This method will require a nuclear transformation vector, such as pBI121, carrying a drug selection marker and the target gene of interest. Our experimental gene will be a three part fusion protein with rubisco transit peptide followed by $IN_c$ and smGFP (in place of smGFP another protein/peptide such as half of EPSPS or ALS could be substituted). The transit peptide is codon optimized for tobacco (FIG. 26). This fusion gene will be under the control of a strong plant promoter, 35SCMV. A diagram of such cassette is shown (FIG. 23). This DNA will be introduced into the plant nucleus. The stable transgenic lines will be selected and F1 progeny will be tested for transgene integration.

Leaf sections from the above transgenic plants will be used for chloroplast DNA transformation. The chloroplast gene targeting vectors are based on p114 and p224 with spectinomycin resistance gene and a PpsbA promoter to drive the transgene. The transgenes could be the other half of the protein (that was introduced to the nuclear genome previously) with the necessary splicing elements. As a model system we would use the aadA-$IN_n$ fusion gene for chloroplast transformation. The transplastomic lines will be selected using both drugs (e.g., the chloroplast specific drug spectinomycin and the nuclear specific drug kanamycin). PCR and Western blot analysis will further establish pure plant lines.

For the transgenic plants the F1 generation will be tested for: (1) Mendelian inheritance pattern of the transgene/segment; (2) stability of the transgene; and (3) possible escape of the transgene through pollen.

ALS/EPSPS transgenic plants will be tested for resistance to sulphonyl urea and Roundup®.

It should be understood that the Examples and embodiments described herein are for illustrative purposes only and that various modifications or changes in light thereof will be apparent to persons skilled in the art and are to be included within the spirit and purview of this Application and the scope of the appended claims.

What is claimed is:

1. A method of reconstituting a target protein from protein fragments in a plant, comprising:
   (a) splitting a gene encoding a target protein into at least two DNA fragments;
   (b) separating the DNA fragments of step (a) to prevent transmission of the gene to other plants; wherein one of the DNA fragments coding for a portion of the target protein is compartmentalized in the nucleus, and the other DNA fragment coding for another portion of the target protein is compartmentalized in the chloroplast;
   (c) expressing the DNA fragments of step (b) within the plant to produce the corresponding fragments of the target protein; and (d) reconstituting the target protein from the protein fragments in the plant.

2. A method of preventing transmission to a second plant of a gene coding for a target protein in a first plant, comprising:

(a) splitting the gene encoding the target protein into at least two DNA fragments; and (b) separating the DNA fragments of step (a) wherein one of the DNA fragments coding for a portion of the target protein is compartmentalized in the nucleus of a host cell in the first plant, and the other DNA fragment coding for another portion of the target protein is compartmentalized in the chloroplasts of the host cell; and (c) preventing transmission of the gene coding for the target protein to the second plant.

3. A method according to claim 1, wherein at least one of the DNA fragments is fused to a DNA sequence encoding a transit peptide for transport into a chloroplast or nucleus.

4. The method of claim 1 or 2, wherein at least one of the DNA fragments is fused to a DNA coding for an intein or portions thereof.

5. The method of claim 4, wherein one of the DNA fragments is formed by linking a 5' end of the DNA fragment coding for an N-terminal portion of the target protein to a 3' end of the DNA coding for an N-terminal portion of the intein, and another of the fusion fragments is formed by linking a 5' terminal end of DNA encoding a C-terminal portion of the target protein to the 3' end of DNA coding for a C-terminal portion of the intein.

6. The method of claim 1 or 2, wherein the DNA coding for the target protein is split to form two or more DNA fragments by means of a DNA coding for one or more affinity domains.

7. The method of claim 6, wherein the affinity domain is selected from the group consisting of inteins or intein fragments, leucine zipper and c-Jun/c-Fos.

8. The method of claim 4, in which at least one of the DNA fragments coding for the target protein is fused to a DNA sequence encoding a transit peptide such that the protein product of the DNA fragment is transported into a single compartment where functional reconstitution can occur.

9. The method of claim 4, wherein reconstitution of the target protein fragments comprises intein-mediated splicing.

10. The method of claim 4, wherein reconstitution of the target protein fragments comprises intein-mediated protein complementation.

11. The method of claim 1, wherein reconstitution of the target protein fragments comprises protein complementation.

12. The method of claim 11, wherein protein complementation occurs in the presence of an affinity domain.

13. The method of claim 11, wherein protein complementation occurs in the absence of an affinity domain.

14. The method of claim 1 or 2, wherein splitting of the gene comprises:

(a) determining one or more potential split site regions of the target protein; and (b) splitting the DNA coding for the target protein at the potential split site region.

15. The method of claim 14, wherein the potential split site region of the target protein is determined by analyzing primary amino acid sequence of the target protein for non-conserved regions.

16. The method of claim 14, wherein the potential split site region is determined by linker tolerance of linker insertion within the target protein.

17. The method of claim 14, wherein the potential split site region is determined by analyzing the structure of the target protein for the presence of flexible loops.

18. The method of claim 14, wherein the potential split site region is determined by analyzing the structure of the target protein for the presence of amino acid sequence between folding domains of the target protein.

* * * * *

SEQUENCE LISTING

<160> NUMBER OF SEQ ID NOS: 134

<210> SEQ ID NO 1
<211> LENGTH: 19
<212> TYPE: DNA
<213> ORGANISM: Escherichia coli

<400> SEQUENCE: 1
ggacggggaa ctaactatg                                                    19

<210> SEQ ID NO 2
<211> LENGTH: 20
<212> TYPE: DNA
<213> ORGANISM: Escherichia coli

<400> SEQUENCE: 2
ccacgatgac gcaccacgcg                                                   20

```
<210> SEQ ID NO 3
<211> LENGTH: 30
<212> TYPE: DNA
<213> ORGANISM: Escherichia coli

<400> SEQUENCE: 3 ggaggggggca tatgaatggc gcacagtggg                              30

<210> SEQ ID NO 4
<211> LENGTH: 25
<212> TYPE: DNA
<213> ORGANISM: Escherichia coli

<400> SEQUENCE: 4 gggggggtcat gataatttct ccaac                                   25

<210> SEQ ID NO 5
<211> LENGTH: 28
<212> TYPE: DNA
<213> ORGANISM: Escherichia coli

<400> SEQUENCE: 5
ccgggtggcg taattatgcc ggtttacg                                 28

<210> SEQ ID NO 6
<211> LENGTH: 28
<212> TYPE: DNA
<213> ORGANISM: Escherichia coli

<400> SEQUENCE: 6
cgtaaaccgg cataattacg ccacccgg                                 28

<210> SEQ ID NO 7
<211> LENGTH: 14
<212> TYPE: PRT
<213> ORGANISM: Synechocystis PCC6803

<400> SEQUENCE: 7

Leu Glu Lys Phe Ala Glu Tyr Cys Phe Asn Lys Ser Thr Gly
  1               5                  10

<210> SEQ ID NO 8
<211> LENGTH: 21
<212> TYPE: PRT
<213> ORGANISM: Escherichia coli

<400> SEQUENCE: 8

Cys Ala Gln Trp Val Val His Ala Leu Arg Ala Gln Gly Val Asn Thr
  1               5                  10                  15

Val Phe Gly Tyr Gly
             20

<210> SEQ ID NO 9
<211> LENGTH: 20
<212> TYPE: PRT
<213> ORGANISM: Escherichia coli

<400> SEQUENCE: 9

Cys Val Trp Pro Leu Val Pro Pro Gly Ala Ser Asn Ser Glu Met Leu
  1               5                  10                  15

Glu Lys Leu Ser
             20
```

<210> SEQ ID NO 10
<211> LENGTH: 26
<212> TYPE: DNA
<213> ORGANISM: Escherichia coli

<400> SEQUENCE: 10 ggggtcatg aatggcgcac agtggg                                    26

<210> SEQ ID NO 11
<211> LENGTH: 34
<212> TYPE: DNA
<213> ORGANISM: Escherichia coli

<400> SEQUENCE: 11
gcgcgctcga gttgatttaa cggctgctgt aatg                          34

<210> SEQ ID NO 12
<211> LENGTH: 32
<212> TYPE: DNA
<213> ORGANISM: Escherichia coli

<400> SEQUENCE: 12
gcgcgaccgg ttgtgactgg cagcaacact gc                            32

<210> SEQ ID NO 13
<211> LENGTH: 31
<212> TYPE: DNA
<213> ORGANISM: Escherichia coli

<400> SEQUENCE: 13 gggggggctgc agtcatgata atttctccaa c                            31

<210> SEQ ID NO 14
<211> LENGTH: 22
<212> TYPE: DNA
<213> ORGANISM: MAIZE

<400> SEQUENCE: 14
atcagtacac agtcctgcca tc                                       22

<210> SEQ ID NO 15
<211> LENGTH: 20
<212> TYPE: DNA
<213> ORGANISM: MAIZE

<400> SEQUENCE: 15
gagacagccg ccgcaaccat                                          20

<210> SEQ ID NO 16
<211> LENGTH: 29
<212> TYPE: DNA
<213> ORGANISM: MAIZE

<400> SEQUENCE: 16
gggcccatat ggccaccgcc gccgccgcg                                29

<210> SEQ ID NO 17
<211> LENGTH: 29
<212> TYPE: DNA
<213> ORGANISM: MAIZE

<400> SEQUENCE: 17

```
gggccctcga ggcttccttc aagaagagc                              29
```

<210> SEQ ID NO 18
<211> LENGTH: 29
<212> TYPE: DNA
<213> ORGANISM: MAIZE

<400> SEQUENCE: 18

```
gggccaccgg tacatcaaag aagagcttg                              29
```

<210> SEQ ID NO 19
<211> LENGTH: 31
<212> TYPE: DNA
<213> ORGANISM: MAIZE

<400> SEQUENCE: 19

```
ggggctgcat tcagtacaca gtcctgccat c                           31
```

<210> SEQ ID NO 20
<211> LENGTH: 7
<212> TYPE: PRT
<213> ORGANISM: Synechocystis PCC6803

<400> SEQUENCE: 20

Leu Glu Lys Phe Ala Glu Tyr
 1               5

<210> SEQ ID NO 21
<211> LENGTH: 7
<212> TYPE: PRT
<213> ORGANISM: Synechocystis PCC6803

<400> SEQUENCE: 21

Cys Phe Asn Lys Ser Thr Gly
 1               5

<210> SEQ ID NO 22
<211> LENGTH: 21
<212> TYPE: PRT
<213> ORGANISM: MAIZE

<400> SEQUENCE: 22

Cys Lys Gly Ala Asp Ile Leu Val Glu Ser Leu Glu Arg Cys Gly Val
 1               5                  10                  15

Arg Asp Val Phe Ala
            20

<210> SEQ ID NO 23
<211> LENGTH: 21
<212> TYPE: PRT
<213> ORGANISM: MAIZE

<400> SEQUENCE: 23

Cys Ile Pro Ser Gly Gly Ala Phe Lys Asp Met Ile Leu Asp Gly Asp
 1               5                  10                  15

Gly Arg Thr Val Tyr
            20

<210> SEQ ID NO 24
<211> LENGTH: 44
<212> TYPE: DNA
<213> ORGANISM: Artificial Sequence
<220> FEATURE:
<223> OTHER INFORMATION: Description of Artificial Sequence: Synthetic, based on Salmonella typhimurium

<400> SEQUENCE: 24
ggatcctaag aaggagatat acccatggaa tccctgacgt taca        44

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 25
gtcgacgctc tcctgcagtt aggcaggcgt actcattc        38

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 26
gctttgctcc tggcggcttt accttgtggt aaaaccgc        38

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 27
gcggttttac cacaaggtaa agccgccagg agcaaagc        38

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 28
gcccctaaag acacaattat tcgcg        25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 29
cagcggcgcc gtcatcagca gagcg        25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic,
      based on Salmonella typhimurium -continued

```
<400> SEQUENCE: 30
gcgaaccacc actaccaaca atttg                                            25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 31
tatctccacg ccaaaggttt tcatt                                            25

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 32
gaatattgcc tgtcttttgg t                                                21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 33
gttaaagcag ttagcagcga t                                                21

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 34
tgctgaatat tgcctgtctt ttgg                                             24

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 35
ccgttaaagc agttagcagc gatagc                                           26

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Synthetic,
      based on Salmonella typhimurium
```

```
<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 37
gatatcctgc agttaacctg gagagtgata ctgttgacc                            39

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 38
gatatcccat gggacgctat ctggtcgagg gcgatg                               36

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic,
      based on Salmonella typhimurium

<400> SEQUENCE: 39
gtcgacgctc tcctgcagtt aggcaggcgt actcattc                             38

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic
      from Synechocystis species PCC6803

<400> SEQUENCE: 40
tgctgaatat gcgctgtctt ttggtaccga a                                    31

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
      from Synechocystis species PCC6803

<400> SEQUENCE: 41
ccgttaaacg ccgcagcagc gatagcgcc                                       29

<210> SEQ ID NO 42
<211> LENGTH: 178
<212> TYPE: PRT
<213> ORGANISM: Escherichia coli

<400> SEQUENCE: 42

Tyr Ala Val Asp Lys Ala Asp Leu Leu Leu Ala Leu Gly Val Arg Phe
 1               5                  10                  15
```

-continued

```
Asp Asp Arg Val Thr Lys Ile Glu Ala Phe Ala Ser Arg Ala Lys Ile
            20                  25                  30

Val His Val Asp Ile Asp Pro Ala Glu Ile Gly Lys Asn Lys Gln Pro
        35                  40                  45

His Val Ser Ile Cys Ala Asp Val Lys Leu Ala Leu Gln Gly Met Asn
    50                  55                  60

Ala Leu Leu Glu Gly Ser Thr Ser Lys Lys Ser Phe Asp Phe Gly Ser
65                  70                  75                  80

Trp Asn Asp Glu Leu Asp Gln Gln Lys Arg Glu Phe Pro Leu Gly Tyr
                85                  90                  95

Lys Thr Ser Asn Glu Glu Ile Gln Pro Gln Tyr Ala Ile Gln Val Leu
            100                 105                 110

Asp Glu Leu Thr Lys Gly Glu Ala Ile Ile Gly Thr Gly Val Gly Gln
        115                 120                 125

His Gln Met Trp Ala Ala Gln Tyr Tyr Thr Tyr Lys Arg Pro Arg Gln
    130                 135                 140

Trp Leu Ser Ser Ala Gly Leu Gly Ala Met Gly Phe Gly Leu Pro Ala
145                 150                 155                 160

Ala Ala Gly Ala Ser Val Ala Asn Pro Gly Val Thr Val Val Asp Ile
                165                 170                 175

Asp Gly
```

<210> SEQ ID NO 43
<211> LENGTH: 179
<212> TYPE: PRT
<213> ORGANISM: Escherichia coli

<400> SEQUENCE: 43

```
Tyr Ala Val Asp Ser Ser Asp Leu Leu Leu Ala Phe Gly Val Arg Phe
 1               5                  10                  15

Asp Asp Arg Val Thr Gly Lys Leu Glu Ala Phe Ala Ser Arg Ala Lys
            20                  25                  30

Ile Val His Ile Asp Ile Asp Ser Ala Glu Ile Gly Lys Asn Lys Gln
        35                  40                  45

Pro His Val Ser Ile Cys Ala Asp Ile Lys Leu Ala Leu Gln Gly Leu
    50                  55                  60

Asn Ser Ile Leu Glu Ser Lys Glu Gly Lys Leu Lys Leu Asp Phe Ser
65                  70                  75                  80

Ala Trp Arg Gln Glu Leu Thr Glu Gln Lys Val Lys His Pro Leu Asn
                85                  90                  95

Phe Lys Thr Phe Gly Asp Ala Ile Pro Pro Gln Tyr Ala Ile Gln Val
            100                 105                 110

Leu Asp Glu Leu Thr Asn Gly Asn Ala Ile Ile Ser Thr Gly Val Gly
        115                 120                 125

Gln His Gln Met Trp Ala Ala Gln Tyr Tyr Lys Tyr Arg Lys Pro Arg
    130                 135                 140

Gln Trp Leu Thr Ser Gly Gly Leu Gly Ala Met Gly Phe Gly Leu Pro
145                 150                 155                 160

Ala Ala Ile Gly Ala Ala Val Gly Arg Pro Asp Glu Val Val Val Asp
                165                 170                 175

Ile Asp Gly
```

<210> SEQ ID NO 44
<211> LENGTH: 179

```
<212> TYPE: PRT
<213> ORGANISM: Escherichia coli

<400> SEQUENCE: 44

Tyr Ala Val Asp Ser Ser Asp Leu Leu Ala Phe Gly Val Arg Phe
 1               5                  10                  15

Asp Asp Arg Val Thr Gly Lys Leu Glu Ala Phe Ala Ser Arg Ala Lys
            20                  25                  30

Ile Val His Ile Asp Ile Asp Ser Ala Glu Ile Gly Lys Asn Lys Gln
        35                  40                  45

Pro His Val Ser Ile Cys Ala Asp Ile Lys Leu Ala Leu Gln Gly Leu
    50                  55                  60

Asn Ser Ile Leu Glu Ser Lys Glu Gly Lys Leu Lys Leu Asp Phe Ser
65                  70                  75                  80

Ala Trp Arg Gln Glu Leu Thr Val Gln Lys Val Lys Tyr Pro Leu Asn
                85                  90                  95

Phe Lys Thr Phe Gly Asp Ala Ile Pro Pro Gln Tyr Ala Ile Gln Val
            100                 105                 110

Leu Asp Glu Leu Thr Asn Gly Ser Ala Ile Ile Ser Thr Gly Val Gly
        115                 120                 125

Gln His Gln Met Trp Ala Ala Gln Tyr Tyr Lys Tyr Arg Lys Pro Arg
    130                 135                 140

Gln Trp Leu Thr Ser Gly Gly Leu Gly Ala Met Gly Phe Gly Leu Pro
145                 150                 155                 160

Ala Ala Ile Gly Ala Ala Val Gly Arg Pro Asp Glu Val Val Val Asp
                165                 170                 175

Ile Asp Gly

<210> SEQ ID NO 45
<211> LENGTH: 180
<212> TYPE: PRT
<213> ORGANISM: Escherichia coli

<400> SEQUENCE: 45

Met Thr Met His Asn Ala Asp Val Ile Phe Ala Val Gly Val Arg Phe
 1               5                  10                  15

Asp Asp Arg Thr Thr Asn Asn Leu Ala Lys Tyr Cys Pro Asn Ala Thr
            20                  25                  30

Val Leu His Ile Asp Ile Asp Pro Thr Ser Ile Ser Lys Thr Val Thr
        35                  40                  45

Ala Asp Ile Pro Ile Val Gly Asp Ala Arg Gln Val Leu Glu Gln Met
    50                  55                  60

Leu Glu Leu Leu Ser Gln Glu Ser Ala His Gln Pro Leu Asp Glu Ile
65                  70                  75                  80

Arg Asp Trp Trp Gln Gln Ile Glu Gln Trp Arg Ala Arg Gln Cys Leu
                85                  90                  95

Lys Tyr Asp Thr His Ser Glu Lys Ile Lys Pro Gln Ala Val Ile Glu
            100                 105                 110

Thr Leu Trp Arg Leu Thr Lys Gly Asp Ala Tyr Val Thr Ser Asp Val
        115                 120                 125

Gly Gln His Gln Met Phe Ala Ala Leu Tyr Tyr Pro Phe Asp Lys Pro
    130                 135                 140

Arg Arg Trp Ile Asn Ser Gly Gly Leu Gly Thr Met Gly Phe Gly Leu
145                 150                 155                 160
```

```
Pro Ala Ala Leu Gly Val Lys Met Ala Leu Pro Glu Glu Thr Val Val
            165                 170                 175
Cys Val Thr Gly
        180
```

<210> SEQ ID NO 46
<211> LENGTH: 170
<212> TYPE: PRT
<213> ORGANISM: Escherichia coli

<400> SEQUENCE: 46

```
Phe Ala Val Gln Glu Cys Asp Leu Leu Ile Ala Val Gly Ala Arg Phe
  1               5                  10                  15
Asp Asp Arg Val Thr Gly Lys Leu Asn Thr Ser Ala Pro His Ala Ser
                 20                  25                  30
Val Ile His Met Asp Ile Asp Pro Ala Glu Met Asn Lys Leu Arg Gln
         35                  40                  45
Ala His Val Ala Leu Gln Gly Asp Leu Asn Ala Leu Leu Pro Ala Leu
     50                  55                  60
Gln Gln Pro Leu Asn Gln Cys Asp Trp Gln Gln His Cys Ala Gln Leu
 65                  70                  75                  80
Arg Asp Glu His Ser Trp Arg Tyr Asp His Pro Gly Asp Ala Ile Tyr
                 85                  90                  95
Ala Pro Leu Leu Leu Lys Gln Leu Ser Asp Arg Lys Pro Ala Asp Cys
            100                 105                 110
Val Val Thr Thr Asp Val Gly Gln His Gln Met Trp Ala Ala Gln His
        115                 120                 125
Ile Ala His Thr Arg Pro Glu Asn Phe Ile Thr Ser Ser Gly Leu Gly
    130                 135                 140
Thr Met Gly Phe Gly Leu Pro Ala Ala Val Gly Ala Gln Val Ala Arg
145                 150                 155                 160
Pro Asn Asp Thr Val Val Cys Ile Ser Gly
            165                 170
```

<210> SEQ ID NO 47
<211> LENGTH: 35
<212> TYPE: DNA
<213> ORGANISM: Escherichia coli

<400> SEQUENCE: 47
gccttaatta accatgaggg aagcggtgat cgccg                         35

<210> SEQ ID NO 48
<211> LENGTH: 34
<212> TYPE: DNA
<213> ORGANISM: Escherichia coli

<400> SEQUENCE: 48
tgcggtcgac tttgccgact accttggtga tctc                          34

<210> SEQ ID NO 49
<211> LENGTH: 41
<212> TYPE: DNA
<213> ORGANISM: Escherichia coli

<400> SEQUENCE: 49
cccaagcttg gcgccatgag taaaggagaa gaacttttca c                  41

<210> SEQ ID NO 50

```
<211> LENGTH: 36
<212> TYPE: DNA
<213> ORGANISM: Escherichia coli

<400> SEQUENCE: 50
gcgaccggtt tatttgtata gttcatccat gccatg                              36

<210> SEQ ID NO 51
<211> LENGTH: 39
<212> TYPE: DNA
<213> ORGANISM: Escherichia coli

<400> SEQUENCE: 51
agggaattcg tcgacaaatt tgctgaatat tgcctgtct                           39

<210> SEQ ID NO 52
<211> LENGTH: 38
<212> TYPE: DNA
<213> ORGANISM: Escherichia coli

<400> SEQUENCE: 52
ggcctcgagt tatttaattg tcccagcgtc aagtaatg                            38

<210> SEQ ID NO 53
<211> LENGTH: 41
<212> TYPE: DNA
<213> ORGANISM: Escherichia coli

<400> SEQUENCE: 53
agctttgttt aaaccatggt taaagttatc ggtcgtagat c                        41

<210> SEQ ID NO 54
<211> LENGTH: 43
<212> TYPE: DNA
<213> ORGANISM: Escherichia coli

<400> SEQUENCE: 54
cagcgtcgac ggcgccgtgg gatttgttaa agcagttagc agc                      43

<210> SEQ ID NO 55
<211> LENGTH: 31
<212> TYPE: DNA
<213> ORGANISM: Escherichia coli

<400> SEQUENCE: 55
catgccatgg gggaagcggt gatcgccgaa g                                   31

<210> SEQ ID NO 56
<211> LENGTH: 39
<212> TYPE: DNA
<213> ORGANISM: Escherichia coli

<400> SEQUENCE: 56
acgcgagctc ttatttaatt gtcccagcgt caagtaatg                           39

<210> SEQ ID NO 57
<211> LENGTH: 34
<212> TYPE: DNA
<213> ORGANISM: Escherichia coli

<400> SEQUENCE: 57
cgaattctat ggttaaagtt atcggtcgta gatc                                34
```

```
<210> SEQ ID NO 58
<211> LENGTH: 36
<212> TYPE: DNA
<213> ORGANISM: Escherichia coli

<400> SEQUENCE: 58
agcccgcggt tatttgtata gttcatccat gccatg                                    36

<210> SEQ ID NO 59
<211> LENGTH: 154
<212> TYPE: DNA
<213> ORGANISM: Nicotiana tabacum

<400> SEQUENCE: 59
gaatagatct acatacacct tggttgacac gagtatataa gtcatgttat actgttgaat          60
aacaagcctt ccattttcta ttttgatttg tagaaaacta gtgtgcttgg gagtccctga         120
tgattaaata aaccaagatt ttaccttaat taag                                     154

<210> SEQ ID NO 60
<211> LENGTH: 151
<212> TYPE: DNA
<213> ORGANISM: Nicotiana tabacum

<400> SEQUENCE: 60
gatcctggcc tagtctatag gaggttttga aagaaagga gcaataatca ttttcttgtt           60
ctatcaagag ggtgctattg ctcctttctt tttttctttt tatttattta ctagtatttt         120
acttacatag acttttttgt ttacgtattc t                                         151

<210> SEQ ID NO 61
<211> LENGTH: 185
<212> TYPE: DNA
<213> ORGANISM: Nicotiana tabacum

<400> SEQUENCE: 61
catatggcgt ccatgatctc ctcgtccgcg gtgaccacgg tcagccgcgc gtccacggtg          60
cagtcggccg cggtggcccc gttcggcggc ctcaagtcca tgaccggctt cccggtcaag         120
aaggtcaaca cggacatcac gtccatcacg agcaacggcg gcagggtgaa gtgcatgcga         180
agagc                                                                     185

<210> SEQ ID NO 62
<211> LENGTH: 6232
<212> TYPE: DNA
<213> ORGANISM: Unknown
<220> FEATURE:
<223> OTHER INFORMATION: nucleotides 1-2492: E. coli vector pLITMUS28
      (New England Biolabs, Inc.)
<223> OTHER INFORMATION: nucleotides 2493-5993: Nicotiana tabaceum
<223> OTHER INFORMATION: Nucleotides 5993-6232: E.coli vector pLITMUS28
      (New England Biolabs, Inc.)

<400> SEQUENCE: 62
gttaactacg tcaggtggca cttttcgggg aaatgtgcgc ggaacccta tttgtttatt           60 tttctaaata cattcaaata tgtatccgct catgagacaa taaccctgat aaatgcttca         120
ataatattga aaaggaaga gtatgagtat tcaacatttc cgtgtcgccc ttattccctt          180
ttttgcggca ttttgccttc ctgttttttgc tcacccagaa acgctggtga agtaaaaga         240 tgctgaagat cagttgggtg cacgagtggg ttacatcgaa ctggatctca acagcggtaa        300
gatccttgag agttttcgcc ccgaagaacg ttctccaatg atgagcactt ttaaagttct        360
```

-continued

```
gctatgtggc gcggtattat cccgtgttga cgccgggcaa gagcaactcg gtcgccgcat      420
acactattct cagaatgact tggttgagta ctcaccagtc acagaaaagc atcttacgga      480
tggcatgaca gtaagagaat tatgcagtgc tgccataacc atgagtgata acactgcggc      540
caacttactt ctgacaacga tcggaggacc gaaggagcta accgcttttt tgcacaacat      600
gggggatcat gtaactcgcc ttgatcgttg ggaaccggag ctgaatgaag ccataccaaa      660
cgacgagcgt gacaccacga tgcctgtagc aatggcaaca acgttgcgca aactattaac      720
tggcgaacta cttactctag cttcccggca acaattaata gactggatgg aggcggataa      780
agttgcagga ccacttctgc gctcggccct tccggctggc tggtttattg ctgataaatc      840
tggagccggt gagcgtgggt ctcgcggtat cattgcagca ctggggccag atggtaagcc      900
ctcccgtatc gtagttatct acacgacggg gagtcaggca actatggatg aacgaaatag      960
acagatcgct gagataggtg cctcactgat taagcattgg taactgtcag accaagttta     1020
ctcatatata ctttagattg atttaccccg gttgataatc agaaaagccc caaaaacagg     1080
aagattgtat aagcaaatat ttaaattgta acgttaata ttttgttaaa attcgcgtta     1140
aatttttgtt aaatcagctc attttttaac caataggccg aaatcggcaa aatcccttat     1200
aaatcaaaag aatagcccga gatagggttg agtgttgttc cagtttggaa caagagtcca     1260
ctattaaaga acgtggactc caacgtcaaa gggcgaaaaa ccgtctatca gggcgatggc     1320
ccactacgtg aaccatcacc caaatcaagt tttttggggt cgaggtgccg taaagcacta     1380
aatcggaacc ctaaagggag cccccgattt agagcttgac ggggaaagcg aacgtggcga     1440
gaaaggaagg gaagaaagcg aaaggagcgg gcgctagggc gctggcaagt gtagcggtca     1500
cgctgcgcgt aaccaccaca cccgccgcgc ttaatgcgcc gctacagggc gcgtaaaagg     1560
atctaggtga agatcctttt tgataatctc atgaccaaaa tcccttaacg tgagttttcg     1620
ttccactgag cgtcagaccc cgtagaaaag atcaaaggat cttcttgaga tccttttttt     1680
ctgcgcgtaa tctgctgctt gcaaacaaaa aaaccaccgc taccagcggt ggtttgtttg     1740
ccggatcaag agctaccaac tcttttttccg aaggtaactg gcttcagcag agcgcagata     1800
ccaaatactg ttcttctagt gtagccgtag ttaggccacc acttcaagaa ctctgtagca     1860
ccgcctacat acctcgctct gctaatcctg ttaccagtgg ctgctgccag tggcgataag     1920
tcgtgtctta ccgggttgga ctcaagacga tagttaccgg ataaggcgca gcggtcgggc     1980
tgaacggggg gttcgtgcac acagcccagc ttggagcgaa cgacctacac cgaactgaga     2040
tacctacagc gtgagctatg agaaagcgcc acgcttcccg aagggagaaa ggcggacagg     2100
tatccggtaa gcggcagggt cggaacagga gagcgcacga gggagcttcc agggggaaac     2160
gcctggtatc tttatagtcc tgtcgggttt cgccacctct gacttgagcg tcgatttttg     2220
tgatgctcgt caggggggcg gagcctatgg aaaaacgcca gcaacgcggc ctttttacgg     2280
ttcctggcct tttgctggcc ttttgctcac atgtaatgtg agttagctca ctcattaggc     2340
accccaggct ttacacttta tgcttccggc tcgtatgttg tgtggaattg tgagcggata     2400
acaatttcac acaggaaaca gctatgacca tgattacgcc aagctacgta atacgactca     2460
ctagtgggca gatcttcgaa tgcatcgcgc gcttgacgat atagcaattt gcttggatt     2520 tatcagtcga agcaggagac aatataccctt gatattctcg atcattcttt gattcaaagc     2580
atcgttccat ctcaattgaa aaagcaaata acgtttcaag aacaaatcta gttctgcttc     2640
cgtgttgctt ttgtattgtt ttttcttttt acccttcttt gtgtctgatt ccgcgtaatc     2700 tttttttaaga gcgttttgat gttttgagag aacagggccc agatttcctt tgttttctat     2760
```

```
atctgatcca cgctctttt  ctccttgact tgcgggttct tttgcttctt gaattcgatt   2820
ctttattttt ttatttgatc gtagaaaaaa gttttgtttt tggtttttat tgatgttttt   2880
attttgacta acattttcat ttgtattcaa atttaaaaga agtaatttgc ttggtataat   2940
ccacggtttt attttatata cattataaag tggtacaaat tctgggaaga accaaaattc   3000
cagattcaat atgggacgat ttaatatttt ttcattcatt cccatccaat caaaaaggc    3060 ttttttcgaa ttttttgat  tgttttctgg attttgatga atcgtaagat aaaaaagcc    3120 tttttatca  attttatcaa ttatttgata attattaata ccaatttag  tatttggatt   3180 actgttggta tcgatcttaa cccaggcctc aatatcttct ttttgtctaa gagaaaaatg   3240
gataattttc caatcaaaat attttctatc gagatttctt tctatatata gaatattgcc   3300
ttttcttaga taattattga tatgaagatt gccgagcata tcaaaaaggt tgtgtttgga   3360
cgtgttggaa ttagaagaaa tttcgaggtt cttatttact tgaaagggta atctagaaat   3420
aaaagagtca ttttttttt  cataattaat cgatttatat gctaaaagat catatctata   3480
acatttttga aaattatctt tttggtttgc taatgaatag agctcagaat cattttcttt   3540
tttgtaatga attaattggt cttttcata  tgaattccat ttgtttaaat ttcgattttg   3600
agccatacaa ccttgattaa ccctatttcg ccattttgt  ggcattaatc tagaccatct   3660
aatctgagat aaatcgtacg agaatactca atcatgaata aatgcaagaa ataacctct    3720 ccttctttt  ctataatgta aacaaaaag  tctatgtaag taaaatacta gtaaataaat   3780 aaaagaaaa  aagaaaagga gcaatagcac cctcttgata gaacaagaaa atgattattg   3840
ctcctttctt ttcaaaacct cctatagact aggccaggat cctcgagctt aattaaggta   3900
aaatcttggt ttatttaatc atcagggact cccaagcaca ctagttttct acaaatcaaa   3960
atagaaaata gaaaatggaa ggcttttat  tcaacagtat aacatgactt atatactcgt   4020
gtcaaccaag gtgtatgtag atctattcct gcaggatatc tggatccacg aagcttccca   4080
tgggaataga tctacataca ccttggttga cacgagtata taagtcatgt tatactgttg   4140
aataaaaagc cttccatttt ctattttgat ttgtagaaaa ctagtgtgct tgggagtccc   4200
tgatgattaa ataaaccaag attttaccgt ttaaacaccg gtgatcctgg cctagtctat   4260
aggaggtttt gaaagaaag  gagcaataat cattttcttg ttctatcaag agggtgctat   4320
tgctcctttc ttttttttct tttatttatt tactagtatt ttacttacat agactttttt   4380
gtttacatta tagaaaaaga aggagaggtt attttcttgc atttattcat gattgagtat   4440
tctcctaggc gtattgataa tgccgtctta accagttttt ccattgattg attctataac   4500
tctgaagttt cttatgtttt aattcagaat gaaatattcc tagtgttcga aaatagtcct   4560
ttattttagt cttaaggaaa aaagacgttc tgttatattg aagaacagat cttaatttag   4620
acaaattaat aacttggggt tgtgataatt tgtaaaatac atatgcttgt gataagtagg   4680
ataaatcaaa aaaaatatgt gaattttct  tactaatatt ataaagtgac ttttttatag   4740
tcgaaataaa gtgaattttt ttttgattat taatttttc  ttgatttatt tcattattgg   4800
aaatgtattt atcaatcaat tgtttgttg  attcaagaaa gagttgtgta ttaattctgg   4860
gaatattaat gatagataaa aatagatcga tgtataatct ttgaatgaat aattttagaa   4920
aataatggaa tttccatatt aatcgagtat ttcttctttt taatatttgg aaaatctttt   4980
ttggcgattc gaattttta  atattatttg ttttattagg actaatgtct atttctggag   5040
ttactttctt tttctctttt gtaattcttt ctatttgatt tttgattgta cttgttctat   5100
```

-continued

```
cagtcaaatc cttcattttg ctttctatca gtgaagaatt tggccaattt ccagattcaa      5160
tttgactaaa tgattcgtta attatctgat tactcattag agaatctttt tcttttttcg      5220
tttcattcga ttcatctatt tctttgagtc taaataatac aattggattt acttttgaaa      5280
gttctttttt catttttttt ataaatagac tactttgat aagccatttt ttggtttctt       5340
ttgaaattct tcgaaataat tttattttc ctttgaaaac ttttagagtt ataaaatatt       5400 tcttttgaa ttttccaatt tttttttcga gttccttaaa aatgggctca aaaaagaag        5460 ggcgttttcg gggagaacca aagggaagtt cagcttccat tccccaaact gttaaaaaac      5520
aaaaatcatc tttttgtttt ttcttttca ttagctctcc acgggaggag tacagtttag       5580
atatatgcca aggtttcaga caaaaggaa ataatattt gatctgaatg ccatctttca        5640
accaattttt tggaaattct gtttctgata attgaacacc attataagta catttaatat      5700
gcatttctct attccattcc tgcaaatctt cagaccattc aggaagttgc aagactaaca      5760
tacgcccgag atttttggct attatcaatg aaggtaatac aatatatttt cgaagaattg      5820
attgagttat taacatgtaa cctcttatta tttgcgcaaa aggaatggta tcccaggctt      5880
ctgctatctc tatccgtgct ttttcctttc ttttgttctc ccctttttg tccttttcct       5940 ttttctcttc tcttttttgtt tgttcttctc tagactctag aatcttgaat tcggtaccct     6000
ctagtcaagg ccttaagtga gtcgtattac ggactggccg tcgttttaca acgtcgtgac      6060
tgggaaaacc ctggcgttac ccaacttaat cgccttgcag cacatccccc tttcgccagc     6120
tggcgtaata gcgaagaggc ccgcaccgat cgcccttccc aacagttgcg cagcctgaat      6180
ggcgaatggc gcttcgcttg gtaataaagc ccgcttcggc gggcttttt tt               6232
```

<210> SEQ ID NO 63
<211> LENGTH: 6477
<212> TYPE: DNA
<213> ORGANISM: Unknown
<220> FEATURE:
<223> OTHER INFORMATION: Nucleotides 1-2482: E. coli vector pLITMUS28 (New England Biolabs, Inc.)
<223> OTHER INFORMATION: Nucleotides 2493-6242: Nicotiana tabaceum
<223> OTHER INFORMATION: Nucleotides 6243-6477: E. coli vector pLITMUS28 (New England Biolabs, Inc.)

<400> SEQUENCE: 63

```
gttaactacg tcaggtggca cttttcgggg aaatgtgcgc ggaaccccta tttgtttatt       60
tttctaaata cattcaaata tgtatccgct catgagacaa taaccctgat aaatgcttca      120
ataatattga aaaggaaga gtatgagtat tcaacatttc cgtgtcgccc ttattcccctt      180 ttttgcggca ttttgccttc ctgttttgc tcacccagaa acgctggtga agtaaaaga        240 tgctgaagat cagttgggtg cacgagtggg ttacatcgaa ctggatctca acagcggtaa     300
gatccttgag agttttcgcc ccgaagaacg ttctccaatg atgagcactt ttaaagttct      360
gctatgtggc gcggtattat cccgtgttga cgccgggcaa gagcaactcg gtcgccgcat     420
acactattct cagaatgact tggttgagta ctcaccagtc acagaaaagc atcttacgga     480
tggcatgaca gtaagagaat tatgcagtgc tgccataacc atgagtgata acactgcggc     540
caacttactt ctgacaacga tcggaggacc gaaggagcta accgcttttt tgcacaacat     600
gggggatcat gtaactcgcc ttgatcgttg ggaaccggag ctgaatgaag ccataccaaa     660
cgacgagcgt gacaccacga tgcctgtagc aatggcaaca acgttgcgca aactattaac     720
tggcgaacta cttactctag cttcccggca acaattaata gactggatgg aggcggataa     780
agttgcagga ccacttctgc gctcggccct tccggctggc tggtttattg ctgataaatc     840
```

```
tggagccggt gagcgtgggt ctcgcggtat cattgcagca ctggggccag atggtaagcc    900
ctcccgtatc gtagttatct acacgacggg gagtcaggca actatggatg aacgaaatag    960
acagatcgct gagataggtg cctcactgat taagcattgg taactgtcag accaagttta   1020
ctcatatata ctttagattg atttaccccg gttgataatc agaaaagccc caaaaacagg   1080
aagattgtat aagcaaatat ttaaattgta aacgttaata ttttgttaaa attcgcgtta   1140
aattttttgtt aaatcagctc attttttaac caataggccg aaatcggcaa aatcccttat   1200
aaatcaaaag aatagcccga gatagggttg agtgttgttc cagtttggaa caagagtcca   1260
ctattaaaga acgtggactc caacgtcaaa gggcgaaaaa ccgtctatca gggcgatggc   1320
ccactacgtg aaccatcacc caaatcaagt ttttggggt cgaggtgccg taaagcacta   1380
aatcggaacc ctaaagggag cccccgattt agagcttgac ggggaaagcg aacgtggcga   1440
gaaaggaagg gaagaaagcg aaaggagcgg gcgctagggc gctggcaagt gtagcggtca   1500
cgctgcgcgt aaccaccaca cccgccgcgc ttaatgcgcc gctacagggc gcgtaaaagg   1560
atctaggtga agatcctttt tgataatctc atgaccaaaa tcccttaacg tgagttttcg   1620
ttccactgag cgtcagaccc cgtagaaaag atcaaaggat cttcttgaga tccttttttt   1680
ctgcgcgtaa tctgctgctt gcaaacaaaa aaaccaccgc taccagcggt ggtttgtttg   1740
ccggatcaag agctaccaac tcttttttccg aaggtaactg gcttcagcag agcgcagata   1800
ccaaatactg ttcttctagt gtagccgtag ttaggccacc acttcaagaa ctctgtagca   1860
ccgcctacat acctcgctct gctaatcctg ttaccagtgg ctgctgccag tggcgataag   1920
tcgtgtctta ccgggttgga ctcaagacga tagttaccgg ataaggcgca gcggtcgggc   1980
tgaacggggg gttcgtgcac acagcccagc ttggagcgaa cgacctacac cgaactgaga   2040
tacctacagc gtgagctatg agaaagcgcc acgcttcccg aagggagaaa ggcggacagg   2100
tatccggtaa gcggcagggt cggaacagga gagcgcacga gggagcttcc agggggaaac   2160
gcctggtatc tttatagtcc tgtcgggttt cgccacctct gacttgagcg tcgatttttg   2220
tgatgctcgt caggggggcg gagcctatgg aaaaacgcca gcaacgcggc cttttttacgg   2280
ttcctggcct tttgctggcc ttttgctcac atgtaatgtg agttagctca ctcattaggc   2340
accccaggct ttacacttta tgcttccggc tcgtatgttg tgtggaattg tgagcggata   2400
acaatttcac acaggaaaca gctatgacca tgattacgcc aagctacgta atacgactca   2460
ctagtgggca gatcttcgaa tgcatcgcgc gcaattcacc gccgtatggc tgaccggcga   2520
ttactagcga ttccggcttc atgcaggcga gttgcagcct gcaatccgaa ctgaggacgg   2580
gttttttgggg ttagctcacc ctcgcgggat cgcgaccctt tgtcccggcc attgtagcac   2640
gtgtgtcgcc cagggcataa ggggcatgat gacttgacgt catcctcacc ttcctccggc   2700
ttatcaccgg cagtctgttc agggttccaa actcaacgat ggcaactaaa cacgagggtt   2760
gcgctcgttg cgggacttaa cccaacacct tacggcacga gctgacgaca gccatgcacc   2820
acctgtgtcc gcgttcccga aggcacccct ctctttcaag aggattcgcg gcatgtcaag   2880
ccctggtaag gttcttcgct tgcatcgaa ttaaaccaca tgctccaccg cttgtgcggg   2940
ccccgtcaa ttcctttgag tttcattctt gcgaacgtac tccccaggcg ggatacttaa   3000
cgcgttagct acagcactgc acgggtcgat acgcacagcg cctagtatcc atcgtttacg   3060
gctaggacta ctgggtatc taatcccatt cgctccccta gctttcgtct ctcagtgtca   3120
gtgtcggccc agcagagtgc tttcgccgtt ggtgttcttt ccgatctcta cgcatttcac   3180
```

```
cgctccaccg gaaattccct ctgccsctac cgtactccag cttggtagtt tccaccgcct    3240
gtccagggtt gagccctggg atttgacggc ggacttaaaa agccacctac agacgcttta    3300
cgcccaatca ttccggataa cgcttgcatc tctgtatta  ccgcggctgc tggcacagag    3360
ttagccgatg cttattcccc agataccgtc attgcttctt ctccgggaaa agaagttcac    3420
gacccgtggg ccttctacct ccacgcggca ttgctccgtc agctttcgcc cattgcggaa    3480
aattccccac tgctgcctcc cgtaggagtc tgggccgtgt ctcagtccca gtgtggctga    3540
tcatcctctc ggaccagcta ctgatcatcg ccttggtaag ctattgcctc accaactagc    3600
taatcagacg cgagccccctc ctcgggcgga ttcctccttt tgctcctcag cctacggggt    3660
attagcagcc gtttccagct gttgttcccc tcccaagggc aggttcttac gcgttactca    3720
cccgtccgcc actggaaaca ccacttcccg tccgacttgc atgtgttaag catgccgcca    3780
gcgttcatcc tgagccagga tcgaactctc catgagattc atagttgcat tacttatagc    3840
ttccttgttc gtagacaaag cggattcgga attgtcttc  attccaaggc ataacttgta    3900
tccatgcgct tcatattcgc ccggagttcg ctcccagaaa tatagccatc cctgccccct    3960
cacgtcaatc ccacgagcct cttatccatt tcattgaac  gacggcgggg gagcaaatcc    4020
aactagaaaa actcacattg ggcttaggga taatcaggct cgaactgatg acttccacca    4080
cgtcaaggtg acactctacc gctgagttat atcccttccc cgccccatcg agaaatagaa    4140
ctgactaatc ctaagtcaaa ggcgtacgag aatactcaat catgaataaa tgcaagaaaa    4200
taacctctcc ttcttttct  ataatgtaaa caaaaaagtc tatgtaagta aaatactagt    4260
aaataaataa aagaaaaaa  agaaaggagc aatagcaccc tcttgataga acaagaaaat    4320
gattattgct cctttctttt caaaacctcc tatagactag gccaggatcc tcgagcttaa    4380
ttaaggtaaa atcttggttt atttaatcat cagggactcc caagcacact agttttctac    4440
aaatcaaaat agaaatagaa aaatggaagg cttttttatc aacagtataa catgacttat    4500
atactcgtgt caaccaaggt gtatgtagat ctattcctgc aggatatctg gatccacgaa    4560
gcttcccatg ggaatagatc tacatacacc ttggttgaca cgagtatata agtcatgtta    4620
tactgttgaa taaaaagcct tccattttct attttgattt gtagaaaact agtgtgcttg    4680
ggagtccctg atgattaaat aaaccaagat tttaccgttt aaacaccggt gatcctggcc    4740
tagtctatag gaggttttga aaagaaagga gcaataatca ttttcttgtt ctatcaagag    4800
ggtgctattg ctccttttctt tttttctttt tatttattta ctagtatttt acttacatag    4860 actttttttgt ttacattata gaaaaagaag gagaggttat tttcttgcat ttattcatga    4920
ttgagtattc tcctagggtc gagaaactca acgccactat tcttgaacaa cttggagccg    4980
ggccttcttt tcgcactatt acggatatga aataatggt  caaaatcgga ttcaattgtc    5040
aactgcccct atcggaaata ggattgacta ccgattccga aggaactgga gttacatctc    5100
ttttccattc aagagttctt atgcgtttcc acgccccttt gagaccccga aaaatgcaca    5160
aattcctttt cttaggaaca catacaagat tcgtcactac aaaaaggata atggtaaccc    5220
taccattaac tacttcattt atgaatttca tagtaataga aatacatgtc ctaccgagac    5280
agaatttgga acttgctatc ctcttgccta gcaggcaaag atttacctcc gtggaaagga    5340
tgattcattc ggatcgacat gagagtccaa ctacattgcc agaatccatg ttgtatattt    5400
gaaagaggtt gacctccttg cttctctcat ggtacactcc tcttcccgcc gagccccttt    5460
tctcctcggt ccacagagac aaaatgtagg actggtgcca acaattcatc agactcacta    5520
agtcgggatc actaactaat actaatctaa tataatagtc taatatatct aatataatag    5580
```

-continued

```
aaaatactaa tataatagaa aagaactgtc ttttctgtat actttccccg gttccgttgc    5640
taccgcgggc tttacgcaat cgatcggatt agatagatat cccttcaaca taggtcatcg    5700
aaaggatctc ggagacccac caaagtacga aagccaggat ctttcagaaa acggattcct    5760
attcaaagag tgcataaccg catggataag ctcacactaa cccgtcaatt tgggatccaa    5820
attcgagatt ttccttggga ggtatcggga aggatttgga atggaataat atcgattcat    5880
acagaagaaa aggttctcta ttgattcaaa cactgtacct aacctatggg atagggatcg    5940
aggaagggga aaaccgaaag atttcacatg gtacttttat caatctgatt tatttcgtac    6000
ctttcgttca atgagaaaat gggtcaaatt ctacaggatc aaacctatgg gacttaagga    6060
atgatataaa aaaagagag ggaaaatatt catattaaat aaatatgaag tagaagaacc    6120
cagattccaa atgaacaaat tcaaacttga aaaggatctt ccttattctt gaagaatgag    6180
gggcaaaggg attgatcaag aaagatcttt tgttcttctt atatataaga tcgtgatggt    6240
accctctagt caaggcctta agtgagtcgt attacggact ggccgtcgtt ttacaacgtc    6300
gtgactggga aaaccctggc gttacccaac ttaatcgcct tgcagcacat ccccctttcg    6360
ccagctggcg taatagcgaa gaggcccgca ccgatcgccc ttcccaacag ttgcgcagcc    6420
tgaatggcga atggcgcttc gcttggtaat aaagcccgct tcggcgggct tttttt       6477
```

<210> SEQ ID NO 64
<211> LENGTH: 31
<212> TYPE: DNA
<213> ORGANISM: Nicotiana tabacum

<400> SEQUENCE: 64
aactgcagga atagatctac atacaccttg g                                    31

<210> SEQ ID NO 65
<211> LENGTH: 42
<212> TYPE: DNA
<213> ORGANISM: Nicotiana tabacum

<400> SEQUENCE: 65
ccgctcgagc ttaattaagg taaaatcttg gtttatttaa tc                        42

<210> SEQ ID NO 66
<211> LENGTH: 33
<212> TYPE: DNA
<213> ORGANISM: Nicotiana tabacum

<400> SEQUENCE: 66
gcgaccggtg atcctggcct agtctatagg agg                                  33

<210> SEQ ID NO 67
<211> LENGTH: 34
<212> TYPE: DNA
<213> ORGANISM: Nicotiana tabacum

<400> SEQUENCE: 67
aggcctagga gaatactcaa tcatgaataa atgc                                 34

<210> SEQ ID NO 68
<211> LENGTH: 34
<212> TYPE: DNA
<213> ORGANISM: Nicotiana tabacum

<400> SEQUENCE: 68
ttggcgcgct tgacgatata gcaattttgc ttgg                         34

<210> SEQ ID NO 69
<211> LENGTH: 34
<212> TYPE: DNA
<213> ORGANISM: Nicotiana tabacum

<400> SEQUENCE: 69
ttgcgtacga tttatctcag attagatggt ctag                         34

<210> SEQ ID NO 70
<211> LENGTH: 35
<212> TYPE: DNA
<213> ORGANISM: Nicotiana tabacum

<400> SEQUENCE: 70
ttgcctaggc gtattgataa tgccgtctta accag                        35

<210> SEQ ID NO 71
<211> LENGTH: 34
<212> TYPE: DNA
<213> ORGANISM: Nicotiana tabacum

<400> SEQUENCE: 71 agggtaccg aattcaagat tctagagtct agag                          34

<210> SEQ ID NO 72
<211> LENGTH: 34
<212> TYPE: DNA
<213> ORGANISM: Nicotiana tabacum

<400> SEQUENCE: 72
ttggcgcgca attcaccgcc gtatggctga ccgg                         34

<210> SEQ ID NO 73
<211> LENGTH: 34
<212> TYPE: DNA
<213> ORGANISM: Nicotiana tabacum

<400> SEQUENCE: 73
ttgcgtacgc ctttgactta ggattagtca gttc                         34

<210> SEQ ID NO 74
<211> LENGTH: 34
<212> TYPE: DNA
<213> ORGANISM: Nicotiana tabacum

<400> SEQUENCE: 74
ttgcctaggg tcgagaaact caacgccact attc                         34

<210> SEQ ID NO 75
<211> LENGTH: 35
<212> TYPE: DNA
<213> ORGANISM: Nicotiana tabacum

<400> SEQUENCE: 75 agggtacca tcacgatctt atatataaga agaac                         35

<210> SEQ ID NO 76
<211> LENGTH: 250
<212> TYPE: DNA
<213> ORGANISM: Nicotiana tabacum

<400> SEQUENCE: 76

-continued

```
gaattgtgag cgctcacaat tctaggatgt taattgcgcc gacatcataa cggttctggc      60
aaatattctg aaatgagctg ttgacaatta atcatcggct cgtataatgt gtggaattgt     120
gagcggataa caatttcaca caggaaacag accatggtga attctagagc tcgaggatcc    180
gcggtacccg ggcatgcatt cgaagcttcc ttaagcggcc gtcgaccgat gcccttgaga    240
gccttcaacc                                                            250
```

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: based
      on the ends of the Tn7 transposon

<400> SEQUENCE: 77

Cys Leu Asn Ile Gln
 1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 78

Val Phe Lys His Ala
 1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 79

Leu Phe Lys Gln Pro
 1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 80

Cys Leu Asn Ser Asp
 1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 81

Cys Leu Asn Ile Ser

-continued

```
                1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 82

Cys Leu Asn Thr Asp
  1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 83

Cys Leu Asn Asn Arg
  1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 84

Cys Leu Asn Ser Cys
  1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 85

Cys Leu Asn Ser Asp
  1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 86

Cys Leu Asn Thr Leu
  1               5

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: based on
``` the ends of the Tn7 transposon

<400> SEQUENCE: 87

Val Phe Lys Gln Pro
 1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 88

Cys Leu Asn Ser Met
 1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 89

Cys Leu Asn Asn Tyr
 1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 90

Cys Leu Asn Met Ala
 1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 91

Val Phe Lys His Lys
 1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 92

Cys Leu Asn Thr Lys
 1               5

<210> SEQ ID NO 93

```
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 93

Cys Leu Asn Lys Asp
 1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 94

Met Phe Lys Gln Ile
 1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 95

Cys Leu Asn Ile Ile
 1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 96

Leu Phe Lys His Glu
 1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 97

Val Phe Lys His Phe
 1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 98
```

Cys Leu Asn Ser Val
 1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 99

Val Phe Lys Gln Ile
 1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 100

Met Phe Lys Gln Ala
 1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 101

Leu Phe Lys His His
 1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 102

Leu Phe Lys His Gln
 1               5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 103

Met Phe Lys His Val
 1               5

<210> SEQ ID NO 104
<211> LENGTH: 5
<212> TYPE: PRT
<213> ORGANISM: Artificial Sequence
<220> FEATURE:

<223> OTHER INFORMATION: Description of Artificial Sequence: based on
      the ends of the Tn7 transposon

<400> SEQUENCE: 104

Val Phe Lys Gln Lys
 1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 105

Leu Phe Lys Gln Gln
 1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 106

Leu Phe Lys His Ser
 1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 107

Cys Leu Asn Thr Gly
 1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 108

Cys Leu Asn Ser Arg
 1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 109

Val Phe Lys His Leu
 1               5

```
<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 110

Cys Leu Asn Asn Ile
 1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 111

Leu Phe Lys His Gln
 1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 112

Cys Leu Asn Lys His
 1               5

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 113

Met Phe Lys Gln Tyr
 1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 114

Cys Leu Asn Lys Gln
 1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 115
```

Cys Leu Asn Met Ser
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 116

Leu Cys Leu Asn Ile Leu Ala
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 117

Asn Cys Leu Asn Ile Asn Ala
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 118

Leu Met Phe Lys His Leu Ser
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 119

Thr Leu Phe Lys His Thr Arg
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 120

Lys Val Phe Lys Gln Lys Glu
1               5

<210> SEQ ID NO 121
<211> LENGTH: 7
<212> TYPE: PRT
<213> ORGANISM: Artificial Sequence

```
<220> FEATURE:
<223> OTHER INFORMATION: Description of Artificial Sequence: based on
      the ends of the Tn7 transposon

<400> SEQUENCE: 121

His Leu Val Phe Lys His Leu
  1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 122

Leu Cys Leu Asn Thr Leu Leu
  1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 123

Leu Cys Leu Asn Asn Leu Val
  1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 124

Glu Val Phe Lys His Glu Gly
  1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 125

Lys Val Phe Lys Gln Lys Gly
  1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 126

Thr Cys Leu Asn Thr Thr Ile
  1               5
```

```
<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 127

Met Cys Leu Asn Asn Met Asn
 1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 128

Leu Leu Phe Lys Gln Leu Arg
 1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 129

Arg Cys Leu Asn Asn Arg Leu
 1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 130

Met Val Phe Lys Gln Met Ala
 1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 131

Ala Met Phe Lys Gln Ala Thr
 1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon
```

-continued

```
<400> SEQUENCE: 132

Leu Val Phe Lys His Leu Asp
  1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 133

Lys Met Phe Lys Gln Lys Thr
  1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: based on
      the ends of the Tn7 transposon

<400> SEQUENCE: 134

Tyr Cys Leu Asn Asn Tyr Phe
  1               5
```